(12) United States Patent
Park et al.

(10) Patent No.: US 10,176,894 B2
(45) Date of Patent: Jan. 8, 2019

(54) WEARABLE ELECTRONIC DEVICE AND METHOD FOR CONTROLLING THE SAME

(71) Applicant: Samsung Electronics Co., Ltd., Gyeonggi-do (KR)

(72) Inventors: Hyung-Jin Park, Gyeonggi-do (KR); Soo-Jin Park, Gyeonggi-do (KR); Na-Gyeom Yoo, Yongin-si (KR); Jae-Woong Chun, Suwon-si (KR); Hyun-Chul Choi, Suwon-si (KR); Hyo-Sun Choi, Gyeonggi-do (KR); Soo-Ji Hwang, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/061,955

(22) Filed: Mar. 4, 2016

(65) Prior Publication Data

US 2016/0259905 A1    Sep. 8, 2016

(30) Foreign Application Priority Data

Mar. 6, 2015    (KR) .......................... 10-2015-0031871

(51) Int. Cl.
*G16H 40/63* (2018.01)
*A61B 5/01* (2006.01)
(Continued)

(52) U.S. Cl.
CPC .............. *G16H 40/63* (2018.01); *A61B 5/01* (2013.01); *A61B 5/021* (2013.01); *A61B 5/024* (2013.01);
(Continued)

(58) Field of Classification Search
CPC .................................................. G06F 19/3406
(Continued)

(56) References Cited

U.S. PATENT DOCUMENTS 8,165,685 B1    4/2012  Knutson et al.
2002/0180762 A1*  12/2002  Lee .......................... G09G 3/20
                                                        345/649
(Continued)

FOREIGN PATENT DOCUMENTS

EP    2818964 A1    12/2014
KR    10-0737767    7/2007
(Continued)

OTHER PUBLICATIONS

International Search Report dated Jul. 4, 2016 in connection with International Patent Application No. PCT/KR2016/002211, 3 pages.
(Continued)

*Primary Examiner* — Omar Casillashernandez

(57) ABSTRACT

A method includes determining whether the electronic device is attached on a human body and controlling the electronic device based on information regarding at least one of a body condition of a user, the body condition measured when the electronic device is attached, the user wearing the electronic device a position where the electronic device is attached or detached, or when the electronic device is attached or detached. An electronic device includes a memory configured to store an instruction to enable the processor to determine whether the electronic device is attached on a human body and to control the electronic device based on information regarding at least one of a body condition as measured when the electronic device is attached, the user wearing the electronic device, a position where the electronic device is attached or detached, and a time when the electronic device is attached or detached.

23 Claims, 41 Drawing Sheets

(51) Int. Cl.
*A61B 5/00* (2006.01)
*A61B 5/021* (2006.01)
*A61B 5/024* (2006.01)
*A61B 5/0402* (2006.01)
*A61B 5/0476* (2006.01)
*A61B 5/0488* (2006.01)
*A61B 5/145* (2006.01)
*G06F 19/00* (2018.01)
*A61B 5/11* (2006.01)

(52) U.S. Cl.
CPC .......... *A61B 5/0402* (2013.01); *A61B 5/0476* (2013.01); *A61B 5/0488* (2013.01); *A61B 5/14532* (2013.01); *A61B 5/4884* (2013.01); *A61B 5/681* (2013.01); *G06F 19/00* (2013.01); *G06F 19/3481* (2013.01); *A61B 5/02438* (2013.01); *A61B 5/1118* (2013.01); *A61B 5/6831* (2013.01); *A61B 5/6843* (2013.01); *A61B 2560/0214* (2013.01); *A61B 2560/0266* (2013.01)

(58) Field of Classification Search
USPC ..................................................... 340/870.07
See application file for complete search history.

(56) References Cited

U.S. PATENT DOCUMENTS

| | | | |
|---|---|---|---|
| 2008/0117060 A1 | 5/2008 | Cuddihy et al. | |
| 2008/0214901 A1 | 9/2008 | Gehman et al. | |
| 2009/0127477 A1* | 5/2009 | Tanaka | B23K 26/0738 250/492.22 |
| 2010/0185068 A1* | 7/2010 | Park | A61B 5/021 600/324 |
| 2010/0227587 A1* | 9/2010 | Ohmoto | H04L 63/107 455/411 |
| 2011/0109329 A1* | 5/2011 | Diebold | A61B 5/02055 324/679 |
| 2011/0263950 A1 | 10/2011 | Larson et al. | |
| 2013/0085410 A1 | 4/2013 | Alberth et al. | |
| 2013/0234853 A1* | 9/2013 | H. Kazerouni | G08B 13/1427 340/572.1 |
| 2013/0300356 A1* | 11/2013 | Yang | H02J 7/0047 320/108 |
| 2014/0135644 A1 | 5/2014 | Kim | |
| 2014/0135960 A1 | 5/2014 | Choi | |
| 2014/0275852 A1* | 9/2014 | Hong | A61B 5/02427 600/301 |
| 2014/0378113 A1 | 12/2014 | Song et al. | |
| 2015/0135310 A1* | 5/2015 | Lee | A61B 5/681 726/20 |
| 2015/0289802 A1* | 10/2015 | Thomas | A61B 5/4809 600/301 |
| 2015/0340040 A1* | 11/2015 | Mun | G10L 17/22 704/246 |
| 2016/0380470 A1* | 12/2016 | Son | H02J 7/025 320/106 |

FOREIGN PATENT DOCUMENTS

KR 10-1183580 B1 9/2012
WO WO 2015/030294 A1 3/2015

OTHER PUBLICATIONS

Written Opinion of International Searching Authority dated Jul. 4, 2016 in connection with International Patent Application No. PCT/KR2016/002211, 6 pages.
Extended European Search Report dated Jul. 12, 2016 in connection with European Application No. 16159006.2, 9 pages.

* cited by examiner

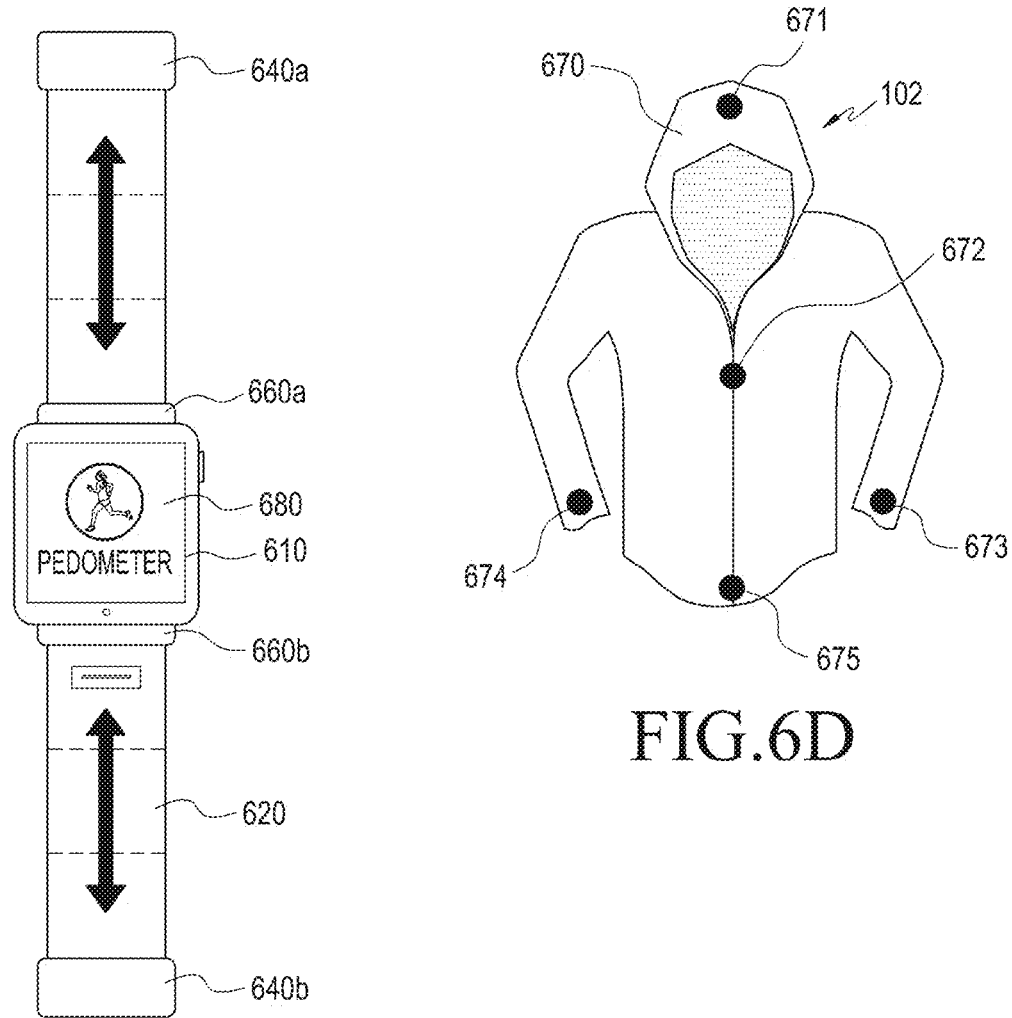
FIG.6C
FIG.6D
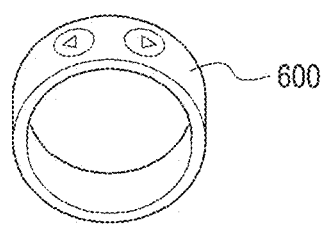
FIG.6E
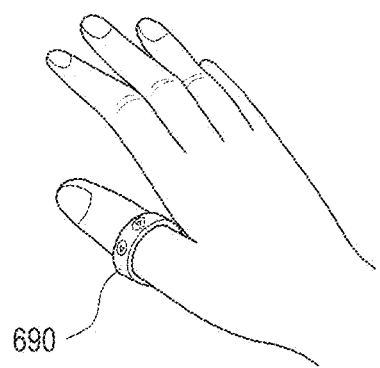
FIG.6F

WEARABLE ELECTRONIC DEVICE AND METHOD FOR CONTROLLING THE SAME

CROSS-REFERENCE TO RELATED APPLICATION AND CLAIM OF PRIORITY

The present application is related to and claims the benefit under 35 U.S.C. § 119(a) of a Korean patent application filed in the Korean Intellectual Property Office on Mar. 6, 2015 and assigned Serial No. 10-2015-0031871, the entire disclosure of which is incorporated herein by reference.

TECHNICAL FIELD

The present disclosure concerns wearable electronic devices and methods for controlling the same.

BACKGROUND

Vigorous development efforts are nowadays underway for wearable electronic devices. Wearable electronic devices may mean electronic devices that may be put on the user's body. As an electronic device is wearable on the user's body, the user may more freely use the electronic device. Furthermore, a wearable electronic device may come in tight contact with the user's body to obtain and analyze the user's bio information. The user may more readily use his body information by checking the result of analysis of the bio information by the wearable electronic device. Particularly, growing population aging and chronic diseases highlight wearable electronic devices. A wearable electronic device may include sensor electrodes for sensing electrical signals generated from the human body. A wearable electronic device may measure, e.g., an electromyogram (EMG), electrocardiogram (ECG), or electroencephalogram (EEG), detect the components of light transmitting the human body in an optical manner, or identify veins by radiating illuminations. A wearable electronic device may also measure motion information based on data sensed by a gyro sensor, acceleration sensor, geo-magnetic sensor, altimeter, or clinometer.

As described above, a wearable electronic device may measure the user's bio information or motion information. However, there is no research as to operations according to the conditions of wearing wearable electronic devices. For example, nowhere is such technology as carries out different operations depending on whether a wearable electronic device is worn or depending on where on the human body the wearable electronic device is worn.

The above information is presented as background information only to assist with an understanding of the present disclosure. No determination has been made, and no assertion is made, as to whether any of the above might be applicable as prior art with regard to the present disclosure.

SUMMARY

To address the above-discussed deficiencies, it is a primary object to provide, for use in a wearable electronic devices operating based on whether or where they are put on.

According to an embodiment of the present disclosure, a method for controlling an electronic device may include determining whether the electronic device is worn on a human body and controlling the electronic device or another electronic device interworkable with the electronic device based on at least one of information regarding a body condition of a user as measured when the electronic device is worn, information regarding the user wearing the electronic device, a portion worn, information regarding a place where the electronic device is attached or detached, and information regarding a time when the electronic device is attached or detached.

According to an embodiment of the present disclosure, an electronic device may include a processor and a memory electrically connected with the processor, and the memory may store instructions executed to enable the processor to determine whether the electronic device is worn on the user's body, and when determined to be worn, to control the electronic device or another electronic device interworkable with the electronic device based on at least one of information on a body state of the user as measured, information on the user wearing the electronic device, an area where the electronic device is worn, information on where the electronic device taken off is left, and information on a time when the electronic device is taken off.

Other aspects, advantages, and salient features of the disclosure will become apparent to those skilled in the art from the following detailed description, which, taken in conjunction with the annexed drawings, discloses exemplary embodiments of the disclosure.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 6A to 6F are a front and rear view illustrating an electronic device according to an embodiment of the present disclosure;

Throughout the drawings, like reference numerals will be understood to refer to like parts, components, and structures.

DETAILED DESCRIPTION

Figure 1:
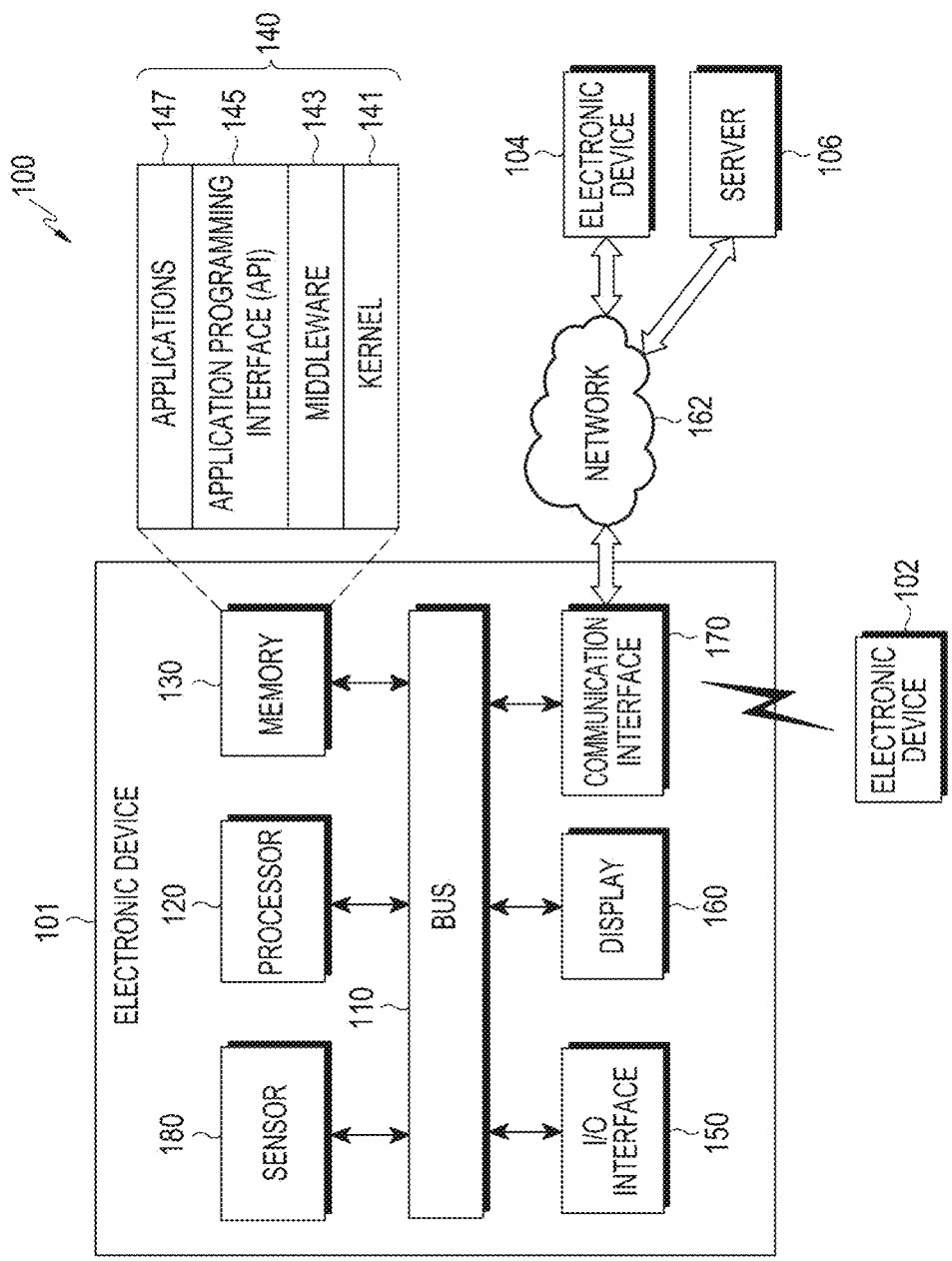
FIG. 1 illustrates a network environment including an electronic device according to an embodiment of the present disclosure.

FIGS. 1 through 38, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic devices. Hereinafter, embodiments of the present disclosure are described with reference to the accompanying drawings. However, it should be appreciated that the present disclosure is not limited to the embodiments, and all changes and/or equivalents or replacements thereto also belong to the scope of the present disclosure. The same or similar reference denotations may be used to refer to the same or similar elements throughout the specification and the drawings.

As used herein, the terms "have," "may have," "include," or "may include" a feature (e.g., a number, function, operation, or a component such as a part) indicate the existence of the feature and do not exclude the existence of other features.

As used herein, the terms "A or B," "at least one of A and/or B," or "one or more of A and/or B" may include all possible combinations of A and B. For example, "A or B," "at least one of A and B," "at least one of A or B" may indicate all of (1) including at least one A, (2) including at least one B, or (3) including at least one A and at least one B.

As used herein, the terms "first" and "second" may modify various components regardless of importance and do not limit the components. These terms are only used to distinguish one component from another. For example, a first user device and a second user device may indicate different user devices from each other regardless of the order or importance of the devices. For example, a first component may be denoted a second component, and vice versa without departing from the scope of the present disclosure.

It will be understood that when an element (e.g., a first element) is referred to as being (operatively or communicatively) "coupled with/to," or "connected with/to" another element (e.g., a second element), it can be coupled or connected with/to the other element directly or via a third element. In contrast, it will be understood that when an element (e.g., a first element) is referred to as being "directly coupled with/to" or "directly connected with/to" another element (e.g., a second element), no other element (e.g., a third element) intervenes between the element and the other element.

As used herein, the terms "configured (or set) to" may be interchangeably used with the terms "suitable for," "having the capacity to," "designed to," "adapted to," "made to," or "capable of" depending on circumstances. The term "configured (or set) to" does not essentially mean "specifically designed in hardware to." Rather, the term "configured to" may mean that a device can perform an operation together with another device or parts. For example, the term "processor configured (or set) to perform A, B, and C" may mean a generic-purpose processor (e.g., a CPU or application processor) that may perform the operations by executing one or more software programs stored in a memory device or a dedicated processor (e.g., an embedded processor) for performing the operations.

The terms as used herein are provided merely to describe some embodiments thereof, but not to limit the scope of other embodiments of the present disclosure. It is to be understood that the singular forms "a," "an," and "the" include plural references unless the context clearly dictates otherwise. All terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

For example, examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a PDA (personal digital assistant), a portable multimedia player (PMP), an MP3 player, a mobile medical device, a camera, or a wearable device (e.g., smart glasses, a head-mounted device (HMD), electronic clothes, an electronic bracelet, an electronic necklace, an electronic accessory, an electronic tattoo, a smart mirror, or a smart watch).

According to an embodiment of the present disclosure, the electronic device may be a smart home appliance. For example, examples of the smart home appliance may include at least one of a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box (e.g., Samsung HomeSync™, Apple TV™, or Google TV™), a gaming console (Xbox™, PlayStation™), an electronic dictionary, an electronic key, a camcorder, or an electronic picture frame.

According to an embodiment of the present disclosure, examples of the electronic device can include at least one of various medical devices (e.g., diverse portable medical measuring devices (a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, an sailing electronic device (e.g., a sailing navigation device or a gyro compass), avionics, security devices, vehicular head units, industrial or home robots, automatic teller's machines (ATMs), point of sales (POS) devices, or Internet of Things devices (e.g., a bulb, various sensors, an electric or gas meter, a sprinkler, a fire alarm, a thermostat, a street light, a toaster, fitness equipment, a hot water tank, a heater, or a boiler).

According to various embodiments of the disclosure, examples of the electronic device can at least one of part of furniture or building/structure, an electronic board, an electronic signature receiving device, a projector, or various measurement devices (e.g., devices for measuring water, electricity, gas, or electromagnetic waves). According to an embodiment of the present disclosure, the electronic device can be one or a combination of the above-listed devices. According to an embodiment of the present disclosure, the electronic device can be a flexible electronic device. The electronic device disclosed herein is not limited to the above-listed devices, and can include new electronic devices depending on the development of technology.

Hereinafter, electronic devices are described with reference to the accompanying drawings, according to various embodiments of the present disclosure. As used herein, the term "user" can denote a human or another device (e.g., an artificial intelligent electronic device) using the electronic device.

Referring to FIG. 1, according to an embodiment of the present disclosure, an electronic device 101 is included in a network environment 100. The electronic device 101 can include a bus 110, a processor 120, a memory 130, an input/output interface 150, a display 160, a communication interface 170, and a sensor 180. In some embodiments, the electronic device 101 can exclude at least one of the components or can add another component.

The bus 110 can include a circuit for connecting the components 120 to 180 with one another and transferring communications (e.g., control messages and/or data) between the components.

The processing module 120 can include one or more of a central processing unit (CPU), an application processor (AP), or a communication processor (CP). The processor 120 can perform control on at least one of the other components of the electronic device 101, and/or perform an operation or data processing relating to communication. The processor 120 can be denoted a controller, or the processor 120 can include a controller as part thereof.

The memory 130 can include a volatile and/or non-volatile memory. For example, the memory 130 can store commands or data related to at least one other component of the electronic device 101. According to an embodiment of the present disclosure, the memory 130 can store software and/or a program 140. The program 140 can include, e.g., a kernel 141, middleware 143, an application programming interface (API) 145, and/or an application program (or "application") 147. At least a portion of the kernel 141, middleware 143, or API 145 can be denoted an operating system (OS).

For example, the kernel 141 can control or manage system resources (e.g., the bus 110, processor 120, or a memory 130) used to perform operations or functions implemented in other programs (e.g., the middleware 143, API 145, or application program 147). The kernel 141 can provide an interface that allows the middleware 143, the API 145, or the application 147 to access the individual components of the electronic device 101 to control or manage the system resources.

The middleware 143 can function as a relay to allow the API 145 or the application 147 to communicate data with the kernel 141, for example. A plurality of applications 147 can be provided. The middleware 143 can control work requests received from the applications 147, e.g., by allocation the priority of using the system resources of the electronic device 101 (e.g., the bus 110, the processor 120, or the memory 130) to at least one of the plurality of applications 134.

The API 145 is an interface allowing the application 147 to control functions provided from the kernel 141 or the middleware 143. For example, the API 133 can include at least one interface or function (e.g., a command) for filing control, window control, image processing or text control.

As used herein, the term "application" can be denoted an application program as well.

The input/output interface 150 can serve as an interface that can, e.g., transfer commands or data input from a user or other external devices to other component(s) of the electronic device 101. Further, the input/output interface 150 can output commands or data received from other component(s) of the electronic device 101 to the user or the other external device.

The display 160 can include, e.g., a liquid crystal display (LCD), a light emitting diode (LED) display, an organic light emitting diode (OLED) display, or a microelectromechanical systems (MEMS) display, or an electronic paper display. The display 160 can display, e.g., various contents (e.g., text, images, videos, icons, or symbols) to the user. The display 160 can include a touchscreen and can receive, e.g., a touch, gesture, proximity or hovering input using an electronic pen or a body portion of the user.

For example, the communication interface 170 can set up communication between the electronic device 101 and an external electronic device (e.g., a first electronic device 102, a second electronic device 104, or a server 106). For example, the communication interface 170 can be connected with the network 162 through wireless or wired communication to communicate with the external electronic device.

The wireless communication can use at least one of, e.g., long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection can include at least one of universal serial bus (USB), high definition multimedia interface (HDMI), recommended standard 232 (RS-232), or plain old telephone service (POTS). The network 162 can include at least one of a telecommunication network, e.g., a computer network (e.g., LAN or WAN), Internet, or a telephone network.

The first and second external electronic devices 102 and 104 each can be a device of the same or a different type from the electronic device 101. According to an embodiment of the present disclosure, the server 106 can include a group of one or more servers. According to an embodiment of the present disclosure, all or some of operations executed on the electronic device 101 can be executed on another or multiple other electronic devices (e.g., the electronic devices 102 and 104 or server 106). According to an embodiment of the present disclosure, when the electronic device 101 should perform some function or service automatically or at a request, the electronic device 101, instead of executing the function or service on its own or additionally, can request another device (e.g., electronic devices 102 and 104 or server 106) to perform at least some functions associated therewith. The other electronic device (e.g., electronic devices 102 and 104 or server 106) can execute the requested functions or additional functions and transfer a result of the execution to the electronic device 101. The electronic device 101 can provide a requested function or service by processing the received result as it is or additionally. To that end, a cloud computing, distributed computing, or client-server computing technique can be used, for example.

According to an embodiment of the present disclosure, the sensor 180 can measure at least one of a bio signal of the user wearing the electronic device and motion information on the electronic device.

According to an embodiment of the present disclosure, the memory 130 can store instructions executed to enable the processor 120 to determine whether the electronic device is worn on the user's body, and when determined to be worn, to control the electronic device or another electronic device interworkable with the electronic device based on at least one of information on a body state of the user as measured, information on the user wearing the electronic device, an area where the electronic device is worn, information on where the electronic device is attached or detached, and information on a time when the electronic device is attached or detached.

According to an embodiment of the present disclosure, the memory 130 can store instructions executed to enable the processor 120 to determine at least one of the information on a body state of the user wearing the electronic device, the area where the electronic device is worn, the information on where the electronic device is attached or detached, and the information on a time when the electronic device is attached or detached based on at least one the bio signal and the motion information.

According to an embodiment of the present disclosure, the electronic device 101 can further include a coupler (not shown) for putting the electronic device 101 on the user. The memory 130 can store instructions executed to enable the processor 120 to determine whether the electronic device is worn based on movement information regarding the electronic device and a state in which the coupler of the electronic device is coupled.

The electronic device 101 can include at least one of a watch-type wearable electronic device, a band-type wearable electronic device, a clothes-type wearable electronic device, a ring-type wearable electronic device, and a necklace-type wearable electronic device. Further, the other electronic devices 102, 104, and 106 can include at least one of a smartphone, a server, a storage device, a display electronic device, and a home appliance.

Figure 2:
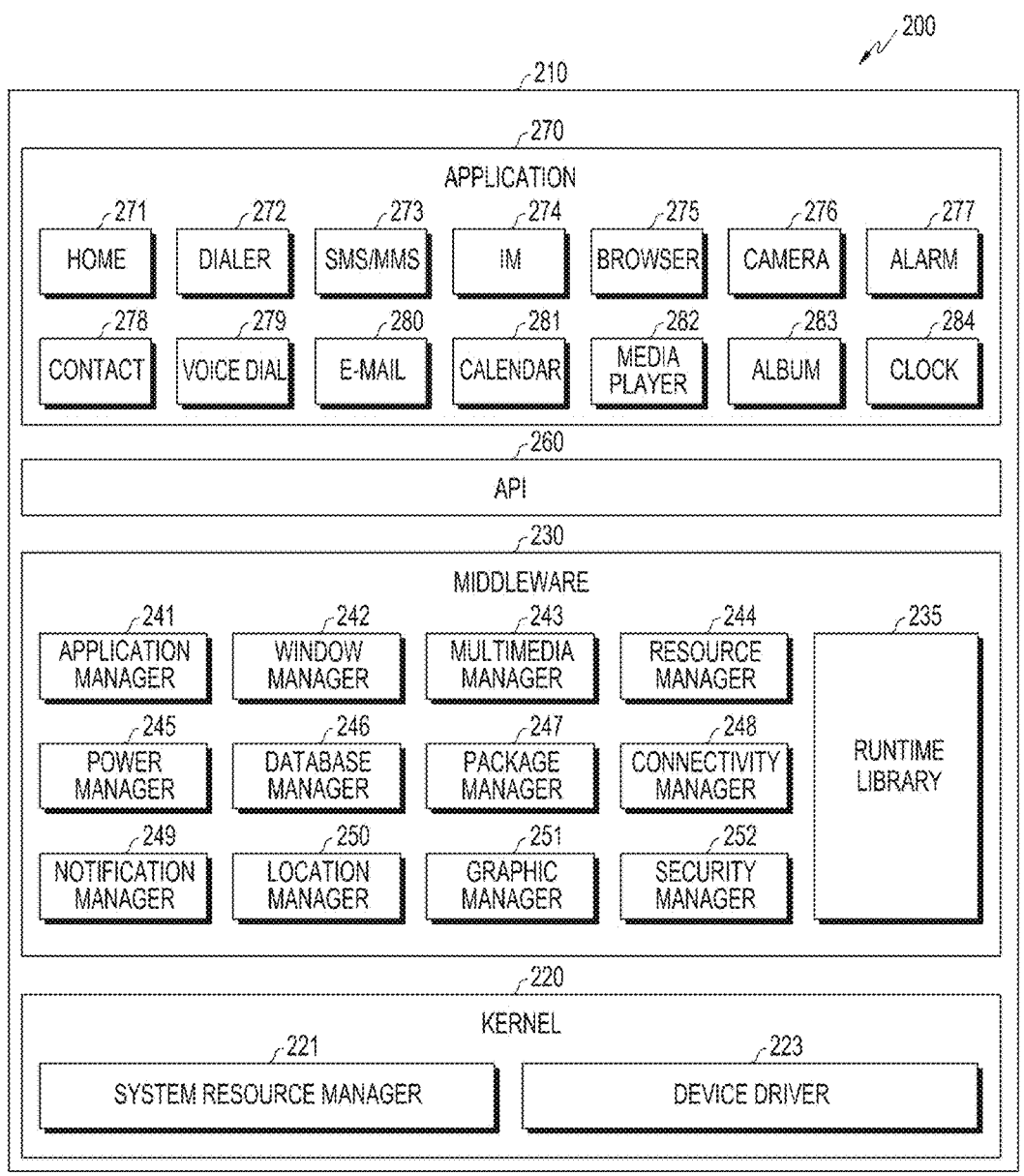
FIG. 2 is a block diagram illustrating a program module according to an embodiment of the present disclosure.

FIG. 2 is a block diagram 200 illustrating a program module 210 according to an embodiment of the present disclosure. According to an embodiment of the present disclosure, the program module 210 (e.g., the program 140) can include an operating system (OS) controlling resources related to the electronic device (e.g., the electronic device 101) and/or various applications (e.g., the application processor 147) driven on the operating system. The operating system can include, e.g., Android, iOS, Windows, Symbian, Tizen, or Bada.

The program 210 can include, e.g., a kernel 220, middleware 230, an application programming interface (API) 260, and/or an application 270. At least a part of the program module 210 can be preloaded on the electronic device or can be downloaded from a server (e.g., the server 106).

The kernel 220 (e.g., the kernel 141 of FIG. 1) can include, e.g., a system resource manager 221 or a device driver 223. The system resource manager 221 can perform control, allocation, or recovery of system resources. According to an embodiment of the present disclosure, the system resource manager 221 can include a process managing unit, a memory managing unit, or a file system managing unit. The device driver 223 can include, e.g., a display driver, a camera driver, a Bluetooth driver, a shared memory driver, a USB driver, a keypad driver, a Wi-Fi driver, an audio driver, or an inter-process communication (IPC) driver.

The middleware 230 can provide various functions to the application 270 through the API 260 so that the application 270 can efficiently use limited system resources in the electronic device or provide functions jointly required by applications 270. According to an embodiment of the present disclosure, the middleware 230 (e.g., middleware 143) can include at least one of a runtime library 235, an application manager 241, a window manager 242, a multimedia manager 243, a resource manager 244, a power manager 245, a database manager 246, a package manager 247, a connectivity manager 248, a notification manager 249, a location manager 250, a graphic manager 251, or a security manager 252.

The runtime library 235 can include a library module used by a compiler in order to add a new function through a programming language while, e.g., the application 270 is being executed. The runtime library 235 can perform input/output management, memory management, or operation on arithmetic functions.

The application manager 241 can manage the life cycle of at least one application of, e.g., the applications 270. The window manager 242 can manage GUI resources used on the screen. The multimedia manager 243 can grasp formats necessary to play various media files and use a codec appropriate for a format to perform encoding or decoding on media files. The resource manager 244 can manage resources, such as source code of at least one of the applications 270, memory or storage space.

The power manager 245 can operate together with, e.g., a basic input/output system (BIOS) to manage battery or power and provide power information necessary for operating the electronic device. The database manager 246 can generate, search, or vary a database to be used in at least one of the applications 270. The package manager 247 can manage installation or update of an application that is distributed in the form of a package file.

The connectivity manager 248 can manage wireless connectivity, such as, e.g., Wi-Fi or Bluetooth. The notification manager 249 can display or notify an event, such as a coming message, appointment, or proximity notification, of the user without interfering with the user. The location manager 250 can manage locational information on the electronic device. The graphic manager 251 can manage graphic effects to be offered to the user and their related user interface. The security manager 252 can provide various security functions necessary for system security or user authentication. According to an embodiment of the present disclosure, when the electronic device (e.g., the electronic device 101) has telephony capability, the middleware 230 can further include a telephony manager for managing voice call or video call functions of the electronic device.

The middleware 230 can include a middleware module forming a combination of various functions of the above-described components. The middleware 230 can provide a specified module per type of the operating system in order to provide a differentiated function. Further, the middleware 230 can dynamically omit some existing components or add new components.

The API 260 (e.g., the API 145) can be a set of, e.g., API programming functions and can have different configurations depending on operating systems. For example, in the case of Android or iOS, one API set can be provided per platform, and in the case of Tizen, two or more API sets can be offered per platform.

The application 270 (e.g., the application processor 147) can include one or more applications that can provide functions such as, e.g., a home 271, a dialer 272, a short message service (SMS)/multimedia messaging service (MMS) 273, an instant message (IM) 274, a browser 275, a camera 276, an alarm 277, a contact 278, a voice dial 279, an email 280, a calendar 281, a media player 282, an album 283, or a clock 284, a health-care (e.g., measuring the degree of workout or blood sugar), or provision of environmental information (e.g., provision of air pressure, moisture, or temperature information).

According to an embodiment of the present disclosure, the application 270 can include an application (hereinafter, "information exchanging application" for convenience) supporting information exchange between the electronic device (e.g., the electronic device 101) and an external electronic device (e.g., the electronic devices 102 and 104). Examples of the information exchange application can include, but is not limited to, a notification relay application for transferring specific information to the external electronic device, or a device management application for managing the external electronic device.

For example, the notification relay application can include a function for relaying notification information generated from other applications of the electronic device (e.g., the SMS/MMS application, email application, health-care application, or environmental information application) to the external electronic device (e.g., the electronic devices 102 and 104). Further, the notification relay application can receive notification information from, e.g., the external electronic device and can provide the received notification information to the user. The device management application can perform at least some functions of the external electronic device (e.g., the electronic device 102 or 104) communicating with the electronic device (for example, turning on/off the external electronic device (or some components of the external electronic device) or control of brightness (or resolution) of the display), and the device management application can manage (e.g., install, delete, or update) an application operating in the external electronic device or a service (e.g., call service or message service) provided from the external electronic device.

According to an embodiment of the present disclosure, the application 270 can include an application (e.g., a health-care application) designated depending on the attribute (e.g., as an attribute of the electronic device, the type of electronic device is a mobile medical device) of the external electronic device (e.g., the electronic devices 102 and 104). According to an embodiment of the present disclosure, the application 270 can include an application received from the external electronic device (e.g., the server 106 or electronic devices 102 and 104). According to an embodiment of the present disclosure, the application 270 can include a pre-loaded application or a third party application downloadable from a server. The names of the components of the program module 210 according to the shown embodiment can be varied depending on the type of operating system.

According to an embodiment of the present disclosure, at least a part of the program module 210 can be implemented in software, firmware, hardware, or in a combination of two or more thereof. At least a part of the programming module 210 can be implemented (e.g., executed) by e.g., a processor (e.g., the AP 210). At least a part of the program module 210 can include e.g., a module, program, routine, set of instructions, process, or the like for performing one or more functions.

Figure 3:
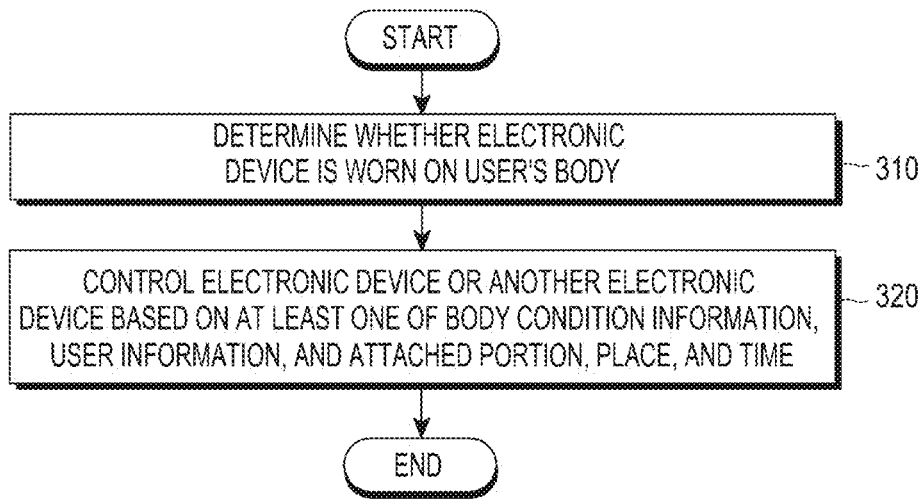
FIG. 3 is a flowchart illustrating a method for controlling an electronic device according to an embodiment of the present disclosure.

FIG. 3 is a flowchart illustrating a method for controlling an electronic device according to an embodiment of the present disclosure.

Referring to FIG. 3, the electronic device 101 can determine whether the electronic device is worn on the body in operation 310.

In operation 320, the electronic device 101 can control the electronic device or another electronic device interworkable with the electronic device based on at least one of information on a body state of the user, information on the user wearing the electronic device, an area where the electronic device is worn, information on where the electronic device is attached or detached, and information on a time when the electronic device is attached or detached, as measured when the electronic device is worn.

According to an embodiment of the present disclosure, determining whether the electronic device is worn on the body can include whether the electronic device is being attached or detached.

According to an embodiment of the present disclosure, determining whether the electronic device is worn on the body can include obtaining whether the electronic device is worn based on movement information regarding the electronic device and a state in which of the coupler of the electronic device is coupled.

According to an embodiment of the present disclosure, determining whether the electronic device is worn on the body can include determining that the electronic device is worn when detecting that the coupler is coupled after the electronic device has horizontally moved.

According to an embodiment of the present disclosure, the method for controlling the electronic device can further include determining whether the electronic device is worn on the left wrist or right wrist based on the direction in which the electronic device horizontally moves.

According to an embodiment of the present disclosure, controlling the electronic device or the other electronic device interworkable with the electronic device can include generating a control signal corresponding to the left wrist or right wrist based on the area where the electronic device is worn.

According to an embodiment of the present disclosure, determining whether the electronic device is worn on the body can include determining whether the electronic device is worn in tight contact with the body when determining that the electronic device is worn.

According to an embodiment of the present disclosure, determining whether the electronic device is worn on the body can include obtaining a sensed signal from the user and comparing a per-time measured value for the sensed signal with a predetermined reference value to determine whether the electronic device is worn in tight contact.

According to an embodiment of the present disclosure, the method for controlling the electronic device can include detecting an error signal from the sensed signal, and when the error signal exceeds a predetermined level, inducing the electronic device to be properly worn.

According to an embodiment of the present disclosure, inducing the electronic device to be properly worn can include changing a length of a strap so that the electronic device is worn in tight contact with the worn portion.

According to an embodiment of the present disclosure, inducing the electronic device to be properly worn can include sending a request for moving the electronic device to another worn portion for obtaining a sensed signal.

According to an embodiment of the present disclosure, determining whether the electronic device is worn on the body can include obtaining whether the electronic device is taken off based on movement information regarding the electronic device and a state in which of the coupler of the electronic device is coupled.

According to an embodiment of the present disclosure, the method for controlling the electronic device can further include determining that where the electronic device is taken off is a first place.

According to an embodiment of the present disclosure, the method for controlling the electronic device can further include setting the first place by a result of analyzing per-time location information or by the user's designation.

According to an embodiment of the present disclosure, the method for controlling the electronic device can further include performing wireless charging when the electronic device is disposed within a wireless chargeable range.

According to an embodiment of the present disclosure, the method for controlling the electronic device can further include sending out a wireless charging unavailable message when the electronic device is disposed off a wireless chargeable range.

According to an embodiment of the present disclosure, the method for controlling the electronic device can further include determining that where the electronic device is taken off is a place other than the first place.

According to an embodiment of the present disclosure, the method for controlling the electronic device can further include sending out an alert message when the distance between the electronic device and the user exceeds a predetermined level.

According to an embodiment of the present disclosure, the method for controlling the electronic device can further include measuring the distance between the electronic device and the user based on the strength of a communication signal between the electronic device and another electronic device carried by the user.

According to an embodiment of the present disclosure, the predetermined level can be set based on the strength of ambient noise sensed by the electronic device.

According to an embodiment of the present disclosure, the method for controlling the electronic device can further include obtaining a sensed signal from the user before determining whether the electronic device is taken off, and when determining that the electronic device is taken off, determining whether continuously obtaining the sensed signal is required.

According to an embodiment of the present disclosure, the method for controlling the electronic device can further include analyzing the sensed signal to obtain predicted health information, and when the predicted health information corresponds to a dangerous range, informing that continuously obtaining the sensed signal is required.

According to an embodiment of the present disclosure, the information regarding the user's body condition measured when the electronic device is worn can include at least one of a blood sugar value, a blood pressure value, a heart rate value, a temperature value, an electromyogram (EMG) value, an electrocardiogram (ECG) value, an electroencephalogram (EEG) value, and a vein value.

According to an embodiment of the present disclosure, the method for controlling the electronic device can further include generating second information including at least one of health information, authentication information, and emotion information using at least one of the blood sugar value, the blood pressure value, the heart rate value, the temperature value, the EMG value, the ECG value, the EEG value, and the vein value.

According to an embodiment of the present disclosure, the method for controlling the electronic device can further include determining whether the electronic device is taken off, and when determining that the electronic device is taken off, determining whether continuously obtaining the body condition information is required based on the second information.

According to an embodiment of the present disclosure, controlling the electronic device or the other electronic device interworkable with the electronic device can include performing user authentication to determine whether the user is previously registered or not registered.

According to an embodiment of the present disclosure, performing the user authentication can include obtaining a sensed signal from the user and comparing the sensed signal with a predetermined reference value to perform the user authentication.

According to an embodiment of the present disclosure, controlling the electronic device or the other electronic device interworkable with the electronic device can include, when the user is previously registered, sending out a signal indicating that the authentication succeeds to the other electronic device.

According to an embodiment of the present disclosure, controlling the electronic device or the other electronic device interworkable with the electronic device can include, when the user is not previously registered, sending out a signal indicating that the authentication fails to the other electronic device.

According to an embodiment of the present disclosure, the method for controlling the electronic device can further include obtaining the worn portion based on at least one of a sensed signal sensed from the user, length information regarding a strap of the electronic device, and movement information regarding the electronic device.

According to an embodiment of the present disclosure, the method for controlling the electronic device can further include determining that the worn portion of the electronic device is varied when the electronic device moves in a first direction as the length of the strap of the electronic device is varied.

According to an embodiment of the present disclosure, controlling the electronic device or the other electronic device interworkable with the electronic device can further include, when the worn portion is a wrist, determining a direction that the electronic device is worn and controlling the electronic device based on the determined direction.

According to an embodiment of the present disclosure, controlling the electronic device based on the determined worn direction can display a screen corresponding to a security mode when the worn direction faces an opposite direction of a position of the user.

According to an embodiment of the present disclosure, controlling the electronic device the other electronic device interworkable with the electronic device can include determining a mode determination signal corresponding to the worn portion and controlling the electronic device based on the mode determination signal.

According to an embodiment of the present disclosure, controlling the electronic device based on the mode determination signal can, when the worn portion is determined to be a wrist, determine that an ECG signal sensed from the wrist is the mode determination signal and control the electronic device based on the ECG signal.

According to an embodiment of the present disclosure, controlling the electronic device based on the mode determination signal can determine the user's health condition based on the ECG signal.

According to an embodiment of the present disclosure, when the worn portion is determined to be a forearm, controlling the electronic device based on the mode determination signal can determine that an EMG signal sensed from the forearm is the mode determination signal and can control the electronic device based on the EMG signal.

According to an embodiment of the present disclosure, controlling the electronic device based on the mode determination signal can generate a control signal based on the EMG signal.

According to an embodiment of the present disclosure, the control signal can be a signal to control the electronic device or another electronic device communicating with the electronic device.

According to an embodiment of the present disclosure, the method for controlling the electronic device can further include obtaining the worn portion as to whether the worn portion of the electronic device is a left wrist or a right wrist.

According to an embodiment of the present disclosure, controlling the electronic device or the other electronic device interworkable with the electronic device can determine an orientation of a screen of the electronic device corresponding to whether the worn portion is the left wrist or the right wrist.

According to an embodiment of the present disclosure, controlling the electronic device or the other electronic device interworkable with the electronic device can determine movement information regarding the electronic device corresponding to whether the worn portion is the left wrist or the right wrist.

According to an embodiment of the present disclosure, obtaining the worn portion can determine whether the worn portion is the left wrist or the right wrist based on a coupled state of a coupler of the electronic device and movement information regarding the electronic device.

According to an embodiment of the present disclosure, controlling the electronic device or the other electronic device interworkable with the electronic device can control the electronic device based on a distance between the worn portion and a predetermined body portion of the user.

According to an embodiment of the present disclosure, controlling the electronic device or the other electronic device interworkable with the electronic device can control an output volume of the electronic device based on a distance between the worn portion and the user's ear.

According to an embodiment of the present disclosure, controlling the electronic device or the other electronic device interworkable with the electronic device can control a screen resolution of the electronic device based on a distance between the worn portion and the user's eye.

According to an embodiment of the present disclosure, controlling the electronic device or the other electronic device interworkable with the electronic device can control a microphone sensitivity of the electronic device based on a distance between the worn portion and the user's mouth.

According to an embodiment of the present disclosure, controlling the electronic device or the other electronic device interworkable with the electronic device can control a vibration output of the electronic device based on a vibration strength corresponding to the worn portion.

According to an embodiment of the present disclosure, controlling the electronic device or the other electronic device interworkable with the electronic device can inverse and display a screen of the electronic device when the worn portion is determined to be around the neck.

According to an embodiment of the present disclosure, obtaining the worn portion can obtain depth information regarding the user's arm or leg where the electronic device is worn.

According to an embodiment of the present disclosure, controlling the electronic device or the other electronic device interworkable with the electronic device can include obtaining a sensed signal from the worn portion, obtaining a fatigue of the worn portion from a result of analyzing the sensed signal, and performing an operation corresponding to the fatigue when the fatigue exceeds a predetermined level.

According to an embodiment of the present disclosure, the operation corresponding to the fatigue can alternately increase and decrease the length of a strap of the electronic device or waiting until the fatigue is down to the predetermined level or less.

According to an embodiment of the present disclosure, controlling the electronic device or the other electronic device interworkable with the electronic device can further include obtaining a sensed signal from the worn portion and inducing a predetermined user position corresponding to obtaining the sensed signal.

According to an embodiment of the present disclosure, the method for controlling the electronic device can further include obtaining a voice from the user as obtained through a microphone of the electronic device and displaying a message indicating to stop generating the voice while obtaining the sensed signal.

According to an embodiment of the present disclosure, the method for controlling the electronic device can further include determining whether the user position is taken based on a sensed signal from a motion sensor of the electronic device.

According to an embodiment of the present disclosure, controlling the electronic device or the other electronic device interworkable with the electronic device can further include establishing a communication connection with the other electronic device and transmitting length information regarding a strap of the electronic device to the other electronic device, wherein when determining that no change is made to the length information regarding the strap, the other electronic device can determine that user authentication succeeds.

According to an embodiment of the present disclosure, controlling the electronic device or the other electronic device interworkable with the electronic device can further include obtaining an interoperation with an external tag and determining the worn portion based on the obtained interoperation.

According to an embodiment of the present disclosure, controlling the electronic device or the other electronic device interworkable with the electronic device can further include measuring a bio signal, receiving at least one of information on the thickness of a piece of clothes and information on the material of the piece of clothes from the external tag, and compensating for the bio signal based on the at least one of the information on the thickness of the piece of clothes and the information on the material of the piece of clothes.

Controlling the electronic device or the other electronic device interworkable with the electronic device can further include obtaining first information from the other electronic device, obtaining second information of the same type as the first information sensed by the electronic device, and determining the worn portion based on a result of comparing the first information with the second information.

Figure 4:
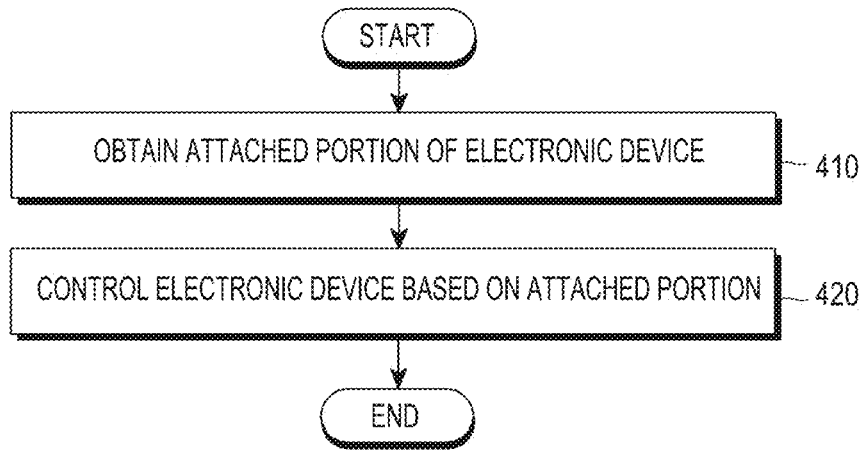
FIG. 4 is a flowchart illustrating a method for controlling an electronic device according to an embodiment of the present disclosure.

FIG. 4 is a flowchart illustrating a method for controlling an electronic device according to an embodiment of the present disclosure.

In operation 410, the electronic device 101 can obtain the area where the electronic device 101 is worn.

According to an embodiment of the present disclosure, the electronic device 101 can obtain the worn portion of the electronic device 101 based on information on the length of a strap included or connected to the electronic device 101. The electronic device 101 can previously store correlation information between the worn portion worn by the user and information on the length of the strap corresponding to the worn portion. For example, the correlation information indicating that the length of the strap is in a range from a to b when the worn portion is a wrist or the correlation information indicating that the length of the strap is a range from c to d when the worn portion is a forearm can be previously stored. The electronic device 101 can obtain the information indicating that the length of the strap is e that is between c and d and can determine that the worn portion is the forearm based on the previously stored correlation information.

According to an embodiment of the present disclosure, the electronic device 101 can obtain the worn portion based on movement information regarding the electronic device 101. For example, the electronic device 101 can include a sensor that can measure at least one of a displacement, a speed, and an acceleration and can measure at least one of the displacement, the speed, and the acceleration. When the electronic device 101 measures a displacement in an upper direction and a displacement in a left direction and then measures a coupling of the coupler, the electronic device 101 can determine that the worn portion is the left wrist. This is described below in greater detail.

The electronic device 101 can obtain the worn portion using an obtained bio signal, e.g., an electromyogram (EMG) signal or an electrocardiogram (ECG) signal. The electronic device 101 can also obtain the worn portion based on the strength or waveform of the bio signal.

Specifically, the electronic device 101 can previously measure the user's bio signals, e.g., an ECG, an EMG, a heart rate monitor (HRM) value, or a vein, for each body part of the user, e.g., the user's arm, leg, left/right, depth, or inside/outside. The electronic device 101 can obtain the worn portion by comparing bio information signals measured from the worn portion when the user wears the electronic device with characteristic information on the bio signal for each body part previously stored. Here, the characteristic bio signal for each body part can be stored in the electronic device 101 or another electronic device communicable with the electronic device 101. Since there are various electronic devices worn or carried by the user or the user's bio signals can be logged through various routes by various electronic devices, the collected information can be compiled and stored in a common storage means. Further, by doing so, lacking information regarding such various information can be made up between the electronic devices. Accordingly, the information collected through each electronic device can be stored in a common database, and the electronic device 101 can send a query for necessary information to the common database, receive a return, and make a comparison. According to an embodiment of the present disclosure, a comparing process can also be performed on the common database, and the electronic device 101 can also receive resultant values obtained by performing the process from the common database.

The electronic device 101 or the common database can use results of comparison of a plurality of information items rather than only one type of bio information for accurate determination as to the measured area. For example, when it is difficult to position the measured area only by specifying an EMG signal, the electronic device 101 can determine the measured area by simultaneously an EMG and an ECG. Or, in order to identify the depth of a corresponding arm whichever it is around the shoulder or hand, the electronic device 101 can utilize a change in shape of the vein or ECG/EMG information according to the depth of the arm, i.e., how far away from the end (i.e., the hand) of the arm the electronic device 101 is worn and can distinguish whether it is the inside or outside of the arm and leg.

Besides the method for determining the current worn portion by comparing measured bio signals by the electronic device 101, there can also be a method for recognizing the current worn position through communication or cooperation with another wearable electronic device. For example, the electronic device 101 can determine the current worn portion of the electronic device 101 by interpreting information occurring from various tags or sensors included in clothes or shoes. That is, when a near-field communication (NFC) tag positioned on a sleeve of clothes worn contacts the electronic device 101, the electronic device 101 can recognize that the user puts the electronic device 101 on his wrist. As another example, the electronic device 101 can receive measured values from a gravity sensor or altitude sensor embedded in a shoe and can compare the values with values measured by a gravity sensor included in the electronic device 101. For example, the electronic device 101 can estimate how above the shoes the user wears the electronic device 101 by such comparison.

According to an embodiment of the present disclosure, the electronic device 101 can also determine the worn portion based on information received from an external tag or sensor. The electronic device 101 can receive information on the material or thickness of the clothes the user is wearing from the external tag or sensor. The electronic device 101 can perform compensation for a bio signal measured through the electronic device 101 based on the received material or thickness information.

According to an embodiment of the present disclosure, the electronic device 101 can previously store body features for the amount of fat or thickness of skin or body frame for each user. Or, the electronic device 101 can compute the amount of fat consumed through comparison as to the degree by which the strap is extended or skin conductance levels. The electronic device 101 can variably set, e.g., the sensitivity of the sensor corresponding to the body features. That is, since the body features can differ per user depending on the amount of muscles/fat or height/age/gender, the electronic device 101 can correct the measured bio signal by predicting the amount of fat of the body portion. Further, the electronic device 101 can differentiate corrected values for body features per person or group and can correct the measured bio signal through the corrected values.

Further, the electronic device 101 can determine the worn portion using data sensed by various sensors, e.g., a geomagnetic sensor, altitude sensor, slope sensor, or gravity sensor, and this is described below in greater detail.

Or, the electronic device 101 can determine the worn portion based on the user's input. For example, the user can input a user input indicating the worn portion to the electronic device 101. The electronic device 101 can determine the worn portion based on the received user input.

Further, the electronic device 101 can determine a direction worn as well as the worn portion.

In operation 420, the electronic device 101 can control the electronic device 101 based on the worn portion. According to an embodiment of the present disclosure, the electronic device 101 can determine a mode determination signal based on the worn portion and can control the electronic device 101 based on the determined mode determination signal. For example, when the worn portion is determined as a wrist, the electronic device 101 can determine an ECG signal sensed from the wrist as the mode determination signal and can control the electronic device 101 based on the ECG signal.

In another embodiment, when the worn portion is determined as a forearm, the electronic device 101 can determine an EMG signal sensed from the forearm and can control the electronic device 101 based on the EMG signal.

In another embodiment, the electronic device 101 can determine and display an orientation of the screen of the electronic device 101, corresponding to whether the worn portion is a left wrist or right wrist.

In another embodiment, the electronic device 101 can control the electronic device 101 based on the distance between the obtained worn portion and a predetermined body portion of the user. For example, the electronic device 101 can control the output volume of the electronic device based on the distance between the worn portion and the user's ear. Further, the electronic device 101 can control the screen resolution of the electronic device 101 based on the distance between the obtained worn portion and the user's eye. The electronic device 101 can control the sensitivity of the microphone of the electronic device 101 based on the distance between the worn portion and the user's mouth.

In another embodiment, the electronic device 101 can control a vibrational output of the electronic device 101 based on the strength of vibration corresponding to the obtained worn portion.

In another embodiment, when the worn portion is obtained as around the neck, the electronic device 101 can invert and display its screen.

Figure 5:
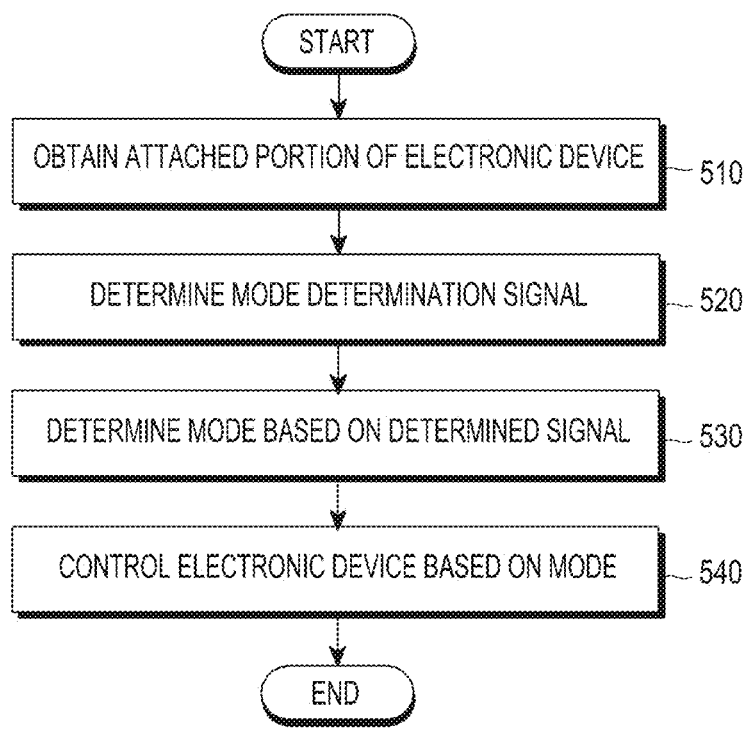
FIG. 5 is a flowchart illustrating a method for controlling an electronic device according to an embodiment of the present disclosure.

FIG. 5 is a flowchart illustrating a method for controlling an electronic device according to an embodiment of the present disclosure.

In operation 510, the electronic device 101 can obtain the area where the electronic device 101 is worn. For example, the electronic device 101 can determine the worn portion of the electronic device 101 as a wrist or forearm. For example, the electronic device 101 can determine the worn portion of the electronic device 101 as a wrist or forearm.

In operation 520, the electronic device 101 can determine the mode determination signal based on the obtained worn portion. In an embodiment, when the worn portion is determined as the wrist, the electronic device 101 can determine the mode determination signal as an ECG signal. Or, when the worn portion is determined as the forearm, the electronic device 101 can determine the mode determination signal as an EMG signal.

The ECG signal can be sensed relatively better on the wrist than on the forearm, and the EMG signal can be sensed relatively better on the forearm than on the wrist. The EMG signal can be used to recognize, e.g., a movement of a muscle, and can be more precisely measured on a body portion with relatively more muscles, e.g., the forearm. The ECG signal can be used to recognize, e.g., information such as an electrocardiogram, and can be more precisely measured on a body portion where the distance between the blood vessel and the skin is shorter, e.g., the wrist.

In operation 530, the electronic device 101 can determine a mode based on the determined signal. In an embodiment, when the ECG signal is determined as the mode determination signal, the electronic device 101 can operate in a health information monitoring mode in which the user's health information is monitored. In operation 540, the electronic device 101 can monitor the user's health information using the ECG signal. In another embodiment, when the EMG signal is determined as the mode determination signal, the electronic device 101 can operate in a control mode using the user's EMG signal. In operation 540, the electronic device 101 can output a control signal using the EMG signal. For example, the electronic device 101 can obtain an EMG signal corresponding to the operation of the user closing his index finger with the remaining fingers opened. The electronic device 101 can output a first control signal corresponding to the user's index finger being opened. In another embodiment, the electronic device 101 can obtain an EMG signal corresponding to the operation of the user opening his middle finger while opening the other fingers. The electronic device 101 can output a second control signal corresponding to the user's middle finger being opened. The first control signal or the second control signal can be used to control the electronic device 101 or another electronic device wiredly or wirelessly connected with the electronic device 101.

As described above, the electronic device 101 can determine a mode determination signal according to the obtained worn portion and determine an operation mode to operate. Meanwhile, the user can pull the electronic device 101 worn on his wrist up to the forearm. In this case, the electronic device 101 can change the mode determination signal from the ECG signal to the EMG signal. The electronic device 101 can change the operation mode from the health information monitoring mode to the control mode. Or, the user can pull the electronic device 101 worn on the forearm down to the wrist. In this case, the electronic device 101 can change the mode determination signal from the EMG signal to the ECG signal. The electronic device 101 can change the operation mode from the control mode to the health information monitoring mode.

According to an embodiment of the present disclosure, the electronic device 101 can measure an ECG or HRM signal even in the control mode. The electronic device 101 can recognize a gesture through the EMG signal in the control mode while simultaneously generating auxiliary information using information such as the ECG or HRM signal.

For example, the electronic device 101 can recognize a gesture by measuring the user's EMG signal, along with the HRM signal, to grasp the user's health condition while he plays game. When the user's heart rate increases, the electronic device 101 can determine that the sensitivity of the user playing game increases. In such case, for example, when the user performs an operation, e.g., shooting, while playing a video game, the electronic device 101 can adjust parameters, such as, e.g., adjusting the probability of accurately shooting the target or correcting an error as to the accuracy of the controller itself.

According to an embodiment of the present disclosure, when the electronic device 101 is in the health information monitoring mode, the electronic device 101 can determine the user's mood change through the ECG signal. Further, the electronic device 101 can ancillary compute an effect of exercise through the HRM, EMG, or ECG signal. The electronic device 101 can trace the user's mood and effect of exercise during workout and select and play proper music corresponding thereto. Here, the information primarily measured, such as the motion information measured for the electronic device 101 or measured bio signal can be referred to as first information. Further, the information obtained by performing various types of analysis on the measured first information, such as the effect of exercise or mood state, can be referred to as second information.

According to an embodiment of the present disclosure, the electronic device 101 can provide a notification regarding a proper body portion to enable measurement to be done appropriate for the purpose of measurement. Further, the electronic device 101 can provide information on movement to the corresponding body portion. For example, when the user puts the electronic device 101 on his wrist and then runs a TV/game console, the electronic device 101 can determine that the user uses the electronic device 101 for control purposes. Accordingly, the electronic device 101 can provide a notification user interface, e.g., saying "Please relocate to the forearm for accurate EMG control."

FIGS. 6A to 6F are a front and rear view illustrating an electronic device according to an embodiment of the present disclosure.

Figure 6A:
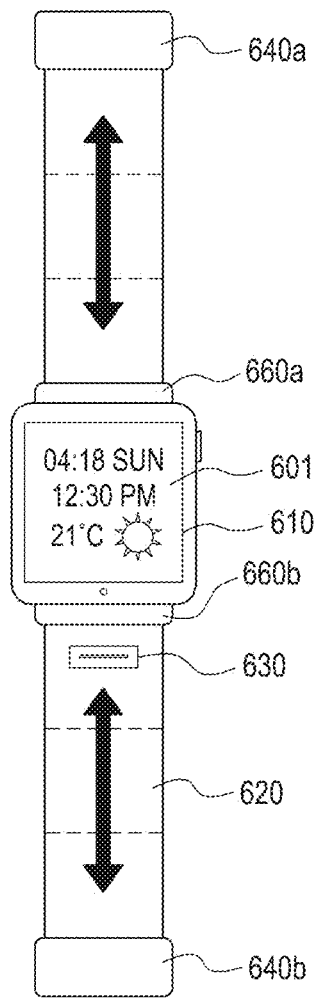
Figure 6B:
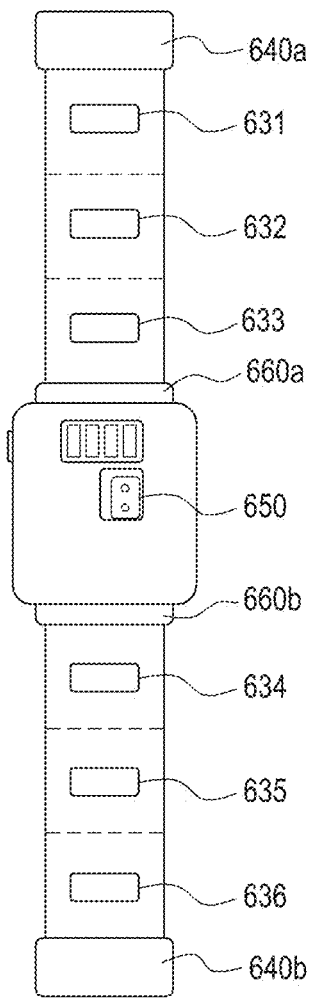

Referring to FIG. 6A, the electronic device can include a display 610, a strap 620, an external facing sensor 630, couplers 640a and 640b, and actuators 660a and 660b.

The display 610 can display a first screen 610. In the embodiment illustrated in FIG. 6a, the first screen 610 includes date, time, and weather information. However, this is merely an example. It will be readily appreciated by one of ordinary skill in the art that the display 610 can display a result of monitoring the user's health information, electronic device control screen, or menu screen, without limited thereto. The display 610 can be implemented in a normal liquid crystal display (LCD), a light emitting diode (LED)-type or flexible-type LCD, or electronic paper display.

The strap 620 can be connected to the display 610. In an embodiment, the strap 620 can also be connected to the actuators 660a and 660b. The actuators 660a and 660b can include a motor device for adjusting the length of the strap 620. For example, a portion of the strap 620 can be positioned inside the housing and the rest can be exposed externally. The actuators 660a and 660b can adjust the length of the strap 620 by adjusting the portion externally exposed. The strap 620 can include an elastomer for tightly putting on the user.

The external facing sensor 630 can be disposed on the front surface of the electronic device and can sense the user's touch. The external facing sensor 630 can be implemented with, e.g., a pressure sensor, optical sensor, and electrodes, and can recognize the user's touch, ECG signals, or fingerprints.

The couplers 640A and 640B can include physical structures that can fit or couple together. Or, the couplers 640a and 640b can include a hall integrated chip (IC) for determining whether they couple or not. Although not shown, the electronic device can further include a vibration motor, an embedded sensor for detecting motion, or a speaker.

Internal facing sensors 631 to 636 and 650 can be provided on the rear surface of the electronic device. The internal facing sensors 631 to 636 can be implemented with, e.g., a pressure sensor, optical sensor, and electrodes, and can recognize the user's touch, ECG signals, or fingerprints. In an embodiment, the internal facing sensor 650 can be implemented in an optical sensor. The internal facing sensor 650 can include an HRM sensor, a blood pressure (BP) sensor, a glucose sensor, a body temperature sensor, a vein sensor, or a bio-marker sensor.

FIG. 6C illustrates an example of adjusting the length of the strap 620 according to an embodiment of the present disclosure. As shown in FIG. 6c, the actuators 660a and 660b can adjust the length of the strap 620 by adjusting the portion externally exposed.

FIGS. 6D to 6F illustrate examples in which an electronic device is implemented in various types according to embodiments of the present disclosure.

As shown in FIG. 6D, the electronic device 101 can be implemented as clothes wearable on the user. The electronic device 101 can include a piece 670 of clothing and at least one sensor 671 to 675. The at least one sensor 671 to 675 can be disposed at a position indicating relative coordinates on the body.

As shown in FIGS. 6E and 6F, the electronic device 101 can be implemented in the form of a ring 690 wearable on the user's finger.

Figure 7:
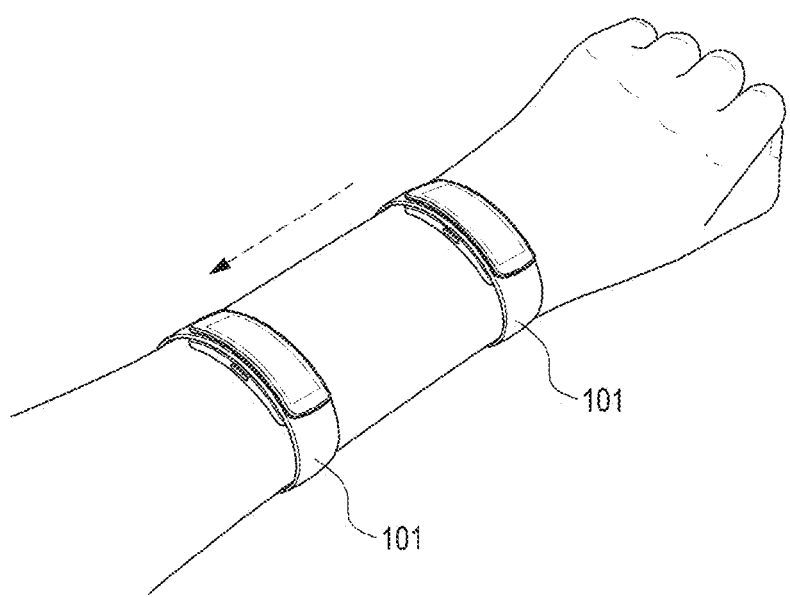
FIG. 7 illustrates a change in an area where an electronic device is worn according to an embodiment of the present disclosure.

FIG. 7 illustrates a change in an area where an electronic device is worn according to an embodiment of the present disclosure. As shown in FIG. 7, the electronic device 101 worn on the user's wrist can shift to the user's forearm. The electronic device 101 can tightly contact the user's wrist or forearm through adjustment of the length of the strap 620. In this case, the electronic device 101 can obtain the worn portion or change in the worn portion based on the length of the strap 620 and can change the mode determination signal or operation mode.

Figure 8:
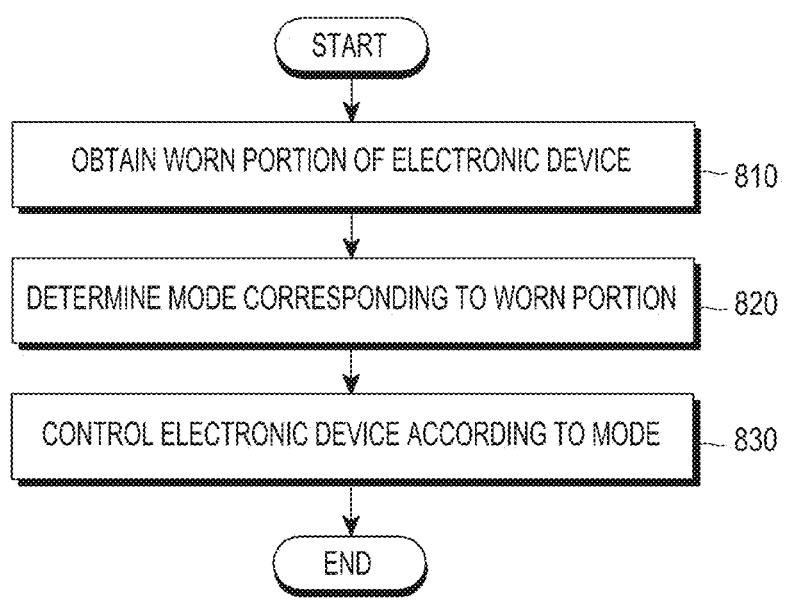
FIG. 8 is a flowchart illustrating a method for controlling an electronic device according to an embodiment of the present disclosure.
Figure 9:
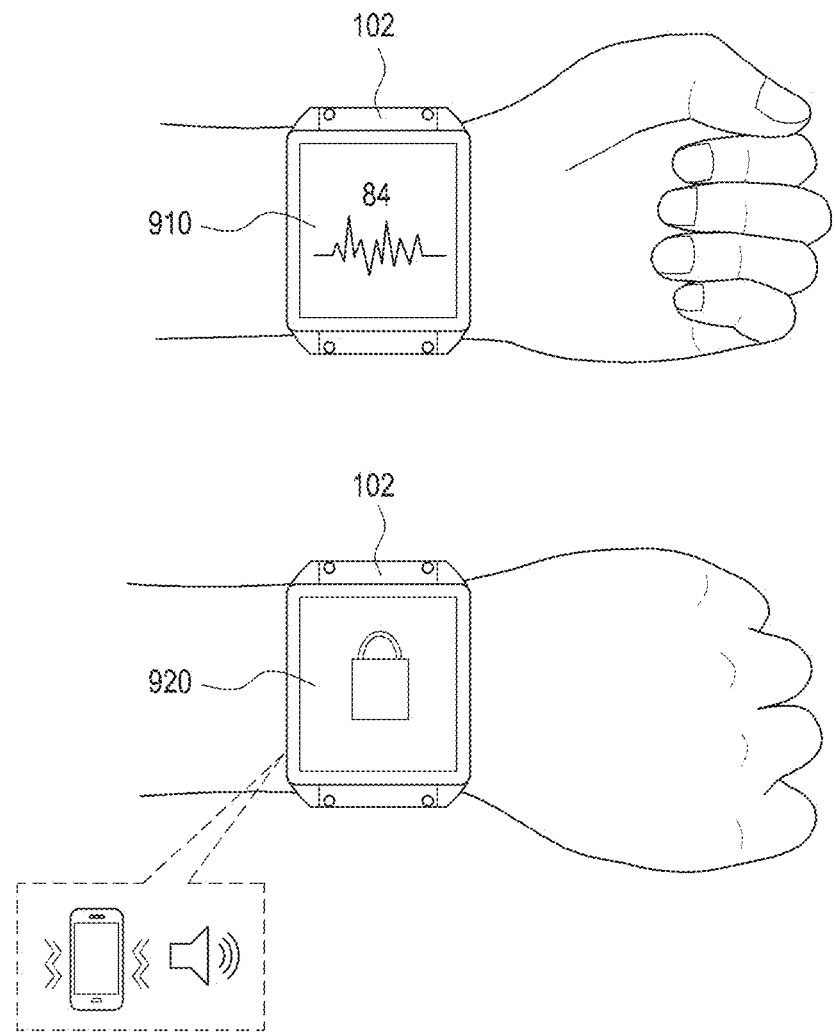
FIG. 9 illustrates a state in which an electronic device is worn according to an embodiment of the present disclosure.

FIG. 8 is a flowchart illustrating a method for controlling an electronic device according to an embodiment of the present disclosure. The embodiment shown in FIG. 8 is described in greater detail with reference to FIG. 9. FIG. 9 illustrates a state in which an electronic device is worn according to an embodiment of the present disclosure.

As shown in FIG. 8, the electronic device 101 can obtain the worn portion of the electronic device 101 in operation 810. According to an embodiment of the present disclosure, the electronic device 101 can obtain a direction that the electronic device 101 is worn. For example, the electronic device 101 can obtain the direction that the electronic device 101 is worn based on data from at least one of, e.g., a gyro sensor, a geo-magnetic sensor, a slope sensor, and a gravity sensor.

For example, as shown in FIG. 9, the electronic device 101 can be worn to be positioned at inner side of the user's wrist. Specifically, the electronic device 101 can be worn so that the display of the electronic device 101 is positioned on the user's wrist extending from the palm. Alternatively, as shown in FIG. 9, the electronic device 101 can be worn to be positioned at outer side of the user's wrist. Specifically, the electronic device 101 can be worn so that the display of the electronic device 101 is positioned on the user's wrist extending from the back of the hand. The electronic device 101 can determine whether the electronic device 101 is worn on the inner side of the user's wrist or outer side of the user's wrist.

In operation 820, the electronic device 101 can determine a corresponding operation mode based on at least one of the portion and direction where the electronic device is worn. In an embodiment, when the electronic device is determined to be worn at outer side of the wrist, the electronic device 101 can set a security mode to the operation mode. As shown in FIG. 9, in the security mode, the electronic device 101 can output a vibration or alert sound corresponding to an event while displaying a security screen 920 that does not display the event. When the electronic device 101 is worn on the top of the wrist, it is more likely for others than the user to look at the screen of the electronic device 101. Particularly, when private information, such as the result of monitoring heath information, is displayed on the electronic device 101, a security issue can become severe. According to an embodiment of the present disclosure, when the electronic device 101 is worn at the outer side of the wrist, the electronic device 101 can operate in a security mode, addressing the security issue. On the other hand, when the electronic device 101 is worn at the inner side of the wrist, it is relatively less likely for others than the user to look at the screen of the electronic device 101. According to an embodiment of the present disclosure, when the electronic device 101 is worn on the bottom of the wrist, the electronic device 101 can operate in a normal mode while displaying a running screen 910 for an application being executed as shown in FIG. 9. When the electronic device 101 outputs a vibration or alert sound corresponding to the occurrence of an event, the user can change the direction that the electronic device 101 is worn in order to identify the same. The electronic device 101 can detect the change in the direction worn and can make a switch from the security mode to the normal mode corresponding to the same to display a screen 910.

Figure 10:
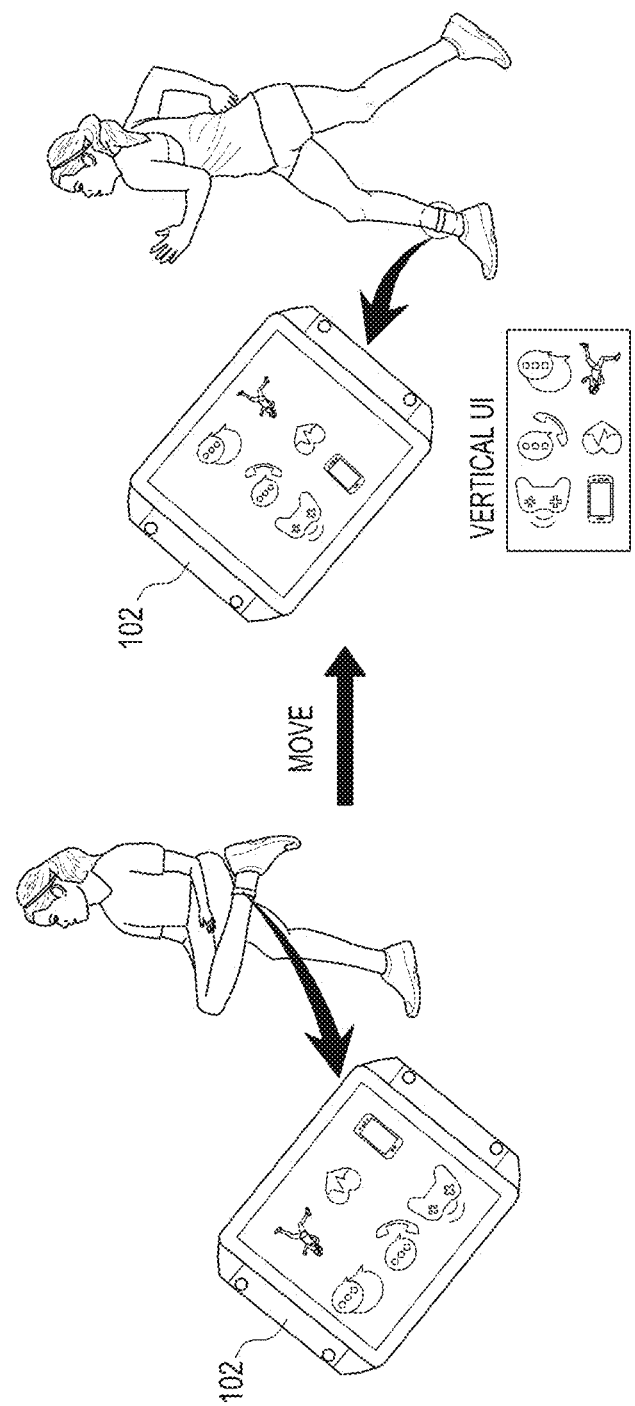
FIG. 10 illustrates a change in a screen configuration according to a change in a direction where an electronic device is worn according to an embodiment of the present disclosure.

FIG. 10 illustrates a change in a screen configuration according to a change in a direction where an electronic device is worn according to an embodiment of the present disclosure.

As shown in FIG. 10, the electronic device 101 can be worn on the user's right ankle. The user can place his right leg on the left knee with the electronic device 101 worn on the right ankle. In this case, the display of the electronic device 101 can be disposed in a first direction with respect to the user. The electronic device 101 can obtain the information indicating that the worn portion is the right ankle. The electronic device 101 can obtain the information indicating direction that the electronic device 101 is worn, i.e. the first direction. Corresponding to this, the electronic device 101 can display a user interface (UI) in a horizontal direction.

Meanwhile, the user can put his right leg ahead of the left leg while putting the electronic device 101 on the right ankle as shown in FIG. 10. In this case, the display of the electronic device 101 can be disposed in a second direction with respect to the user. The electronic device 101 can obtain the information indicating that the worn portion is the right ankle. The electronic device 101 can obtain the information indicating direction that the electronic device 101 is worn, i.e. the second direction. Corresponding to this, the electronic device 101 can display a user interface (UI) in a vertical direction.

According to an embodiment of the present disclosure, corresponding to the worn portion being the ankle, the electronic device 101 can enlarge the objects included in the user interface as compared with when the worn portion is a wrist. The electronic device 101 can adjust the size of an object considering the distance between the worn portion and the user's eye, and this is described below in greater detail.

According to an embodiment of the present disclosure, the electronic device 101 can provide a user interface different from that when the worn portion is a wrist, corresponding to the worn portion being the ankle. When the worn portion is the ankle, the user can feel less comfortable in manipulation of the electronic device 101 as compared with when the electronic device 101 is worn on a wrist. Accordingly, the electronic device 101 can display a user interface simplified for easier manipulation. The user interface simplified for easier manipulation can be constituted of fewer objects than those of the basic user interface, and the size of the objects configuring the user interface can be larger than that of the objects configuring the basic user interface.

According to an embodiment of the present disclosure, the electronic device 101 can perform control to operate in a sports mode appropriate for the worn portion, corresponding to the worn portion being the ankle. Among sports enjoyed by the user are sports played primarily using the user's arms, such as tennis, table tennis, or golf and sports played relatively using the user's legs such as jogging or biking. When a user enjoying golf desires to analyze his swing motion or trajectory, the user can put the wearable device on his wrist, and a user jogging or running the marathon can put the wearable device on his leg rather than his wrist. In this case, the sports mode of the wearable device can be varied considering the position where the user wears the wearable device. When the user runs the marathon while putting the wearable device on this wrist or playing golf while putting the wearable device on his ankle, a portion proper to be worn can be recommended.

Figure 11A:
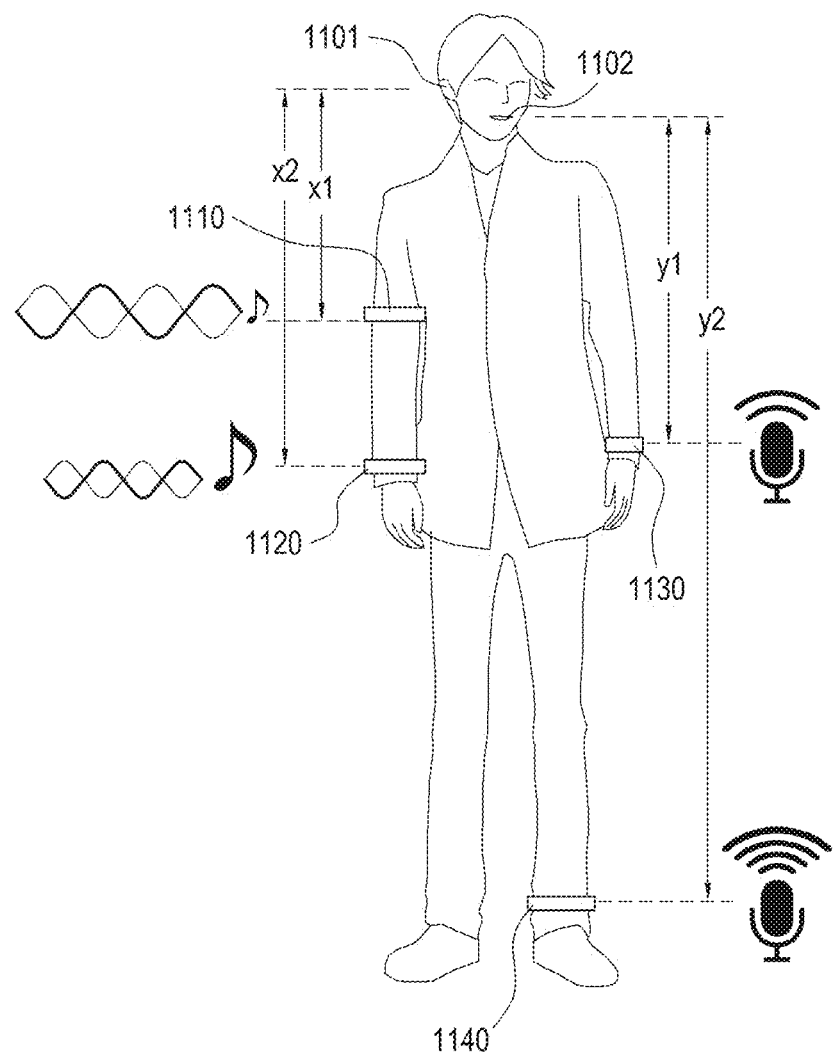
FIGS. 11A and 11B illustrate controls according to areas where an electronic device is worn according to embodiments of the present disclosure.
Figure 11B:
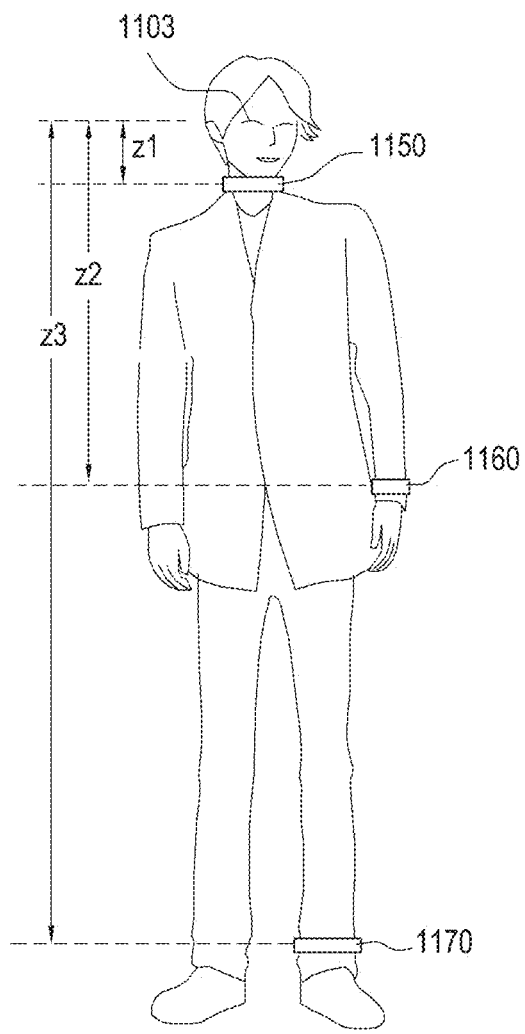

FIGS. 11A and 11B illustrate controls according to areas where an electronic device is worn according to embodiments of the present disclosure.

Referring to FIG. 11A, the electronic device 101 can obtain the information indicating that the worn portion is a right elbow 1110, right wrist 1120, left wrist 1130, or left ankle 1140. As set forth above, the electronic device 101 can obtain the worn portion based on at least one of the length of the strap, a bio signal obtained, altitude data sensed, geo-magnetic data sensed, and slope data sensed.

The electronic device 101 can control the electronic device 101 based on the distance between the obtained worn area and a predetermined body portion of the user. For example, it can be assumed that the worn portion of the electronic device 101 is the right elbow 1110. The electronic device 101 can determine that the distance between the predetermined body portion of the user, e.g., the user's ear 1101, and the right elbow 1110 is x1. For example, it can be assumed that the worn portion of the electronic device 101 is the right wrist 1120. The electronic device 101 can determine that the distance between the predetermined body portion of the user, e.g., the user's ear 1101, and the right wrist 1120 is x2. The electronic device 101 can determine the volume of an output sound from the electronic device 101 based on the distance between the worn portion and the predetermined body portion. For example, when the electronic device 101 is worn relatively closer to the user's ear 1101, the electronic device 101 can output a relatively smaller volume of sound. When the electronic device 101 is worn relatively farther from the user's ear 1101, the electronic device 101 can output a relatively larger volume of sound.

In another embodiment, it can be assumed that the worn portion of the electronic device 101 is the left wrist 1130. The electronic device 101 can determine that the distance between the predetermined body portion of the user, e.g., the user's mouth 1102, and the left wrist 1130 is y1. For example, it can be assumed that the worn portion of the electronic device 101 is the left ankle 1140. The electronic device 101 can determine that the distance between the predetermined body portion of the user, e.g., the user's mouth 1102, and the left ankle 1140 is y2. The electronic device 101 can determine the microphone sensitivity of the electronic device 101 based on the distance between the worn portion and the predetermined body portion. For example, when the electronic device 101 is worn relatively closer to the user's mouth 1102, the electronic device 101 can set the microphone sensitivity to be relatively smaller. For example, when the electronic device 101 is worn relatively farther from the user's mouth 1102, the electronic device 101 can set the microphone sensitivity to be relatively larger.

Referring to FIG. 11B, the electronic device 101 can obtain the information indicating that the worn portion is the neck 1150, left wrist 1160, or left ankle 1170. The electronic device 101 can determine that the distance between a predetermined body portion of the user, e.g., the user's eye 1103, and the neck 1150, the distance between the eye 1103 and the left wrist 1160, and the distance between the eye 1103 and the left ankle 1170 are z1, z2, and z3, respectively. The electronic device 101 can determine the screen resolution of the electronic device 101 based on the distance between the worn portion and the predetermined body portion. For example, when the electronic device 101 is worn relatively closer to the user's eye 1103, the electronic device 101 can display objects configuring the screen to be relatively smaller. For example, when the electronic device 101 is worn relatively farther from the user's eye 1103, the electronic device 101 can display objects configuring the screen to be relatively larger.

Meanwhile, according to an embodiment of the present disclosure, the strength of a vibration can be determined according to the worn portion. For example, when the electronic device is worn on a portion more sensitive to a vibration, the electronic device 101 can determine that the strength of vibration is relatively smaller. For example, when the electronic device is worn on a portion less sensitive to a vibration, the electronic device 101 can determine that the strength of vibration is relatively larger.

According to an embodiment of the present disclosure, the electronic device 101 can determine the resolution, volume of output sound, microphone sensitivity, or strength of vibration. In another embodiment, the electronic device 101 can previously store the worn portion and a resolution, output sound volume, microphone sensitivity, and vibration strength corresponding to the worn portion. Meanwhile, the previously stored values can be updated. For example, the user can listen a preset volume of sound from the electronic device 101 and can readjust the same. The electronic device 101 can update the set value to a value readjusted by the user to manage the same. Accordingly, set values for the electronic device 101 can vary depending on each user.

Figure 12:
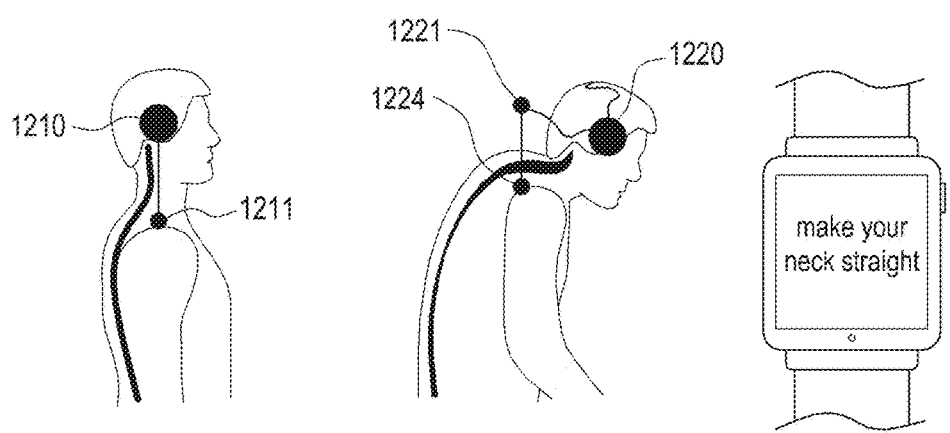
FIG. 12 is a concept view illustrating a screen configuration of an electronic device according to an embodiment of the present disclosure.

FIG. 12 is a concept view illustrating a screen configuration of an electronic device according to an embodiment of the present disclosure. In the embodiment shown in FIG. 12, the electronic device 101 can be worn on the user's neck. The electronic device 101 can determine whether the user's neck is positioned properly by measuring an EMG signal from a plurality of portions of the user's neck. For example, as shown in FIG. 12, the position at which the user's head 1210 and shoulder 1211 are perpendicular to the ground can be proper. As shown in the middle of FIG. 12, as the difference between a position 1221 and shoulder 1224 increases, the user's position can be away from a proper one. Also, the difference between the position 1221 and head 1220 increases, the user's position can be away from a proper one. The electronic device 101 can determine whether the user takes a proper position based on an obtained EMG signal, and when the user is determined not to take a proper position, the electronic device 101 can display a user interface to guide the user to a proper position. For example, the electronic device 101 can display the user interface to guide the user to a proper position according to whether the obtained EMG signal is identical or similar to a predetermined EMG signal.

FIG. 13 is a concept view illustrating an electronic device according to an embodiment of the present disclosure.

Figure 13A:
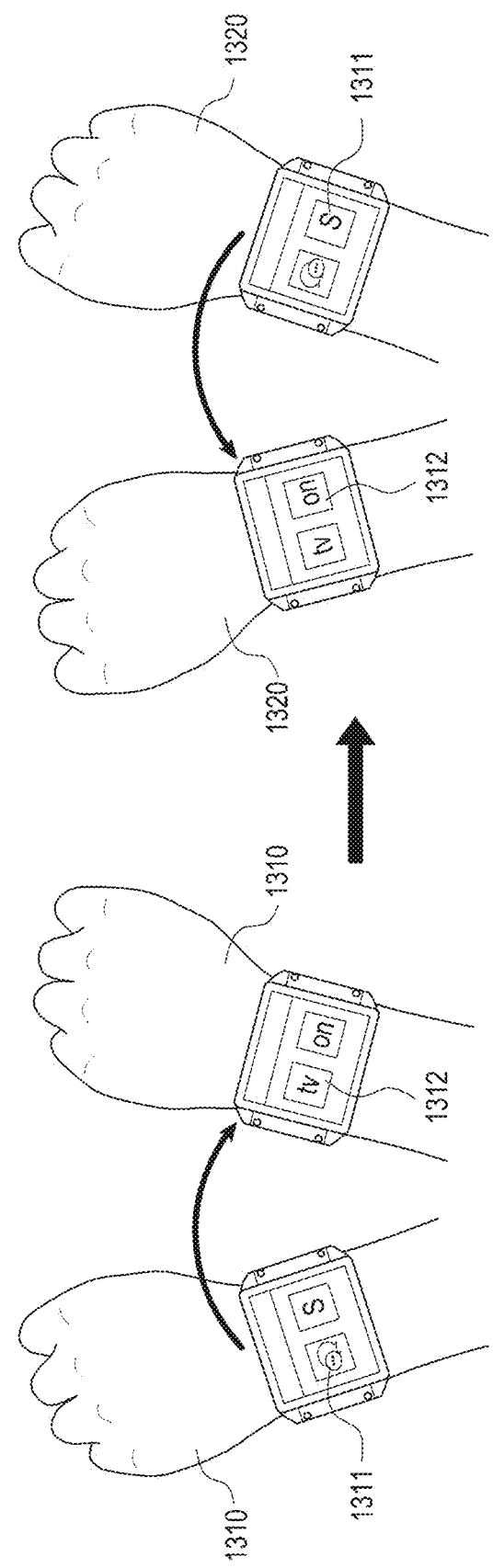
FIG. 13A is a concept view illustrating an electronic device according to an embodiment of the present disclosure.

Referring to FIG. 13A, the electronic device 101 can be worn on the user's left hand 1310 or right hand 1320. The electronic device 101 can determine whether the worn portion is the user's left hand 1310 or right hand 1320. A configuration for determining that the worn portion of the electronic device 101 is the left hand 1310 or right hand 1320 is described below in further detail.

Meanwhile, the electronic device 101 can sense a movement of the electronic device 101. For example, the electronic device 101 can include a gyro sensor or acceleration sensor, and thus, the electronic device 101 can sense movement information regarding the electronic device 101. The electronic device 101 can output a predetermined function corresponding to the movement. That is, the electronic device 101 can store a movement command and the predetermined function, with the movement command corresponding to the function. For example, as shown on the left side of FIG. 13A, upon detecting a movement in a first direction, the electronic device 101 can replace a first screen 1311 with a second screen 1312 and display the second screen 1312.

Meanwhile, the electronic device 101 can detect a change in the worn portion from the left hand 1310 to the right hand 1320. The electronic device 101 can vary the direction of the movement command corresponding to the change in the worn portion. For example, as shown on the right side of FIG. 13A, the electronic device 101 can change a movement command in the first direction into a movement command in a second direction. Upon detecting a movement in the second direction, the electronic device 101 can replace the first screen 1311 with the second screen 1312 and display the second screen 1312. That is, the electronic device 101 can determine the direction of a gesture command depending on whether the electronic device 101 is worn on the left hand or right hand. When the electronic device 101 is worn on the left hand, the electronic device 101 can determine that the direction of a first gesture for performing a first task is a first direction, and when the first gesture in the first direction is input, the electronic device 101 can perform the first task. When the electronic device 101 is worn on the right hand, the electronic device 101 can determine that the direction of the first gesture for performing the first task is a second direction, and when the first gesture in the second direction is input, the electronic device 101 can perform the first task.

Figure 13B:
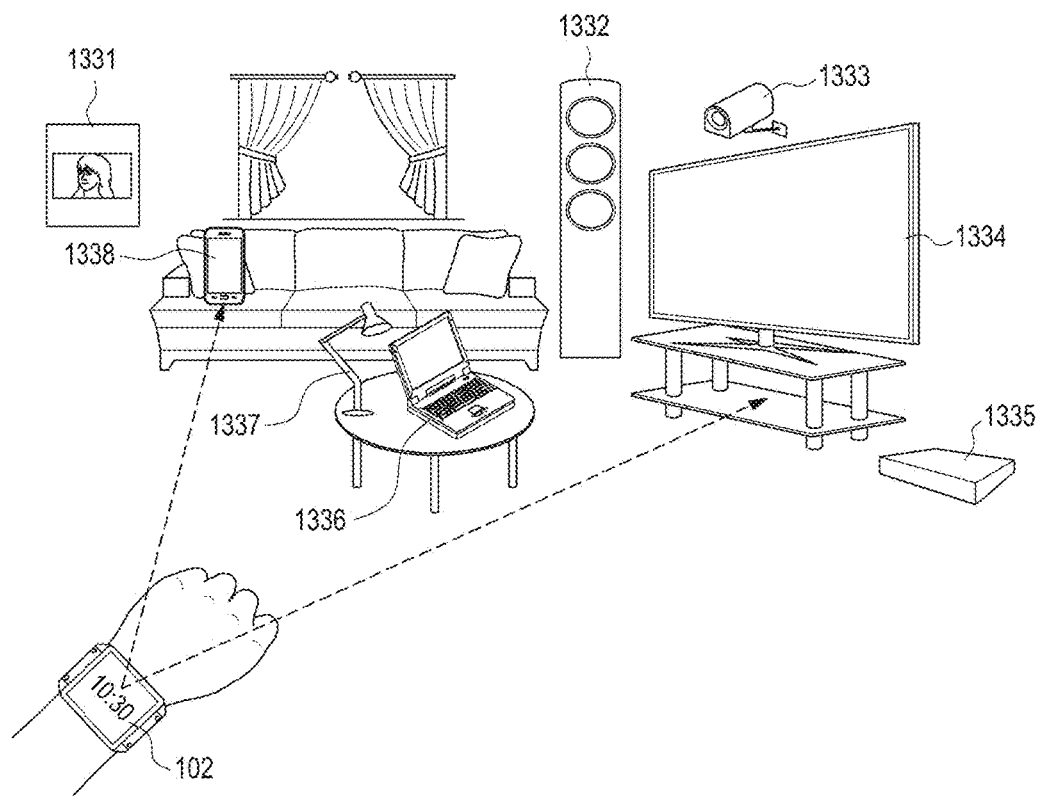
FIG. 13B illustrates a home network control according to an embodiment of the present disclosure.

FIG. 13B illustrates a home network control according to an embodiment of the present disclosure.

As shown in FIG. 13B, the electronic device 101 can be connected with various electronic devices 1331 to 1338 in the home network directly or via a control point. The electronic device 101 can enter into the control mode and can send out control commands for other electronic devices 1331 to 1338 based on a user input received in the control mode. For example, the electronic device 101 can transmit a control command based on a bio signal, such as an electromyogram signal received from a muscle. Or, the electronic device 101 can transmit a control signal based on movement information. In another embodiment, upon determining that there are other controllable electronic devices, the electronic device 101 can switch from the control mode to another mode. The electronic device 101 can set a controllable range. The controllable range can be set by the user or can be determined by a communication protocol as used.

The control point of the home network can grasp the position to which the user wearing the electronic device 101 has moved through a camera included in the various electronic devices and can enable a nearby electronic device to enter into the control mode. The control point of the home network, upon recognizing one or more electronic devices supporting the control mode in the controllable range, can compare a user pattern previously registered in the database with the user's current position or movement pattern and can then prioritize a corresponding electronic device to connect and control the same.

The user pattern can be configured based on the user's movement recognized through a motion sensor and the user's bio signal figured through the EMG sensor and can be differentiated in more detail utilizing location information and time information. For example, when the user putting the electronic device 101 on his right arm normally adjusts the TV volume in a particular place, e.g., a living room, by making the palm face up or down, such pattern can be stored in the database, and when such user pattern is sensed, the electronic device 101 can turn into the control mode to control the TV 1334.

There can be such situation that there are a number of electronic devices supporting a similar function around the user wearing the electronic device 101. In this case, when user patterns to control the several electronic devices are similar to one another, only recognition of the user's motion might not differentiate the user's desired electronic device from the others and automatically connect to the same. In such case, thus, the control point can send out notifications to all of the controllable electronic devices so that they enter into a standby mode and can analyze additional user patterns entered thereafter to grasp whether the patterns are ones corresponding to the respective electronic devices so that a connection can be made to an electronic device with the highest correlation.

In such case, as another method for differentiating an electronic device controlled by the control point, when the user's view is recognized through a camera sensor equipped in at least one electronic device, and the electronic device is determined to be the electronic device desired to be controlled by the user, view recognition information can be transferred to the electronic device 101, and the electronic device 101 can determine another electronic device for connection and connect to the same by combining the user pattern with the user view recognition information.

Another method for differentiating an electronic device for control by the electronic device 101 uses an integrated camera sensor 1333 installed to identify the position of several electronic devices present in a particular place, e.g., a living room, and the user's position and motion. The integrated camera sensor 1333 can sense the user's position and motion and can provide the electronic device 101 with information on correlations with other several electronic devices located in the particular place. Malfunctions can be reduced by compiling the correlation information with the electronic devices and the user sensed through the integrated camera sensor 1333 as well as position and time information and user patterns input to the electronic device 101, thus leading to more accurate control of the other electronic devices.

The integrated camera sensor 1333 can also grasp a view of the user wearing the wearable device as well as the user's position and motion. Thus, the electronic device 101 can also sense correlations with other electronic devices controllable through the user's view.

A representative device requiring the user's view for control is a TV. When the user wearing the electronic device 101 is positioned in front of the device or within a predetermined range for the device after the device is turned on, it can enter into the control mode. A game console can also enter into the control mode to control the game when the user wearing the electronic device 101 is positioned in front of the game console, and when desiring to pause the game in the middle or to perform another control, the user can issue a command through a touch on the display, voice input, or the user's movement sensible by the wearable device. The camera of the device can sense the user's approach and can perform control through, e.g., the operation of passing before the device, the operation of stopping facing the device, or various input operations with the view facing the device.

As described above, a change in the input scheme mode can be made depending on whether the electronic device 101 is worn while controlling in the control mode. When the electronic device 101 is worn, a controlled electronic device can use a value inputted through the electronic device 101 as a control signal, and when the electronic device 101 is determined not to be worn, the user's gesture can be rendered to be sensed through the camera of the multimedia device being controlled, rather than an input through the wearable device, to be able to receive the same.

Figure 14A:
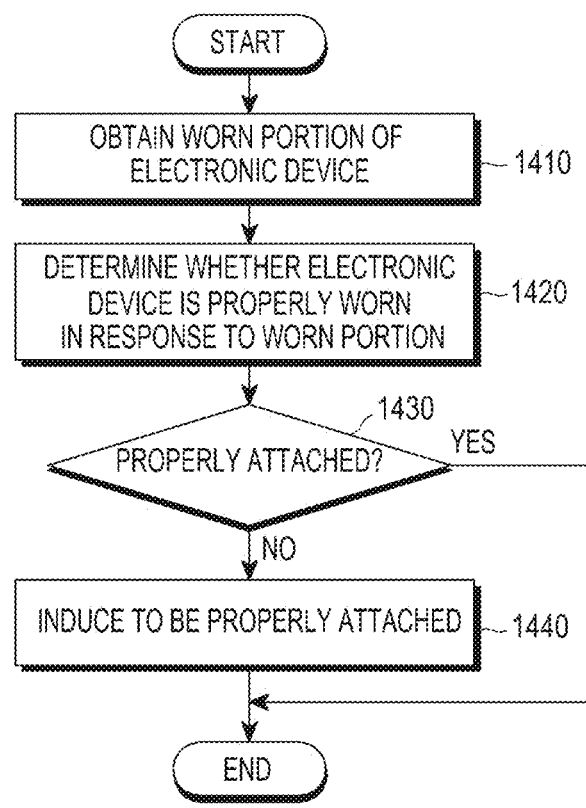
FIG. 14A is a flowchart illustrating a method for controlling an electronic device according to an embodiment of the present disclosure.
Figure 14B:
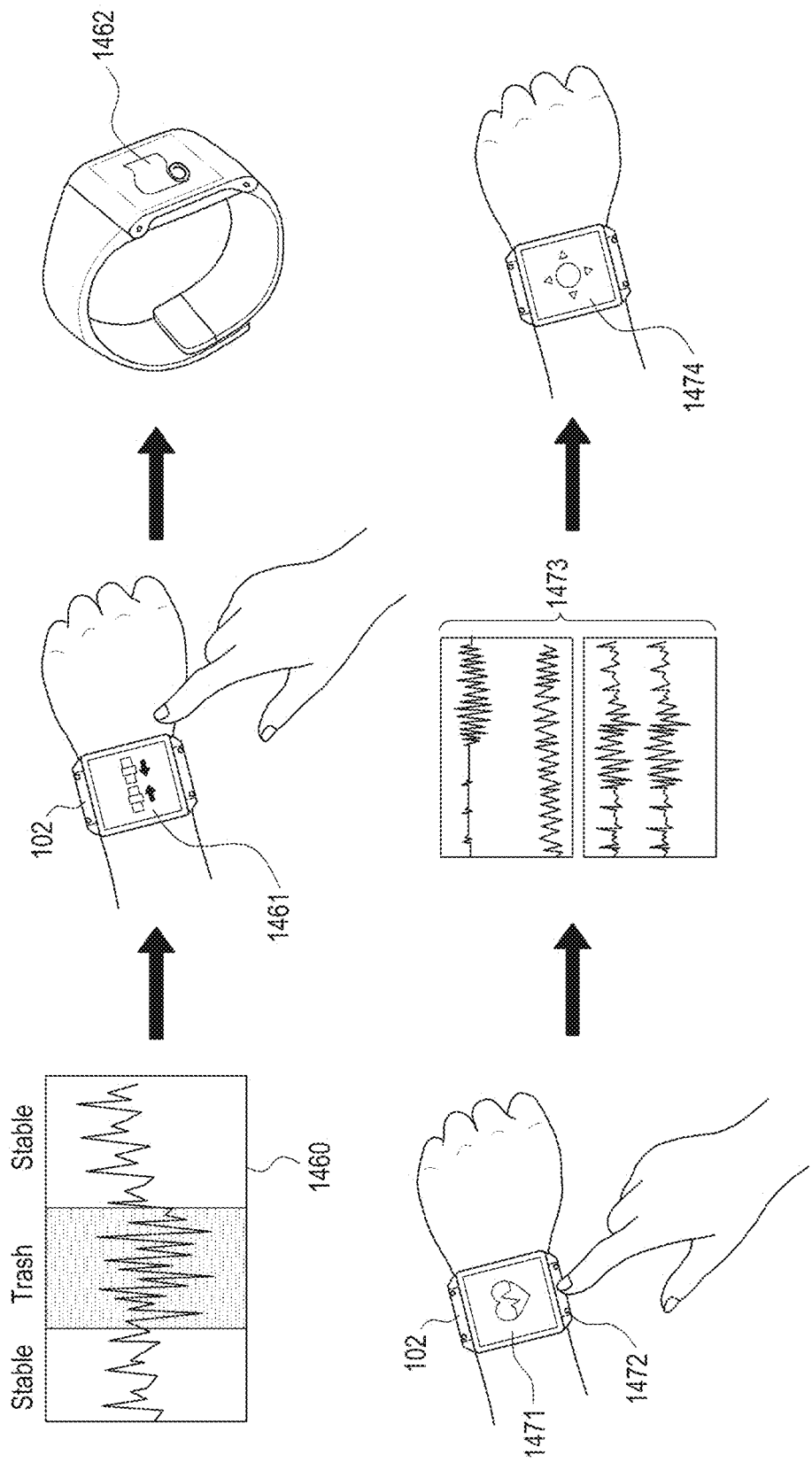
FIGS. 14B and 14C are concept views illustrating an electronic device according to embodiments of the present disclosure.

FIG. 14A is a flowchart illustrating a method for controlling an electronic device according to an embodiment of the present disclosure. The embodiment of FIG. 14B is described in further detail with reference to FIGS. 14B and 14C.

In operation 1410, the electronic device 101 can obtain the area where the electronic device 101 is worn. As shown in FIG. 14B, the electronic device 101 can be worn on the user's wrist. The electronic device 101 can include an actuator 1472 for adjusting the length of the strap. The electronic device 101 can include a sensor that can sense the user's ECG signal 1460 and can run and display a health information monitoring application 1471 based on the sensed ECG signal. The electronic device 101 can output a result 1473 of health information monitoring.

In operation 1420, the electronic device 101 can determine whether the electronic device 101 is properly attached to the worn portion of the user's body.

In an embodiment, the electronic device 101 can determine whether the electronic device 101 is properly worn based on a detected bio signal. As described above, the electronic device 101 can determine whether the electronic device 101 is properly worn based on a noise signal (Trash) included in the ECG signal 1460. When the magnitude of the noise signal is larger than a threshold, the electronic device 101 can determine that the electronic device 101 is improperly worn. The electronic device 101 can previously store the threshold for determining whether the electronic device is properly worn corresponding to the worn portion. Here, "the electronic device 101 is properly worn" can mean that the electronic device 101 is worn in tight contact with the user. In such case, the electronic device 101 can determine a degree of tight contact to indicate whether the electronic device 101 tightly contacts the user.

Figure 14C:
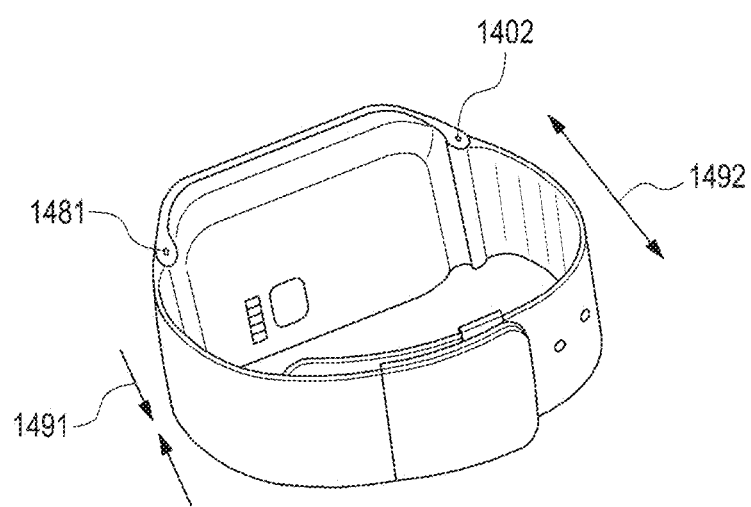

When the electronic device 101 is not determined to be properly worn in operation 1430, the electronic device 101 can operate to lead to the proper wearing of the electronic device 101. In an embodiment, as shown in FIG. 14B, the electronic device 101 can display a user interface 1461 to adjust the length of the strap. When the user inputs a length adjustment command through the user interface 1461, the electronic device 101 can display adjustment information 1462 while adjusting (1491 and 1492) the length of the strap as shown in FIG. 14C. On the other hand, unless a length adjustment command is input from the user, the electronic device 101 can disregard data from a sensor sensing noise exceeding a threshold while monitoring the user's health information only with data from the remaining sensors according to an embodiment of the present disclosure. Further, the electronic device 101 can report, e.g., information regarding selection of a proper sensor to the user and can reflect the same to a user health information database. In an embodiment, when detecting a predetermined behavior that causes the user to feel uncomfortable, like the strap is too tight, the electronic device 101 can lengthen the strap than before. For example, the electronic device 101 can be configured to lengthen the strap corresponding to a behavior by which the electronic device 101 moves left and right several times.

In an embodiment, the electronic device 101 can analyze the health information monitoring result 1473. The electronic device 101 can determine whether another bio signal is required to be measured based on the health information monitoring result 1473. The electronic device 101 can output a user interface to induce the electronic device 101 to shift to a worn portion where the other bio signal is measured. According to an embodiment of the present disclosure, the electronic device 101 can also output the user interface 1474 to induce the shift to the corresponding worn portion based on an input of voice corresponding to predetermined text, such as complaining of chest pains, from the user or the user's behavior of tapping his chest, as well as the health information monitoring result 1473. According to an embodiment of the present disclosure, the electronic device 101 can display in real-time a proper shifting direction of the electronic device 101. Accordingly, the electronic device 101 can vary and display the proper shifting direction of the electronic device 101 so that the user shifts the electronic device 101 to a proper worn portion.

According to an embodiment of the present disclosure, the electronic device 101 can compensate for noise due to the user's sweat. When the user wears the electronic device 101 long time with the electronic device 101 tightly contacting the skin, the contacting portion can be sharply heated up or sweat due to the external temperature or heat generated from the electronic device 101 itself, causing malfunctions when measuring bio signals. Thus, when the user's skin heats up or sweats due to continuous use of the electronic device 101 with the electronic device 101 tightly contacting the skin, the electronic device 101 can identify the varied temperature and humidity, and when they approach a level at which bio signals can be erroneously measured, the electronic device 101 can generate an alert. The varied temperature and humidity can be determined through the temperature and humidity sensor of the electronic device 101 and through changes in values measured by the bio signal sensor. The electronic device 101 can categorize the degree of sweating measured by the temperature and humidity sensor into an unable-to-measure-biosignal level and an able-to-measure-biosignal level and can alert at the unable-to-measure-biosignal level. When the bio signal sensor is an optical sensor, light radiated from a light emitter, while passing through the user's skin, can be partially absorbed by the skin and partially reflected to a light receiver to measure the level. The electronic device 101 can store, as a reference value, a degree by which the sweat on the skin affects the absorption/reflection of the light, and when a similar resultant value as output is off a reliable range for sensor measurement, the electronic device 101 can let this known. When the bio signal sensor is an electrical (contact-type) sensor, the electronic device 101 can store, as a reference value, a change in conductance ratio between the electrode and the skin due to sweat, and when a similar resultant value as output is off a reliable range, the electronic device 101 can let this known.

Figure 15A:
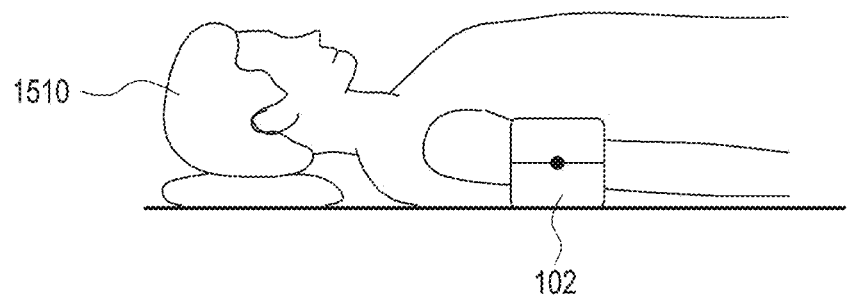
FIGS. 15A to 15C illustrate an example of inducing an electronic device to be properly worn according to an embodiment of the present disclosure.
Figure 15B:
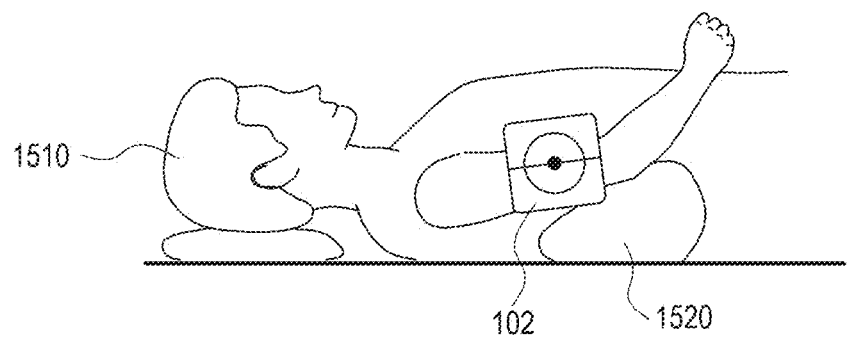
Figure 15C:
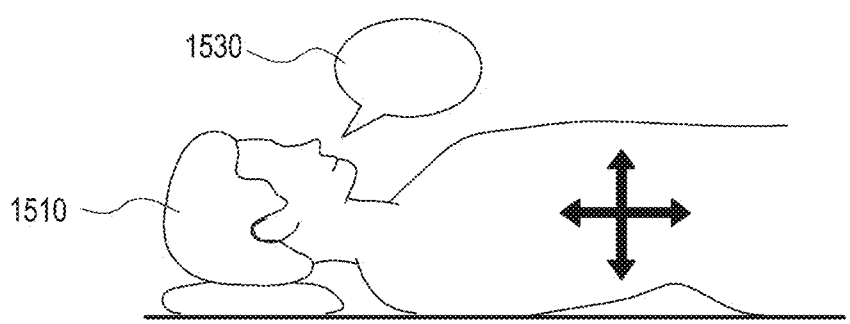

FIGS. 15A to 15C illustrate an example of inducing an electronic device to be properly worn according to an embodiment of the present disclosure. FIGS. 15A to 15C can relate to an example of measuring blood pressure by the electronic device 101.

As shown in FIG. 15A, the user 1510 can put the electronic device 101 on his right arm while lying. The electronic device 101 can include a sensor to measure the blood pressure of the user 1510. The blood pressure can frequently vary under the influence of body conditions (food, alcohol, smoke, posture, pains, stress, or mood) and can differ depending on time and place measured or activities. Systolic (maximum) blood pressure frequently fluctuates and shows a tendency of ascending while awakened (during a bodily or emotional activity) and descending in a dormant state (while relaxing or sleeping). The systolic blood pressure of a human being steadily rises over three hours or more while his body goes in activity right after he wakes up. A daily fluctuation of blood pressure can be about 20 mmHg to about 30 mmHg. When a user is measured for his blood pressure, he needs to be in a stable condition for accurate measurement. The electronic device 101, when entering into a blood pressure measurement mode, can output a user interface to induce the user to wear the electronic device 101 in a proper position to measure the blood pressure.

Figure 16A:
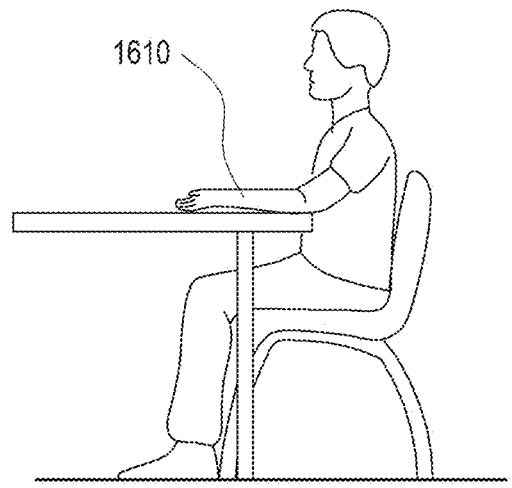
FIGS. 16A and 16B illustrate an example of inducing an electronic device to be properly worn according to an embodiment of the present disclosure.
Figure 16B:
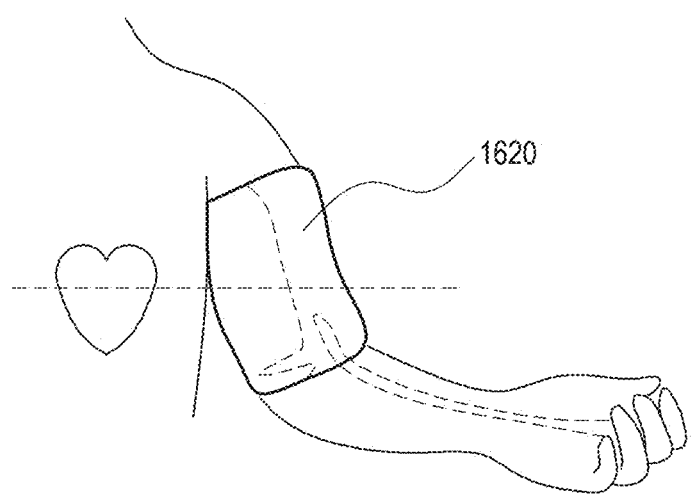

For example, the following is a recommended blood pressure measuring method. To determine whether the user's blood pressure is abnormal, the blood pressure can be repeatedly measured twice a day, morning and evening, for seven days, and 12 of the 14 measurements are averaged while the other two are excluded. In this case, the measured blood pressure being 135/85 mmHg or more can be determined as a high blood pressure, and such measurement method can be as accurate as a 24-hour measurement method. Accordingly, the user can take five minutes of relaxation before measurement to put his body in a stabilized condition. Upon measurement on the user's arm, the user can remain lying or lean his back against a chair while placing his arm 1610 near his heart with a measurer 1620 wrapped around the arm as shown in FIGS. 16A and 16B. For a user who has done workout, one to two hours of rest can be required. When the blood pressure measurement mode runs corresponding thereto, the electronic device 101 can output a user interface inquiring whether he took a rest five minutes or more, one to two hours when he has done workout.

According to an embodiment of the present disclosure, the electronic device 101 can measure blood pressure on both arms, and in this case, data with a higher blood pressure among measurements can be selected.

Meanwhile, upon measurement of blood pressure, the user needs to abstain from sitting his legs or arms crossed or the worn portion needs to be avoided from pressurized. Thus, the electronic device 101 can output a voice or user interface to induce the user to take a proper position as described above. Further, the measurement of blood pressure needs to be done at room temperature. The electronic device 101 can include a module able to measure temperature or receive temperature information from a temperature measurement module. When the current temperature is determined not to be included in a predetermined range based on the obtained temperature information, the electronic device 101 can output a user interface indicating that the temperature is not proper for measurement of blood pressure.

Meanwhile, the measurement of blood pressure can be performed 30 minutes after the user has smoked or drunken coffee, and one hour after he has eaten a meal or can be impossible if he has drunken alcohol. The electronic device 101 can output a user interface including time information related to each of smoking, drinking coffee, eating a meal, and drinking alcohol.

According to an embodiment of the present disclosure, the electronic device 101 can determine the time of measurement and validity of measured data through the user's body condition and movement based on the sensed bio signal and tracing the user's activities. The electronic device 101 can classify the above various conditions into factors controllable at the time of measurement and factors uncontrollable due to activities before the time of measurement, and for the former factors, the electronic device 101 can output a user notification such as a voice notification or a user interface while outputting a notification for putting back the time of measurement for the latter factors. Specifically, for the former factors, the electronic device 101 can transfer right measurement conditions including a position and area of measurement and whether pressurized by clothes to the user through a user interface or voice notification before the measurement begins. When measurement of blood pressure initiates, the electronic device 101 can compare a predetermined measurable range with a degree of movement 1520 of the electronic device 101 sensed by a motion sensor, such as an acceleration sensor, geo-magnetic sensor, or gyro sensor, or can compare the predetermined measurable range with the user's voice level 1530 collected through the microphone of the electronic device 101 to determine whether a measured blood pressure is valid.

Figure 17:
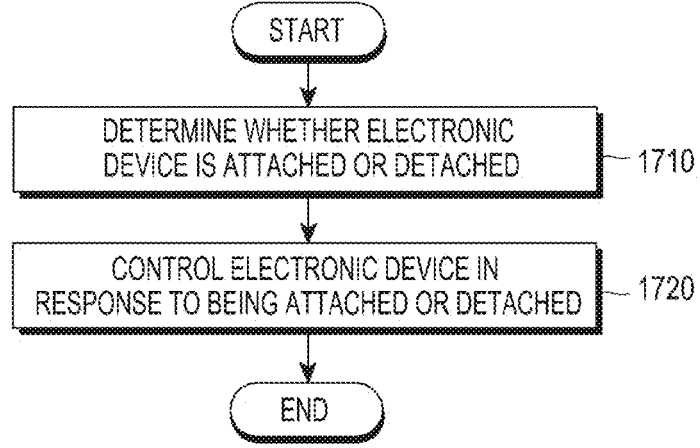
FIG. 17 is a flowchart illustrating a method for controlling an electronic device according to an embodiment of the present disclosure.

FIG. 17 is a flowchart illustrating a method for controlling an electronic device according to an embodiment of the present disclosure.

In operation 1710, the electronic device 101 can obtain information as to whether the electronic device 101 is worn.

In an embodiment, the electronic device 101 can obtain the information as to whether the electronic device 101 is worn based on movement information regarding the electronic device 101 and a coupled state of the coupler. Specifically, the electronic device 101 can determine whether the electronic device 101 is worn based on a direction that the electronic device 101 moves and a coupled state of the coupler.

In an embodiment, the electronic device 101 can obtain the information as to whether the electronic device 101 is taken off based on movement information regarding the electronic device 101 and a coupled state of the coupler. Or, the electronic device 101 can obtain the information as to whether the electronic device 101 is taken off based on a change in the length of the strap.

According to an embodiment of the present disclosure, the information as to whether the electronic device 101 is taken off can be obtained according to sensed data of the electronic device 101, e.g., whether a bio signal is measured. Specifically, the electronic device 101 can determine whether the electronic device 101 is worn using a capacitive touch through a body contact with the user or sensing body temperature. The electronic device 101 can utilize a bio signal sensor, e.g., an electrode-type input value, as a capacitive touch, or a bio signal sensor, e.g., an optical input value, as a capacitive touch. The electronic device 101 can obtain whether the electronic device 101 is attached or detached according to a change in the coupled state of the coupler or a change in the length of the strap. Or, the electronic device 101 can determine whether the electronic device 101 is worn according to whether data is steadily sensed in a stabilized manner after bio signals such as an ECG signal, EMG signal, or HRM signal are sensed.

In operation 1720, the electronic device 101 can control the electronic device 101 corresponding to whether the electronic device 101 is attached or detached. For example, the electronic device 101 can perform an operation of entering into the dormant mode when taken off. Or, the electronic device 101 can output a user interface to request the user to wear back directly or via another electronic device.

Figure 18:
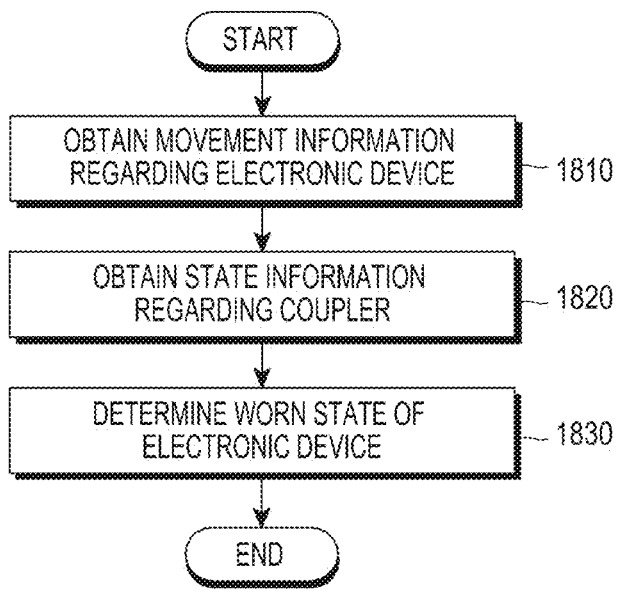
FIG. 18 is a flowchart illustrating a method for controlling an electronic device according to an embodiment of the present disclosure.

FIG. 18 is a flowchart illustrating a method for controlling an electronic device according to an embodiment of the present disclosure. The embodiment of FIG. 18 is described in further detail with reference to FIGS. 19a to 19f. FIGS. 19a to 19f illustrate a configuration for determining whether an electronic device is worn according to an embodiment of the present disclosure.

In step 1810, the electronic device 101 can obtain movement information of the electronic device 101. For example, as shown in FIGS. 19a to 19d, the user 1920 can put the electronic device 101 on the left wrist 1921 by moving the electronic device 101 up and then left. According to an embodiment of the present disclosure, the electronic device 101 can remain in an off state 1910 before a movement is detected and can enter into the standby state 1911 after a movement is detected. The electronic device 101 can obtain movement information regarding the electronic device 101, indicating a move upwards and a move leftwards.

Figure 19A:
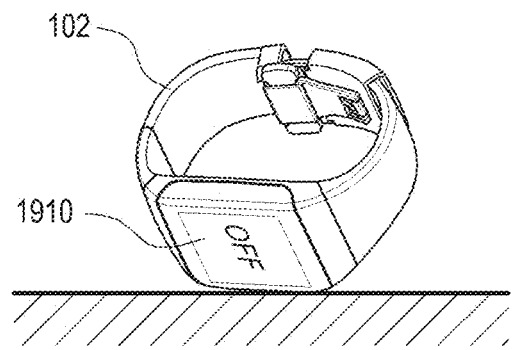
FIGS. 19A to 19F illustrate a configuration for determining whether an electronic device is worn according to an embodiment of the present disclosure.
Figure 19B:
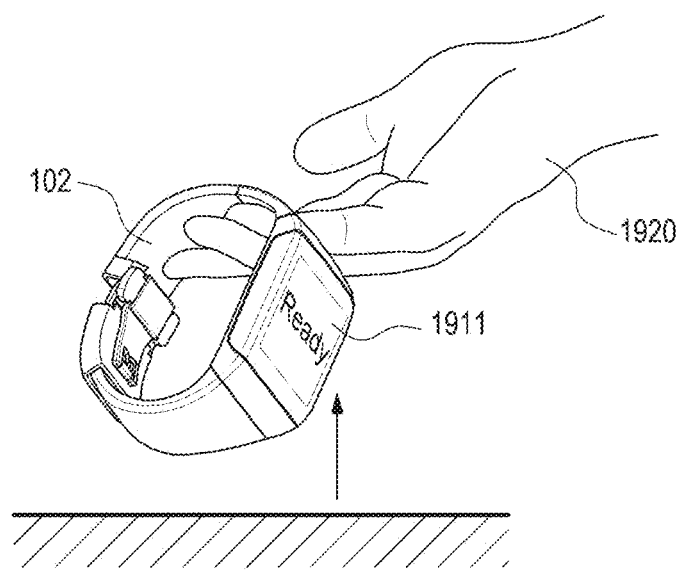
Figure 19C:
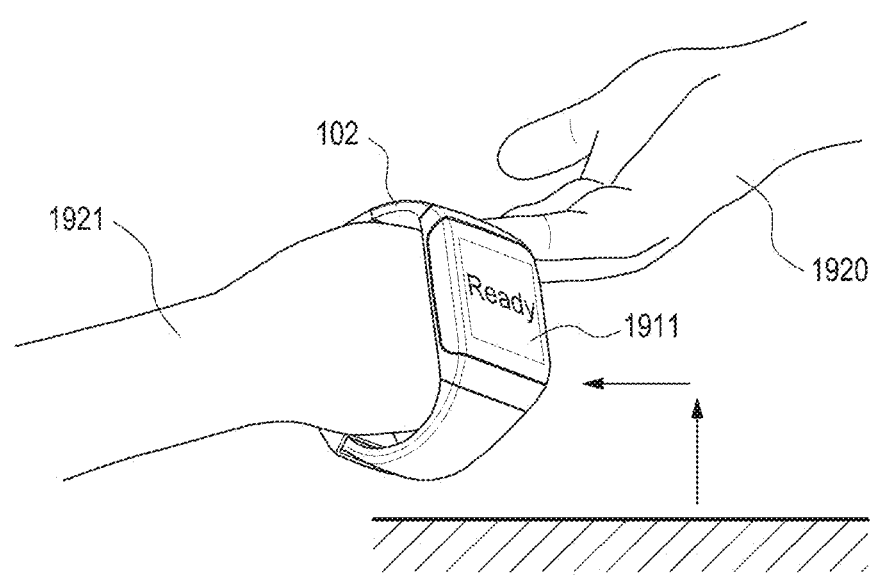
Figure 19D:
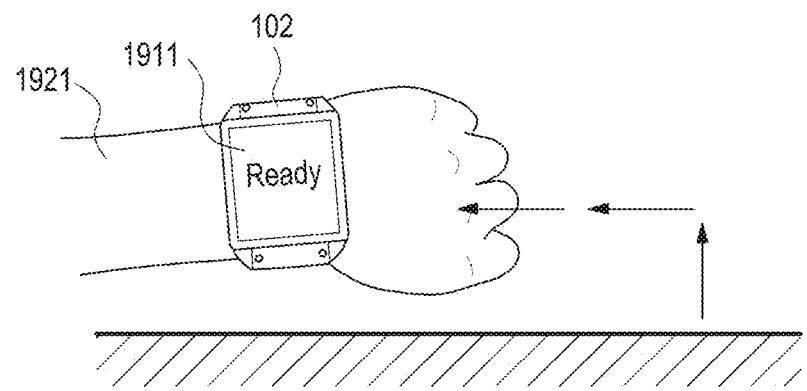
Figure 19E:
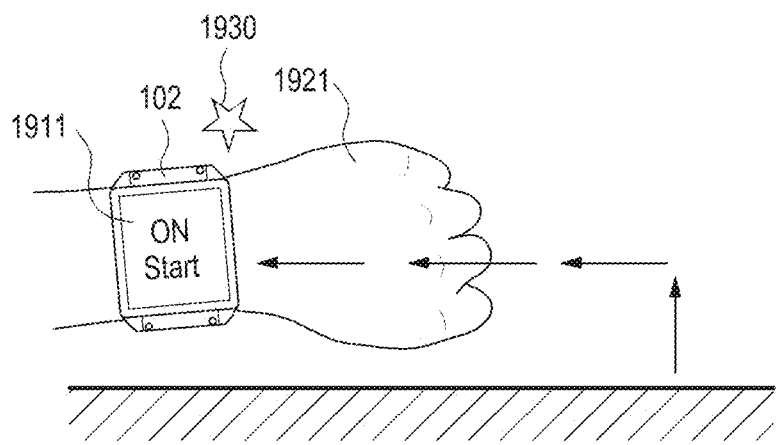
Figure 19F:
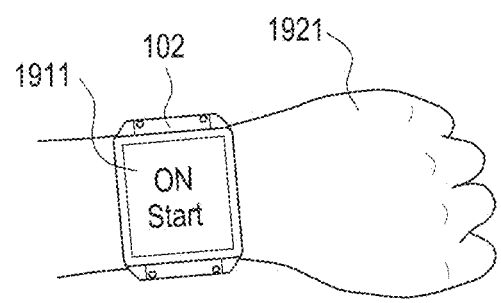

In operation 1820, the electronic device 101 can obtain information on the state of the coupler. For example, as shown in FIG. 19e, the electronic device 101 can obtain a coupling 1930 of the coupler, and as shown in FIG. 19f, the electronic device 101 can be worn on the user's left wrist. The coupler of the electronic device 101 can include a physical coupling means for coupling and a device to measure a coupling of the physical coupling means to output an electrical signal and can thereby obtain a coupling 1930 of the coupler.

In operation 1830, the electronic device 101 can determine a worn state of the electronic device 101 based on the obtained movement information and state information regarding the coupler. For example, the electronic device 101 can determine that the electronic device 101 is worn on the left wrist based on a coupling of the coupler after moving up and left. In an embodiment, the electronic device 101 can determine that the electronic device 101 is worn on the right wrist based on a coupling of the coupler after moving up and right. Accordingly, the electronic device 101 can determine whether the worn portion of the electronic device 101 is the left or right wrist.

Meanwhile, according to an embodiment of the present disclosure, the electronic device 101 can perform different operations depending on whether the worn portion is a left or right side. For example, the electronic device 101 can configure different settings of a user interface or input device depending on the worn portion. When the user puts the electronic device 101 on his right wrist, the electronic device 101 can output a user interface for a right-hand use and make settings for the right-hand use to the input device. By contrast, when the user puts the electronic device 101 on this left wrist, the electronic device 101 can output a user interface for a left-hand use and make settings for the left-hand use to the input device. Here, the user interface for right-hand use and the user interface for left-hand use can simply be left-to-right symmetrical ones, but can provide different functions according to their characteristics. For example, the electronic device 101 can operate as a watch while worn on the left wrist and as an operation controller when worn on the right hand, and vice versa. In some cases, the electronic device 101 can be implemented so that the user can separately set functions for right-hand use and functions for left-hand use. That is, the user himself can set the electronic device 101 so that the electronic device 101 operates as a watch when worn on the right wrist and as a blood pressure meter when worn on the left wrist. Further, for settings to input methods for the wearable device, settings for right-hand use and settings for left-hand use can be automatically converted. For example, the electronic device 101 can make changes so that the direction of a touch gesture when worn on the right wrist is symmetrical with the direction of a touch gesture when worn on the left wrist. Specifically, when the user desires to check his schedule through the watch currently on the screen of the electronic device 101, which is configured with a touchscreen, the electronic device 101 can move onto the scheduler when the user enters a touch gesture from right to left if the user puts the electronic device 101 on his right wrist and when the user enters a left-to-right touch gesture if he puts the electronic device 101 on his left wrist. In a similar manner, the electronic device 101 can change side key operations for the direction of operation of side keys (e.g., volume keys) on the electronic device 101 depending on each worn position.

The electronic device 101 can recommend a worn portion appropriate for a set mode as well as switching operation modes or functions depending on right and left worn positions. For example, in case a right-handed user plays tennis with the electronic device 101 on his right arm, various bio signals intended to be distinguished by the electronic device 101 can show significantly different characteristics for the right arm carrying the tennis racket and the left arm simply playing an auxiliary role. In such case, whether the electronic device 101 is to be worn on the right arm or left arm can be differentiated depending on purposes. If the user desires to analyze the trajectory or speed of swinging the tennis racket, he needs to put the electronic device 101 on his right arm while putting the electronic device 101 on his left arm that shows relatively fewer short movements when the user desires to trace the overall path along which the user has moved in the tennis court while in play. Accordingly, the electronic device 101 can recommend a worn position to the user depending on determined purpose. Here, the electronic device 101 can give such recommendation through, e.g., a visual user interface, an LED lamp, a sound, or a vibration. Further, the electronic device 101 can apply different motion compensation values respectively when worn on the right arm and when worn on left arm.

Figure 20A:
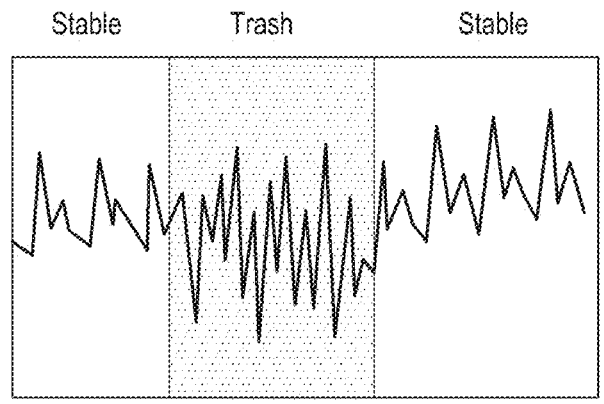
FIGS. 20A and 20B illustrate data sensed by a motion sensor and an HRM signal according to an embodiment of the present disclosure.
Figure 20B:
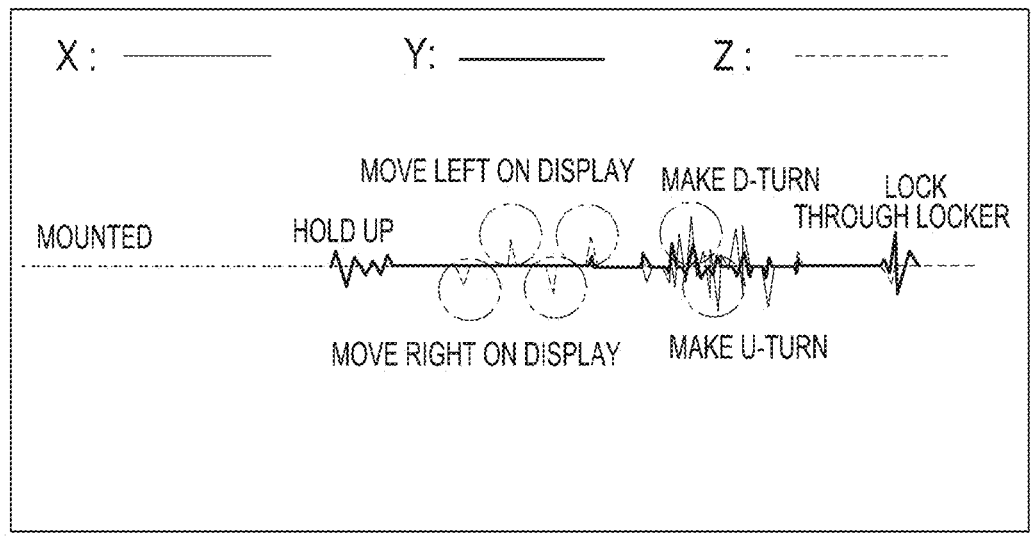

FIGS. 20a and 20b illustrate data sensed by a motion sensor and an HRM signal according to an embodiment of the present disclosure.

The electronic device 101 can sense an HRM signal as shown in FIG. 20a. The HRM signal can contain noise (Trash) as shown in FIG. 20a. The electronic device 101 can determine whether the electronic device 101 is properly worn based on the level of the noise. For example, when the noise level exceeds a threshold, the electronic device 101 can determine that the electronic device 101 is improperly worn and can output a user interface to induce proper wearing. For example, the electronic device 101 can output a user interface to adjust the length of the strap or to induce rewearing.

The electronic device 101 can obtain movement information regarding the electronic device 101 as shown in FIG. 20b. The electronic device 101 can obtain movement degrees respectively for three axes, i.e., an x axis, a y axis, and a z axis. The electronic device 101 can obtain movement information such as a move upwards and a move leftwards as shown in FIGS. 19a to 19d based on the motion information on each of the three axes. As shown in FIG. 20b, corresponding to when the user holds up the electronic device 101, when moving leftwards, when moving rightwards, and when turning around, the electronic device 101 can obtain data on each of the three axes.

Figure 21:
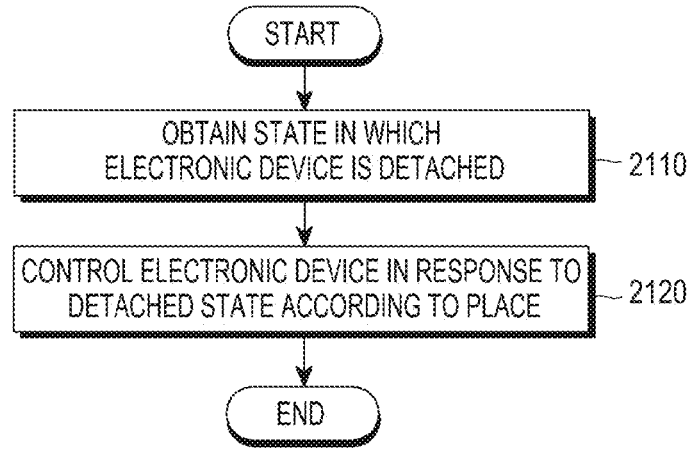
FIG. 21 is a flowchart illustrating a method for controlling an electronic device according to an embodiment of the present disclosure.

FIG. 21 is a flowchart illustrating a method for controlling an electronic device according to an embodiment of the present disclosure.

In operation 2110, the electronic device 101 can obtain a state where the electronic device 101 is taken off.

According to an embodiment of the present disclosure, the electronic device 101 can obtain the taken-off state based on a coupled state of the coupler of the electronic device 101. Or, the electronic device 101 can obtain the taken-off state based on sensed data. For example, when bio signals stops being steadily sensed, the electronic device 101 can determine that it has been taken off.

In operation 2120, the electronic device 101 can control the electronic device 101 corresponding to the taken-off state of the electronic device 101.

Figure 22:
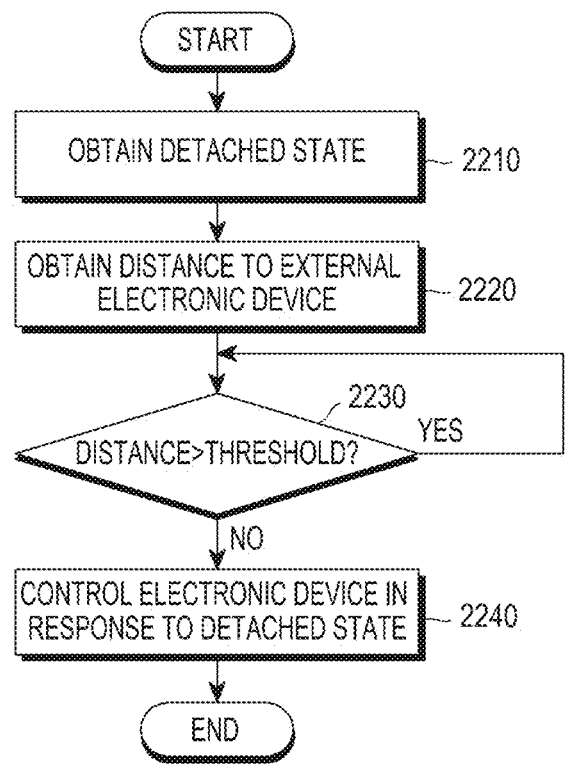
FIG. 22 is a flowchart illustrating a method for controlling an electronic device according to an embodiment of the present disclosure.
Figure 23A:
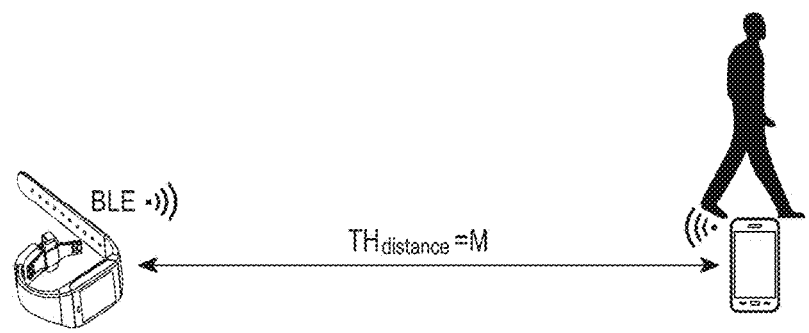
FIGS. 23A and 23B illustrate operations under the state where an electronic device is taken off according to an embodiment of the present disclosure.
Figure 23B:
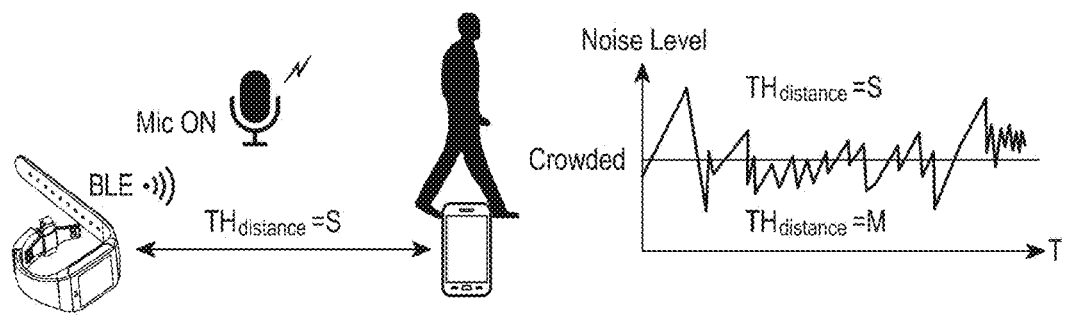

FIG. 22 is a flowchart illustrating a method for controlling an electronic device according to an embodiment of the present disclosure. The embodiment of FIG. 22 is described in greater detail with reference to FIGS. 23a and 23b. FIGS. 23a and 23b illustrate operations under the state where an electronic device is taken off according to an embodiment of the present disclosure.

In operation 2210, the electronic device 101 can obtain a taken-off state. According to an embodiment of the present disclosure, the electronic device 101 can be implemented as a wristwatch-type electronic device as shown in FIG. 23a. Meanwhile, the electronic device 101 can establish communication with an external electronic device 2300. In an embodiment, the electronic device 101 can establish communication with the external electronic device 2300 via Bluetooth low energy (BLE), but this is merely an example, and it will be readily appreciated by one of ordinary skill in the art that no limit is posed on the type of communication.

In operation 2220, the electronic device 101 can obtain a distance from the external electronic device 2300. For example, the electronic device 101 can obtain the distance between the electronic device 101 and the external electronic device 2300 based on the strength of a signal received from the external electronic device 2300 via the BLE. Or, the external electronic device 2300 can obtain the distance based on the strength of a signal received from the electronic device 101 and can send the obtained distance to the electronic device 101.

In operation 2230, the electronic device 101 can determine whether the distance between the electronic device 101 and the external electronic device 2300 exceeds a threshold M. In operation 2240, when the distance exceeds the threshold M, the electronic device 101 can control the electronic device 101 to correspond to the taken-off state. In one embodiment, the electronic device 101 can output a notification sound. The user can be prevented from losing the electronic device 101 by hearing the notification sound from the electronic device 101. In an embodiment, the electronic device 101 can transmit a user notification message to the external electronic device 2300, and the external electronic device 2300 can output a notification sound, vibration, or user interface indicating that the user took off the electronic device 101 and left it behind based on the received user notification message. In an embodiment, the electronic device 101 can transmit information on the current location to the external electronic device 2300. The external electronic device 2300 can display the current location of the electronic device 101 based on the received current location information, and the user can identify the same to get the electronic device 101 back. In an embodiment, the electronic device 101 can send out a notification message to a management electronic device at the current location, but not the external electronic device 2300. In such case, the owner of the management electronic device, e.g., the manager of the corresponding place, can pick up the electronic device 101 and later get it back to the user. In an embodiment, when worn back by the user after having outputted the notification sound or sent out the notification message, the electronic device 101 can perform authentication based on a bio signal. As a result of the authentication, the electronic device 101 can determine that not the user but the finder is wearing the electronic device 101 as a result of the authentication, and in such case, the electronic device 101 can enter into the security mode. In this case, the electronic device 101 can output an alert message. In an embodiment, the electronic device 101 can interwork with a vehicle control system and can receive various state information related to the vehicle from the vehicle control system. For example, the electronic device 101 can receive the state information of "parking" from the vehicle control system. The electronic device 101 can output a notification sound or vibration corresponding to the reception of the state information of "parking" to induce the user to wear the electronic device 101 back.

As shown in FIG. 23b, according to an embodiment of the present disclosure, the electronic device 101 can update the threshold M to another threshold S corresponding to the level of ambient noise. For example, the electronic device 101 can decrease the threshold as the level of ambient noise increases. That is, in an environment with a higher level of ambient noise, the electronic device 101 can output a notification sound even when the distance from the user is relatively short.

Figure 24:
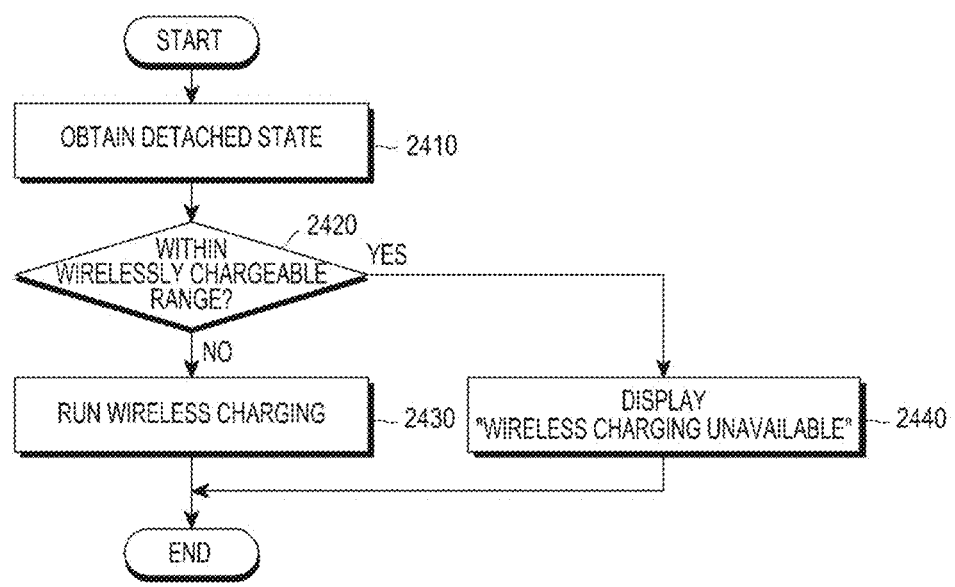
FIG. 24 is a flowchart illustrating a method for controlling an electronic device according to an embodiment of the present disclosure.

FIG. 24 is a flowchart illustrating a method for controlling an electronic device according to an embodiment of the present disclosure.

In operation 2410, the electronic device 101 can obtain a state where the electronic device 101 is taken off.

In operation 2420, the electronic device 101 can determine whether the electronic device 101 is within a wirelessly chargeable range. According to an embodiment of the present disclosure, the electronic device 101 can include a wireless charging module that can wirelessly receive power from a wireless power transmitter. The electronic device 101 can receive power from the wireless power transmitter in a resonant or inductive method. Meanwhile, the electronic device 101 can perform communication with the wireless power transmitter. The electronic device 101 can determine whether it is within the wirelessly chargeable range based on a result of the communication with the wireless power transmitter. Or, the electronic device 101 can determine whether it is within the wirelessly chargeable range based on whether to receive wireless power.

In operation 2430, when determined that it is within the wirelessly chargeable range, the electronic device 101 can receive wireless power to perform wireless charging. In operation 2440, when determined that it is out of the wirelessly chargeable range, the electronic device 101 can display a message indicating that wireless charging is impossible. The electronic device 101 can display the wireless charing impossible message along with a notification sound or vibration. Or, the electronic device 101 can transmit the wireless charging impossible message to another electronic device included in the home network, and the other electronic device can induce the user to move the electronic device 101 in the wirelessly chargeable area by displaying the received wireless charging impossible message. The electronic device 101 can first transmit the wireless charging impossible message to a nearby electronic device or can transmit the message to all of the electronic devices in the home network.

Figure 25:
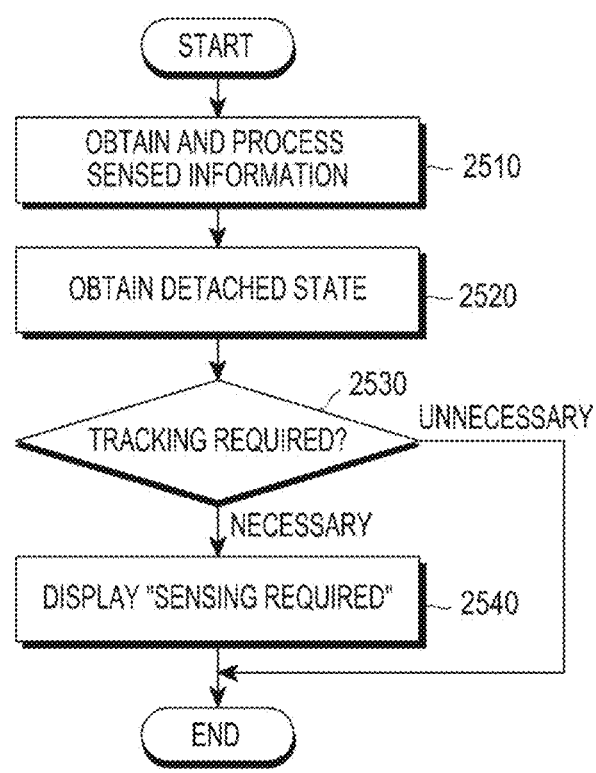
FIG. 25 is a flowchart illustrating a method for controlling an electronic device according to an embodiment of the present disclosure.
Figure 26:
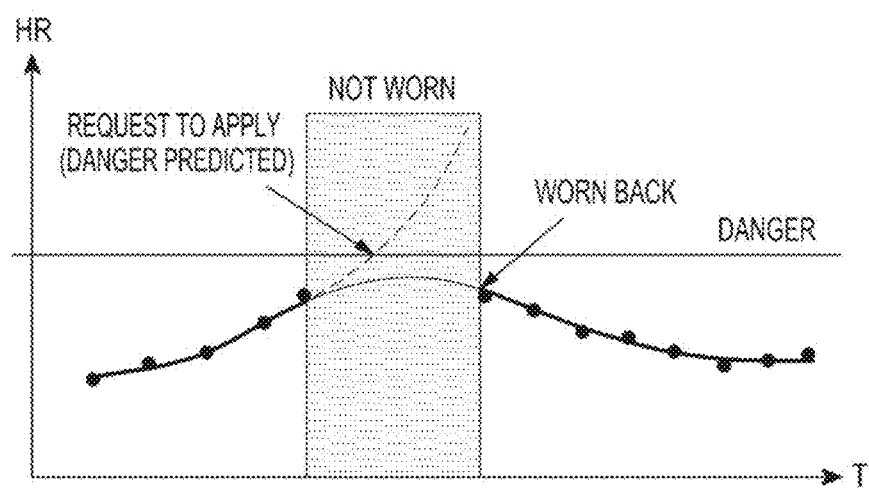
FIG. 26 illustrates a graph for times when sensed information is obtained by an electronic device according to an embodiment of the present disclosure.

FIG. 25 is a flowchart illustrating a method for controlling an electronic device according to an embodiment of the present disclosure. The embodiment shown in FIG. 25 is described in further detail with reference to FIG. 26. FIG. 26 illustrates a graph for times when sensed information is obtained by an electronic device according to an embodiment of the present disclosure.

In operation 2510, the electronic device 101 can obtain and process sensed data. For example, the electronic device 101 can sense a heart rate (HR) signal and process the sensed HR signal to output in the form of a graph as shown in FIG. 26. According to an embodiment of the present disclosure, when wearing the electronic device 101, the user's hear rate can be identified to rise.

In operation 2520, the electronic device 101 can obtain a taken-off state. In an embodiment, the electronic device 101 can obtain the taken-off state of the electronic device 101 based on HR signals used to be steadily sensed stopping being sensed.

In operation 2530, the electronic device 101 can determine whether tracking is needed. The electronic device 101 can estimate information predicted to be sensed within a period during which the electronic device 101 is not worn based on the trend of sensed information. For example, as shown in FIG. 26, the HR signal can be identified to increase within a period during which the user wears the electronic device 101. The electronic device 101 can determine the predicted-to-be-sensed information within the not-wearing period denoted in dotted lines based on the sensed information trend within the wearing period. The electronic device 101 can previously store a threshold indicating that the user's health is in danger. The electronic device 101 can determine whether tracking is required by determining whether the predicted-to-be-sensed information within the not-wearing period exceeds the threshold. For example, as shown in FIG. 26, upon determining that the predicted-to-be-sensed information exceeds the threshold, the electronic device 101 can determine that tracking is required. Based on first information that is a HR signal, the electronic device 101 can determine second information that is the user's health condition and can determine whether to track the first information using the determined first information.

In operation 2540, when determined that tracking is required, the electronic device 101 can induce the user to wear the electronic device 101 by displaying the need of sensing. For example, the electronic device 101 can output a notification sound or vibration and a user interface to induce wearing. When the user re-wears the electronic device 101, the electronic device 101 can re-measure sensed information and display results measured and processed.

According to an embodiment of the present disclosure, the electronic device 101 can determine whether other electronic devices trackable are around the electronic device 101. For example, the electronic device 101 can receive an advertisement signal including a capability from another electronic device and can thus determine whether there are other electronic devices including a tracking function. For example, when the electronic device 101 senses a heart rate as shown in FIG. 26, the electronic device 101 can determine whether there is another electronic device capable of sensing a heart rate around the electronic device 101. When there is the other electronic device capable of tracking around, the electronic device 101 can transmit sensed data to the other electronic device capable of tracking.

According to an embodiment of the present disclosure, the electronic device 101 can operate based on the user's state before taken off. For example, the electronic device 101 can determine the user's state before taken off as, e.g., a normal state, a dangerous state, a going-in-danger state, and a workout state. The electronic device 101 can determine the user's state based on a result of applying a state determination algorithm to a bio signal sensed from the user. When the user's state is determined as the normal state, the electronic device 101 can determine that tracking is not required. When the user's state is determined as the dangerous state, the electronic device 101 can notify that tracking is required right after the user takes off the electronic device 101. When the user's state is determined as the going-in-danger state, the electronic device 101 can determine what time after the user's take-off the user goes in the dangerous state. The electronic device 101 can notify that tracking is required after the determined time elapses. When the user's state is determined as the workout state, the electronic device 101 can notify that tracking is required in order to determine whether the user enters into a stabilized state after a predetermined time.

Figure 27:
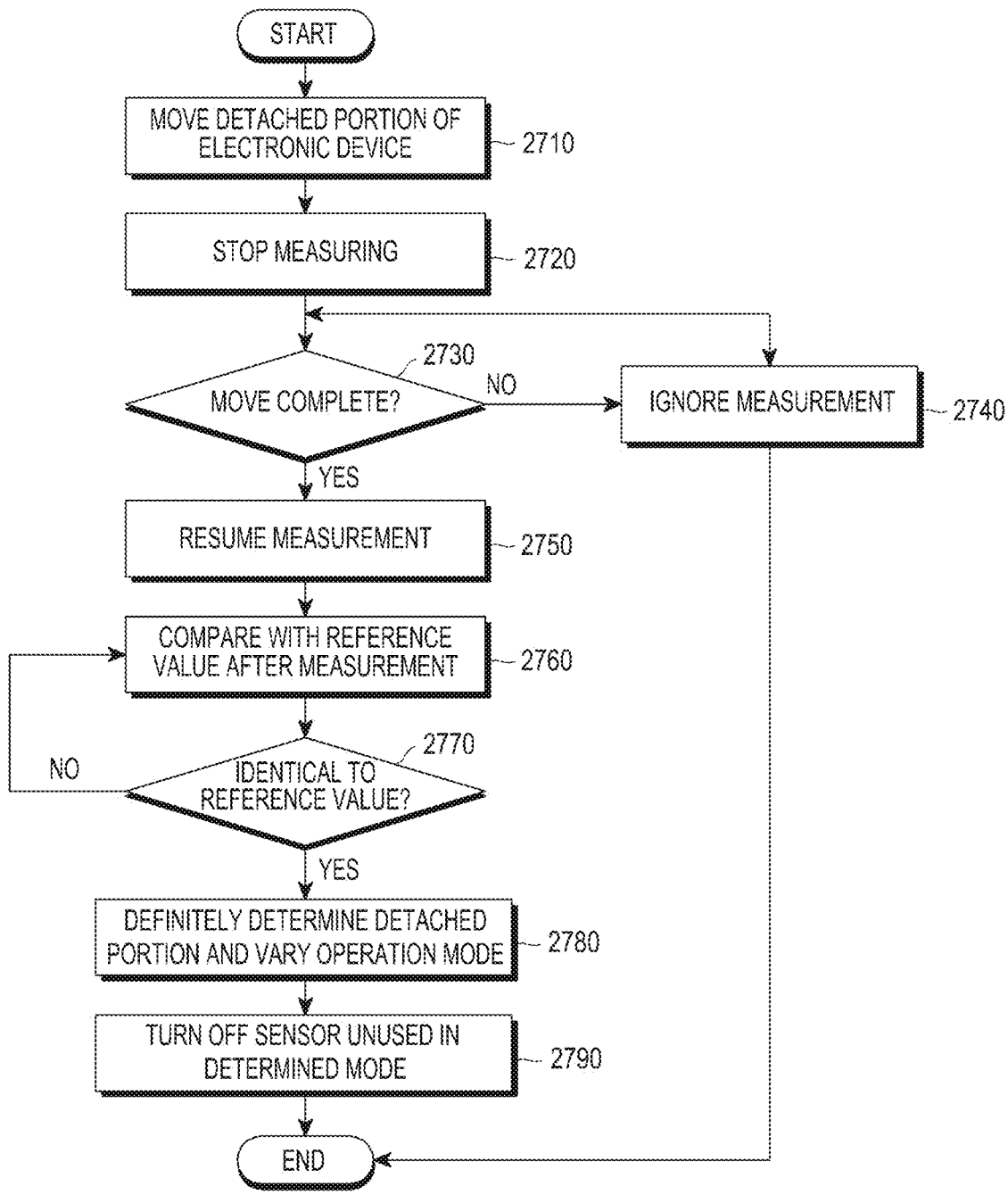
FIG. 27 is a flowchart illustrating a method for controlling an electronic device according to an embodiment of the present disclosure.

FIG. 27 is a flowchart illustrating a method for controlling an electronic device according to an embodiment of the present disclosure.

In operation 2710, the electronic device 101 can detect a move of the worn portion of the electronic device 101. In an embodiment, the electronic device 101 can detect the move of the worn portion based on movement information regarding the electronic device 101. In an embodiment, the electronic device 101 can detect the move of the worn portion based on a change in the type of a bio signal primarily obtained or a change in the strength of a bio signal obtained.

In operation 2720, upon detecting the change in the worn portion of the electronic device 101, the electronic device 101 can pause measuring sensed data, such as bio signals. Or, the electronic device 101 can disregard sensed data measured.

When the move of the electronic device 101 is incomplete in operation 2730, the electronic device 101 can pause measuring the sensed data in operation 2720. The electronic device 101 can determine whether the move is complete based on the pause of changing the type or strength of the bio signal or movement information.

When the move of the electronic device 101 is complete, the electronic device 101 can resume the measurement of sensed data in operation 2750.

In operation 2760, the electronic device 101 can compare sensed data after the measurement is complete with a previously stored reference value. In operation 2770, the electronic device 101 can determine whether the sensed data after the measurement is complete is identical to the reference value. When the reference value is identical to the sensed data after the measurement is complete, the electronic device 101 can definitely determine the worn portion and turn into an operation mode corresponding to the determined worn portion in operation 2780. In operation 2790, the electronic device 101 can turn off unused sensors corresponding to the determined operation mode.

For example, the electronic device 101 can be worn on the initial user's wrist and obtain a bio signal from the wrist. Meanwhile, the user can shift the electronic device 101 from the wrist to the forearm. The electronic device 101 is highly likely to measure distorted signals while shifting to the forearm and can pause the measurement to prevent such distorted signals from reflected to the accrued measurement value. Further, when the move is complete so that stable signals are steadily measured, the electronic device 101 can obtain sensed data from the forearm. In particular, the electronic device 101 can turn off the ECG signal sensor to measure EMG signals from the forearm.

Figure 28:
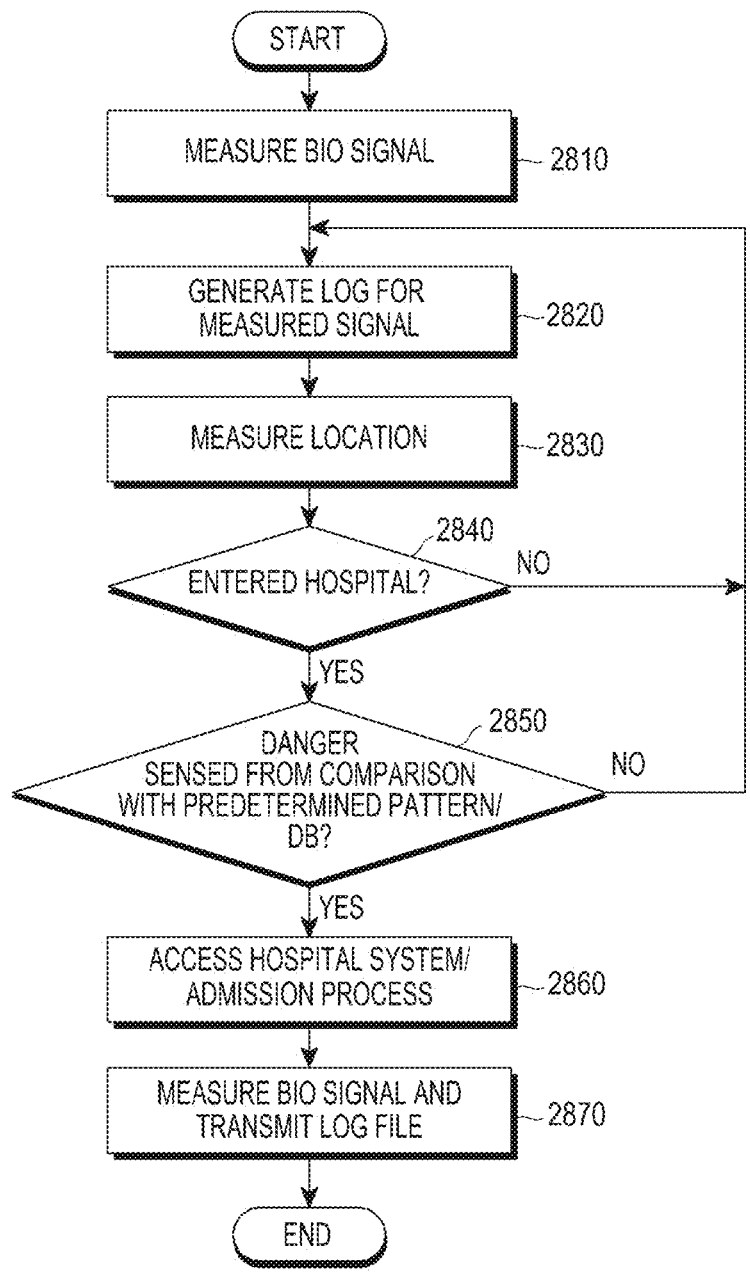
FIG. 28 is a flowchart illustrating a method for controlling an electronic device according to an embodiment of the present disclosure.

FIG. 28 is a flowchart illustrating a method for controlling an electronic device according to an embodiment of the present disclosure. In the embodiment shown in FIG. 28, it is assumed that the electronic device 101 interworks with a system previously established in a hospital.

In operation 2810, the electronic device 101 can measure bio signals. The electronic device 101 can measure bio signals, such as ECGs, EMGs, EEGs, HRMs, blood sugar levels, or blood pressures.

In operation 2820, the electronic device 101 can generate a log for a measured bio signal. For example, the electronic device 101 can generate per-time logs for measured bio signals. According to an embodiment of the present disclosure, the log can include information that can generate the user's health condition based on the measured bio signal and can be implemented in the form of a database (DB) or a particular pattern.

In operation 2830, the electronic device 101 can measure the current location of the electronic device 101. According to an embodiment of the present disclosure, the electronic device 101 can measure the current location using, e.g., a global navigation satellite system (GNSS), a Wi-Fi localization system (WPS), a cell identity (ID), or a beacon.

In operation 2840, the electronic device 101 can determine whether the electronic device 101 enters the hospital based on the measured location.

When determined that the electronic device 101 has entered the hospital, the electronic device 101 can sense whether the user's health condition is in danger using at least one of a stored pattern and DB in operation 2850. Immediately when determined that the electronic device 101 has entered the hospital, the electronic device 101 can interwork with a hospital system to transmit information on the patient's condition to treatment and medical staff in operation 2860. In operation 2870, the electronic device 101 can transmit a log file for the bio signal and the patient's health condition information analyzed to the interworking system.

According to an embodiment of the present disclosure, the electronic device 101 can more accurately perform the measurement and analysis of bio signals when entering the hospital as compared with when it is located outside the hospital. When located outside the hospital, the electronic device 101 can operate in a normal measurement mode that measures only minimum bio information enabling a checkup on the user's condition in order to prevent system load while decreasing power consumption. In the normal measurement mode, the period of sensing various bio signals can be increased while the measuring sensitivity of the sensors can be lowered to roughly check the user's condition.

Meanwhile, upon entry into the hospital, the electronic device 101 can operate in an accurate measurement mode at which the measurement mode of the wearable device worn by the user is more accurate than existing ones. Sometimes, such situation can occur where the data measured by the electronic device 101 should be transferred to the hospital DB, and in the accurate measurement mode, as accurate measurement as can be used in the hospital can be carried out.

Thus, when the electronic device 101 enters the hospital, the electronic device 101 can display and notify proper steps the user can take to exactly measure, e.g., body temperature. Or, the electronic device 101 can indicate conditions for the position upon or before measurement when measuring blood pressure or heart rate.

Figure 29:
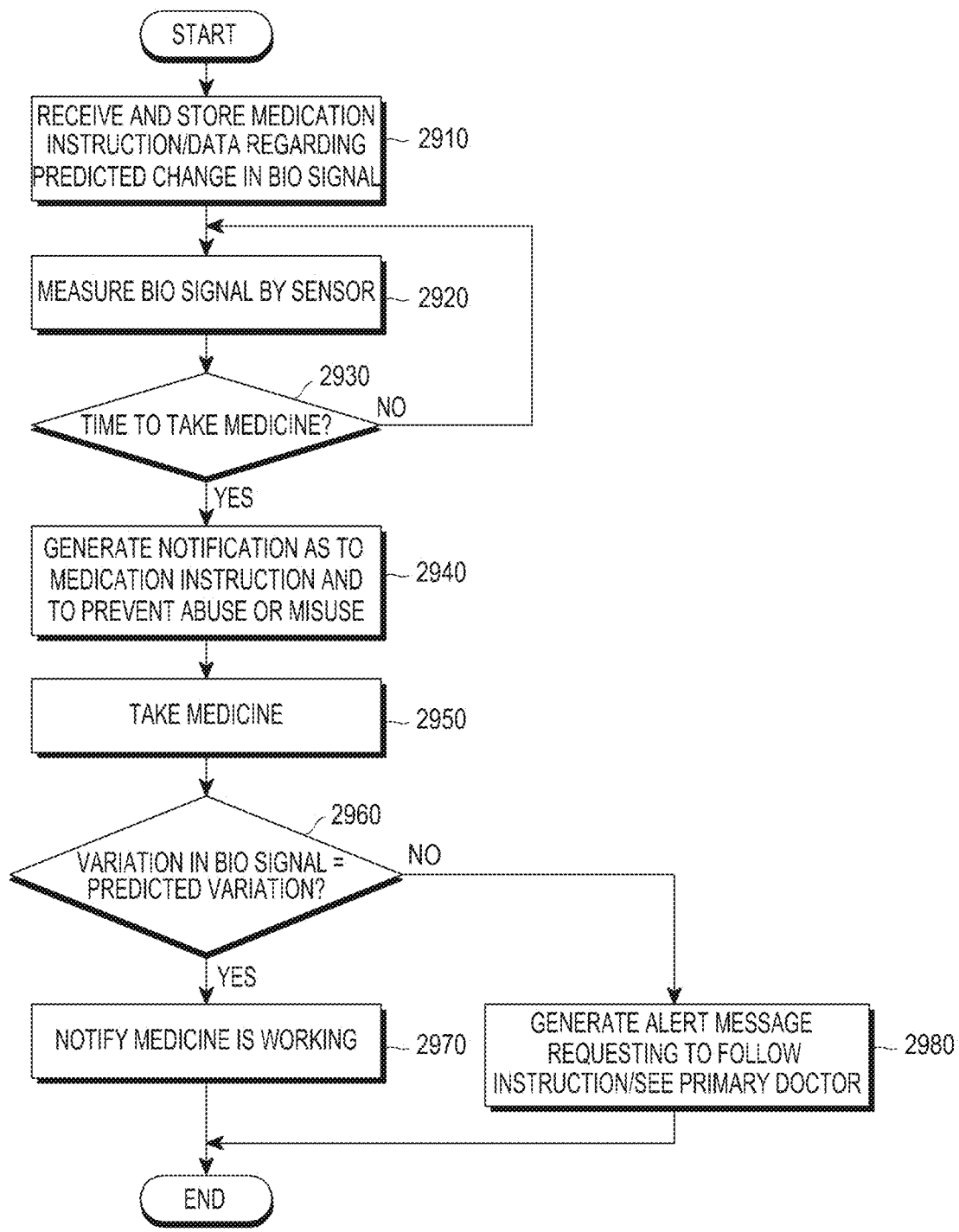
FIG. 29 is a flowchart illustrating a method for controlling an electronic device according to an embodiment of the present disclosure.

FIG. 29 is a flowchart illustrating a method for controlling an electronic device according to an embodiment of the present disclosure.

In operation 2910, the electronic device 101 can receive and store instructions required to follow for a particular medicine and data predicted for changes in bio signals. Specifically, the electronic device 101 can receive and store instructions required to follow for a medicine and data predicted for changes in bio signals from the pharmacy store where the medicine was purchased, the pharmaceutical company that manufactured the medicine, the Food and Drug Administration (FDA), the ministry of health and welfare, or other sources that can provide such instructions and information when the user purchase the medicine. Here, the bio signals include changes in body temperature, heart rates, electromyograms, muscle signals, brain wave signals, or other types of information that can indicate changes in body. The electronic device 101 can notify the user of the time of taking the medicine based on the information received after purchase.

In operation 2920, the electronic device 101 can measure bio signals. The electronic device 101 can measure bio signals before and after the time of taking the medicine.

In operation 2930, the electronic device 101 can determine whether it is the time of taking the medicine based on the received information. When it is the time of taking the medicine, the electronic device 101 can generate an instruction to follow about taking the medicine in operation 2940. Or, the electronic device 101 can generate a notification to prevent medicine abuse or misuse.

In operation 2950, the electronic device 101 can obtain information whether the user takes the medicine or not. The electronic device 101 can obtain the information as to whether the user takes the medicine through a feedback from the user. Or, the electronic device 101 can obtain the information as to whether the user takes the medicine based on a change in a bio signal measured from the user.

In operation 2960, the electronic device 101 can determine whether a variation in the bio signal between before and after the time of taking the medicine is the same as a predicted variation. Specifically, the electronic device 101 can determine whether the variation in the bio signal between before and after the time of taking the medicine is different from the predicted variation by a threshold or less.

When the variation in the bio signal between before and after the time of taking the medicine is different from the predicted variation by the threshold or less, the electronic device 101 can notify that the medicine has worked in operation 2970. Unless the variation in the bio signal between before and after the time of taking the medicine is different from the predicted variation by the threshold or less, the electronic device 101 can generate an alert message indicating to follow the instructions and requesting to see the primary care doctor. Accordingly, the electronic device 101 can reminder the user of the instructions about taking the medicine, or when the body temperature sharply changes or dyspnea, cardiac abnormalities, muscular rigidity or other side effects occur, the electronic device 101 allows the user to stop the medication or to see the primary care doctor to get a new prescription. The present embodiment can apply to periodically taking medicines to, e.g., manage blood sugar or blood pressure or to mitigate temporary symptoms such as headache or stomachache. Further, this embodiment can also be applicable to medications related to females such as contraception, menstrual cycle, or pregnancy.

Further, the instant embodiment can operate differently depending on temporary or periodic medication. For the temporary medication, the electronic device 101 can receive data including medication instructions and predicted effects (changes in bio signals) when receiving the medicine from the pharmacy store and can alert the user to non-use/abuse or misuse or the time of taking the medicine based on the received data and can grasp the effects as bio signals. For the periodic medication, the electronic device 101 can manage medication information regarding the user who periodically takes medicines such as, e.g., blood sugar pills, insulin, or blood pressure pills. The electronic device 101 can classify patients of a corresponding disease by computing a periodic pattern of variations in blood sugar or blood pressure values. Further, the electronic device 101 can also change per-disease tracking modes, generate an additional DB, and fulfill intensive care. Or, the electronic device 101 can manage female-dedicated medication and can utilize variations in bio signals or body temperature according to, e.g., contraceptives, menstrual cycle, or gestation period.

Figure 30A:
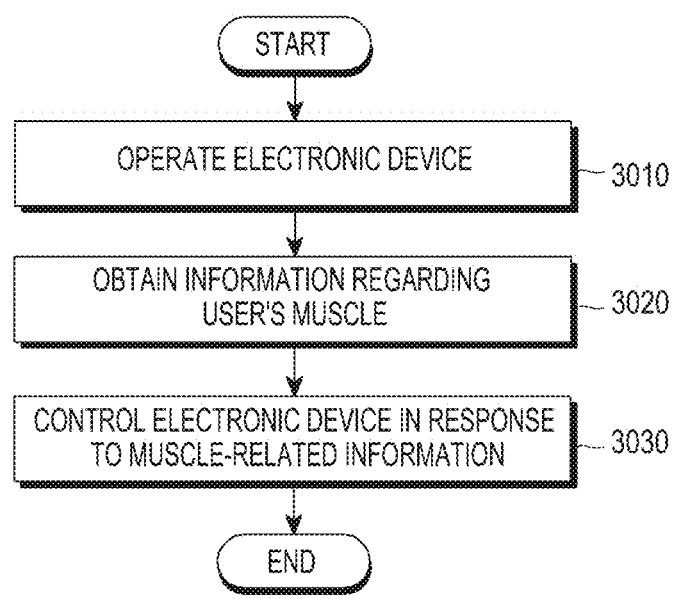
FIG. 30A is a flowchart illustrating a method for controlling an electronic device according to an embodiment of the present disclosure.
Figure 31:
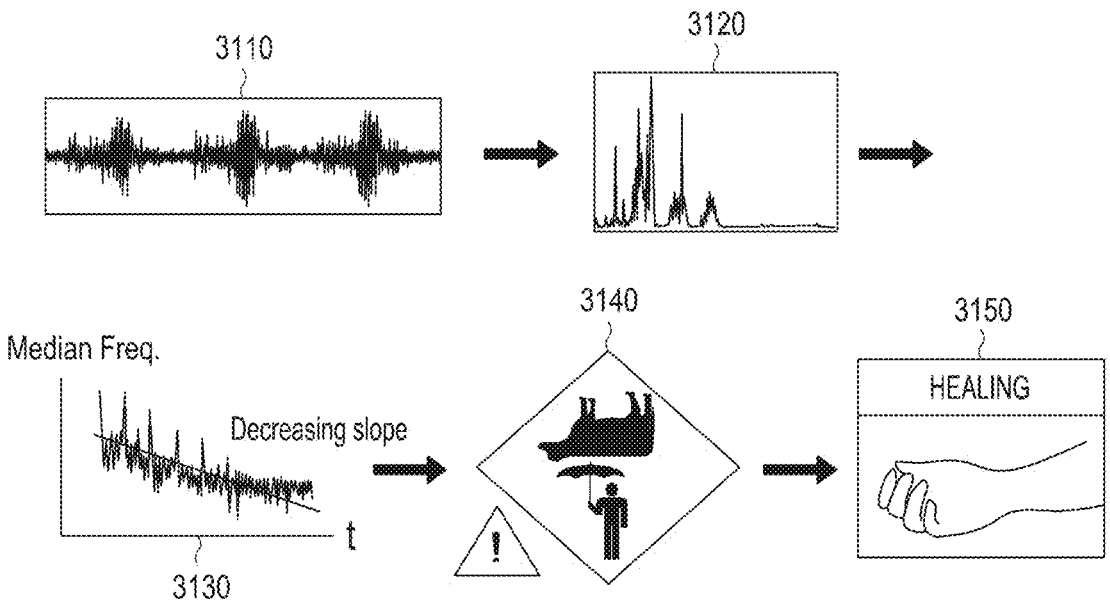
FIG. 31 is a concept view illustrating an operation of an electronic device according to an embodiment of the present disclosure.

FIG. 30a is a flowchart illustrating a method for controlling an electronic device according to an embodiment of the present disclosure. The embodiment shown in FIG. 30a is described in further detail with reference to FIG. 31. FIG. 31 is a concept view illustrating an operation of an electronic device according to an embodiment of the present disclosure.

In operation 3010, the electronic device 101 can operate to run, e.g., an application requesting the user to move.

In operation 3020, the electronic device 101 can obtain muscle-related information from the user. For example, the electronic device 101 can obtain an EMG signal 3110 from the user as shown in FIG. 31. The electronic device 101 can convert the EMG signal 3110 into an EMG signal 3120 in the frequency domain. For example, the electronic device 101 can perform a fast Fourier transformation (FFT) to obtain the EMG signal 3120 converted in the frequency domain. The electronic device 101 can obtain an EMG signal graph 3130 converted in the frequency domain over time.

In operation 3030, the electronic device 101 can control the electronic device 101 corresponding to the muscle-related information. For example, when the muscle-related information has more noise, the electronic device 101 can perform a muscle-fatigue recovery operation 3150. For example, when the EMG signal converted in the frequency domain exhibits a decreasing frequency, the electronic device 101 can determine the danger (3140) of muscle fatigue. According to an embodiment of the present disclosure, the electronic device 101 can apply a massage effect to the worn portion by repeatedly increasing and decreasing the length of the strap.

When muscles on a particular area are used for a long time, muscular fibers can be subjected to repetitive stimulation so that the activation speed (frequency of stimulus) remains the same, and stimulation in synapses and muscle cell membranes, activation for emission of calcium ions, and contraction of sliding filaments are repeated to proceed with accumulation or consumption of metabolites. Here, electromyogram (EMG) signals show a tendency of converting from high-frequency components to low-frequency components. Accordingly, the electronic device 101 can perform a muscle fatigue recovery operation when detecting the tendency of descending frequency. The electronic device 101 can determine an increase in muscle fatigue based on the trend of a per-time reduction in frequency, e.g., when the slope is a negative number.

According to an embodiment of the present disclosure, when determining that the muscle fatigue increases, the electronic device 101 can additionally check the health condition. When an abnormality is discovered upon checkup on the health condition, the electronic device 101 can notify the user of the same. The electronic device 101 can advise the user to relax and can provide a detailed information query about the current condition. Or, the electronic device 101 can automatically play music for relaxation. In particular, when there is a log indicating that the user's fatigue is decreased by a particular song, the electronic device 101 can play the song. Not discovering any abnormality upon checkup on the health condition, the electronic device 101 can determine that the user is in a normal fatigue range. The electronic device 101 can update a predetermined reference for determining health conditions based on a result of the determination.

Figure 30B:
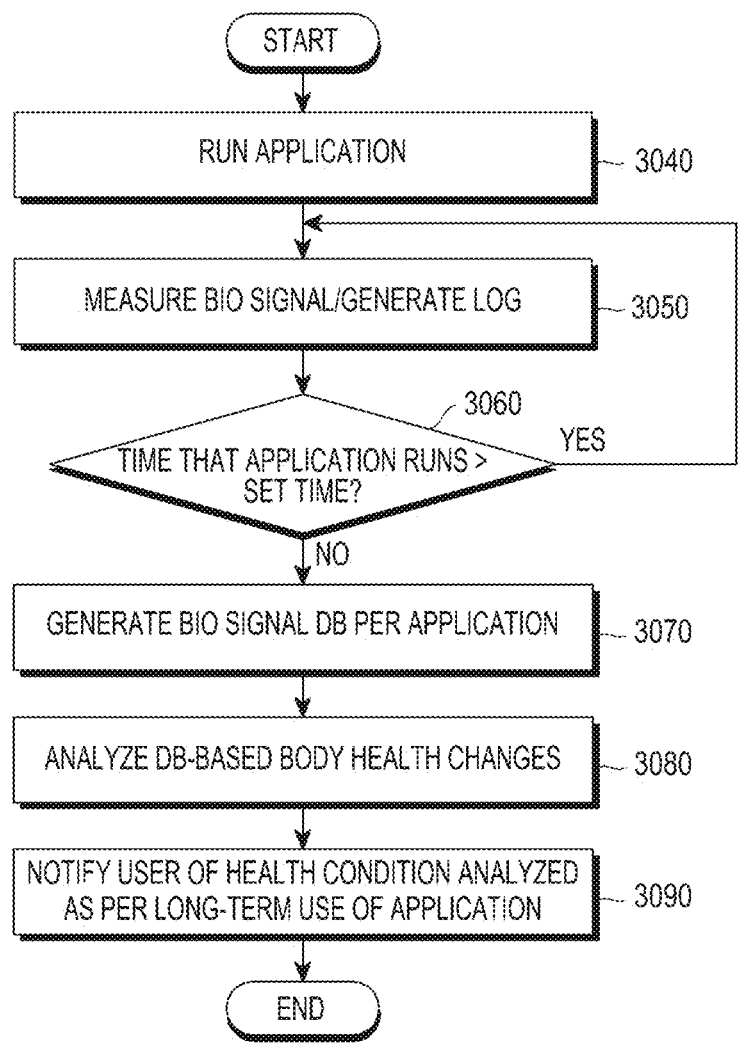
FIG. 30B is a flowchart illustrating a method for controlling an electronic device according to an embodiment of the present disclosure.

FIG. 30b is a flowchart illustrating a method for controlling an electronic device according to an embodiment of the present disclosure. The instant embodiment can relate to a function for notifying that long-term use of applications including game or Internet browsing applications can influence the user's health. The electronic device 101 can sense a variation in biorhythm using a bio signal sensor and can notify the user of what affects the user's health.

In operation 3040, the electronic device 101 can run an application that can induce a variation in the bio signal. For example, the electronic device 101 can run an application such as a game requiring body movements.

In operation 3050, the electronic device 101 can measure bio signals. The electronic device 101 can generate a log of bio signals for times after the application is driven. Here, the bio signals include changes in body temperature, heart rates, electromyograms, muscle signals, brain wave signals, or other information that can indicate changes in body.

Meanwhile, the long-term use of the application can cause symptoms such as stimulation, headaches, or drastic emotional changes. The electronic device 101 can analyze the drastic changes through the generated log. The electronic device 101 can set a proper use time per application. In operation 3060, the electronic device 101 can determine whether the application running time exceeds the set proper use time.

When determining that the application running time exceeds the proper use time, the electronic device 101 can generate a per-application bio signal database in operation 3070. In operation 3080, the electronic device 101 can analyze database-based body health changes. In operation 3090, the electronic device 101 can notify the user of the analyzed health condition according to the long-term use of the application. According to an embodiment of the present disclosure, the electronic device 101 can notify the user that his health condition has experienced a temporary change as compared with before the application is used by the long-term use of the application to recommend the user for a relaxation time or gymnastics or stretching that can recover the user's biorhythm to a normal condition. Or, as described above, the electronic device 101 can perform a muscle fatigue recovery operation that repeatedly increases and decreases the length of the strap.

Figure 32:
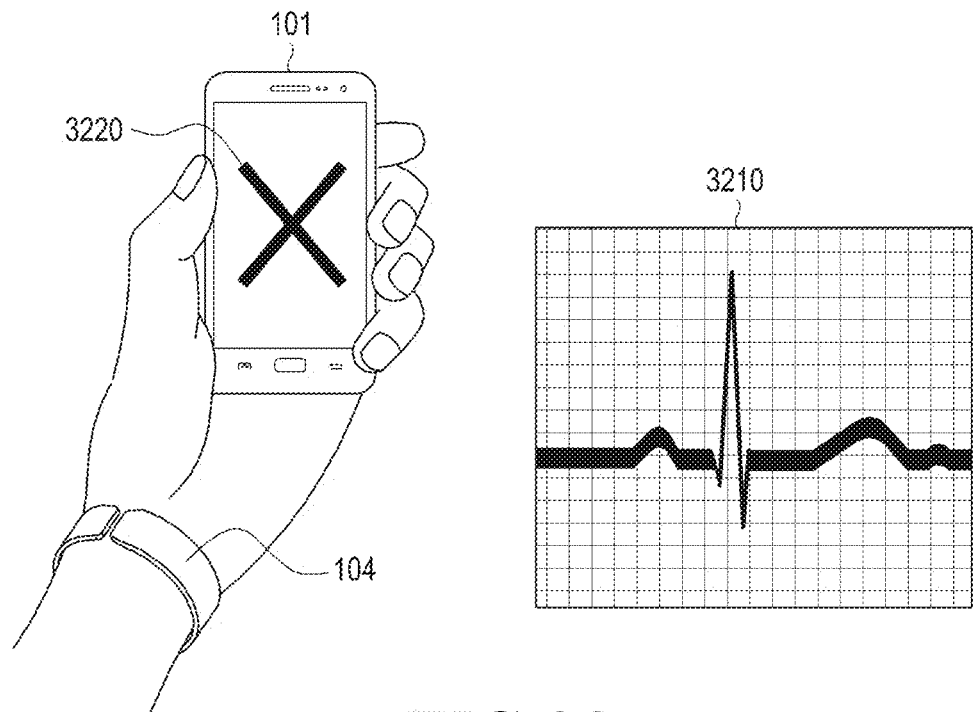
FIG. 32 is a concept view illustrating a method for authenticating an electronic device according to an embodiment of the present disclosure.

FIG. 32 is a concept view illustrating a method for authenticating an electronic device according to an embodiment of the present disclosure.

As shown in FIG. 32, the electronic device 101 can obtain a bio signal 3210. The electronic device 101 can obtain a bio signal, such as an ECG or HRM. The electronic device 101 can previously store the user's bio signal and can compare the previously stored bio signal with the obtained bio signal to perform authentication. The electronic device 101 can interwork with another electronic device 102 and can transmit a result of the authentication to the other electronic device 102. The other electronic device 102 can operate based on the received authentication result. For example, when receiving the authentication result indicating that the authentication fails, the other electronic device 102 can output an unable-to-use user interface 3220 and can restrict the use of the other electronic device 102. According to an embodiment of the present disclosure, when the authentication fails, the electronic device 101 or the other electronic device 102 can automatically contact its owner or can output an alert message. Or, the electronic device 101 can send a request at a previously stored contact number to inquire about various crime histories. Further, when the authenticated user is an elderly person or suffers from dementia or other disease, the electronic device 101 can record and send the current location to a server at a predetermined period so that the server can pinpoint the user.

According to an embodiment of the present disclosure, when the distance from the other electronic device is less than a predetermined threshold, if the length of the strap of the electronic device 101 is not changed, the other electronic device, e.g., a smartphone, can skip the user authentication.

Figure 33:
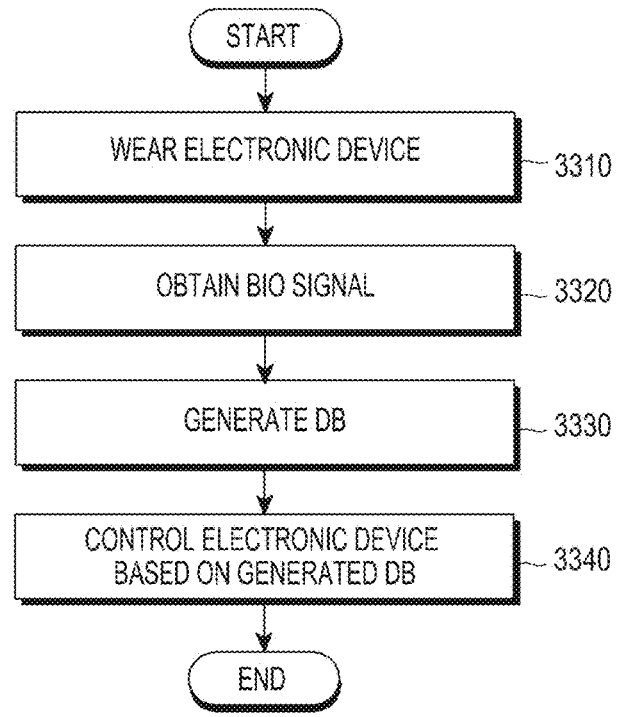
FIG. 33 is a flowchart illustrating a method for controlling an electronic device according to an embodiment of the present disclosure.

FIG. 33 is a flowchart illustrating a method for controlling an electronic device according to an embodiment of the present disclosure.

In operation 3310, the electronic device 101 can obtain information as to whether the electronic device 101 is worn. In operation 3320, the electronic device 101 can obtain a bio signal, and in operation 3330, the electronic device 101 can generate a database for the obtained bio signal. According to an embodiment of the present disclosure, the electronic device 101 can store various types of databases. The electronic device 101 can generate and store a reference database to indicate a user's normal range. The reference database can be generated for various health indexes such as blood sugar, blood pressure, or hear rate, and different reference databases can be generated for users, respectively. Meanwhile, the electronic device 101 can generate and store a measured database. The electronic device 101 can measure a bio signal at a predetermined period or when an event occurs and can create a database for measurement results in various period units, e.g., annually, monthly, weekly, or daily. According to an embodiment of the present disclosure, the electronic device 101 can measure blood sugar on an empty stomach, within two hours after meals or before going to bed. The electronic device 101 can measure blood pressure twice a day for seven days. When obtaining a triggering command from the user or at the time that the electronic device 101 is attached or detached, the electronic device 101 can measure a bio signal.

The electronic device 101 can store the database in a storage module therein. Or, the electronic device 101 can store the database in an external cloud server. When the external cloud server receives bio signals from a plurality of wearable electronic devices, the server can store measurement values that have undergone mutual corrections.

In operation 3340, the electronic device 101 can control the electronic device 101 based on the generated database. The above-described process is described below in greater detail with reference to FIGS. 34 and 35.

Figure 34:
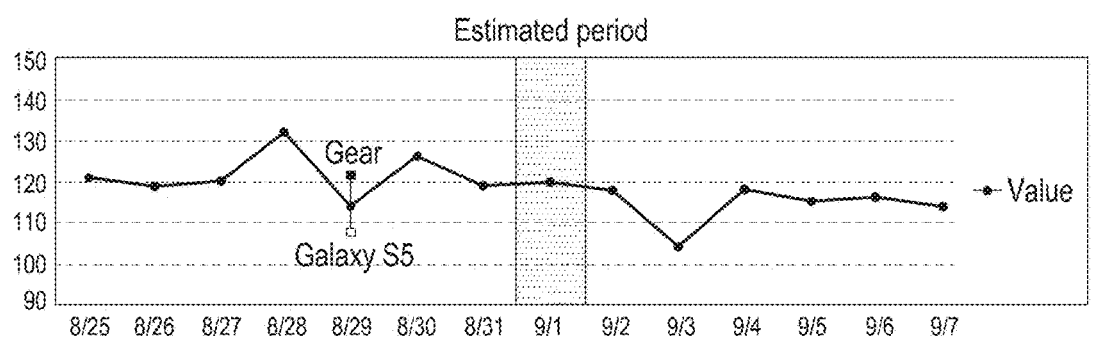
FIGS. 34 and 35 illustrate bio signals measured by an electronic device according to an embodiment of the present disclosure.

First, referring to FIG. 34, the electronic device 101 can compute an estimated value for a time not measured. As shown in FIG. 34, the electronic device 101 might not measure a bio signal at a time corresponding to September 1. In such case, the electronic device 101 can compute the estimated value based on remaining bio signals measured. For example, the electronic device 101 can compute the estimated value using a result of interpolation on the remaining bio signals measured. According to an embodiment of the present disclosure, when the estimated value is predicted to depart from a normal range, the electronic device 101 can notify that measurement is required to be performed by another electronic device of the user.

According to an embodiment of the present disclosure, the electronic device 101 can split the measurement period to manage the database. For example, when the database is managed daily, the electronic device 101 can manage operations according to the user's characteristics on a morning, lunchtime, or evening basis. Meanwhile, the electronic device 101 can recognize a repetitive life pattern through the user's wakeup, movement, or moved location. For example, the electronic device 101 can determine the user's sleep or wakeup through Internet of things (IoT) devices such as lights reacting to the user's movement through the user using peripheral devices. The electronic device 101 can obtain bio signals based on the grasped life pattern. For example, the electronic device 101 can determine a life pattern in which the user measures blood sugar as soon as he wakes up in the morning. The electronic device 101 can disable the blood sugar measuring sensor while in sleep and enable the blood sugar measuring sensor when he wakes up based on the same. Or, when the user does not wake up at the time he usually does, the electronic device 101 can automatically alarm the user even without separately setting the alarm. Or, the electronic device 101 can compare a mean daily intake calorie with the intake calorie of the day to advise the user to refrain from eating food or to do exercise. Or, the electronic device 101 can monitor a time period during which a dangerous issue arises often during the day to increase the measurement cycle. Further, the electronic device 101 can operate based on a particular date, a place grasped by the life pattern, or exercise habit.

Or, the electronic device 101 can manage the database annually. For example, the electronic device 101 can analyze the bio signal database within the last two years to determine flu or cold symptoms every April and October in-between seasons and can provide relevant information to the user before the corresponding periods. For example, the electronic device 101 can give a flu or cold caution or can advise the user to take vitamin pills or recommend him for foods. Further, the electronic device 101 can control an IoT device in the home network to adjust the temperature/humidity and automatically ventilate rooms through windows.

Or, the electronic device 101 can manage the period of measurement of bio signals such as blood sugar, blood pressure, or heart rate while keeping the period short at an early stage, but as the normal range continues to last, the electronic device 101 can increase the measurement period.

Figure 35:
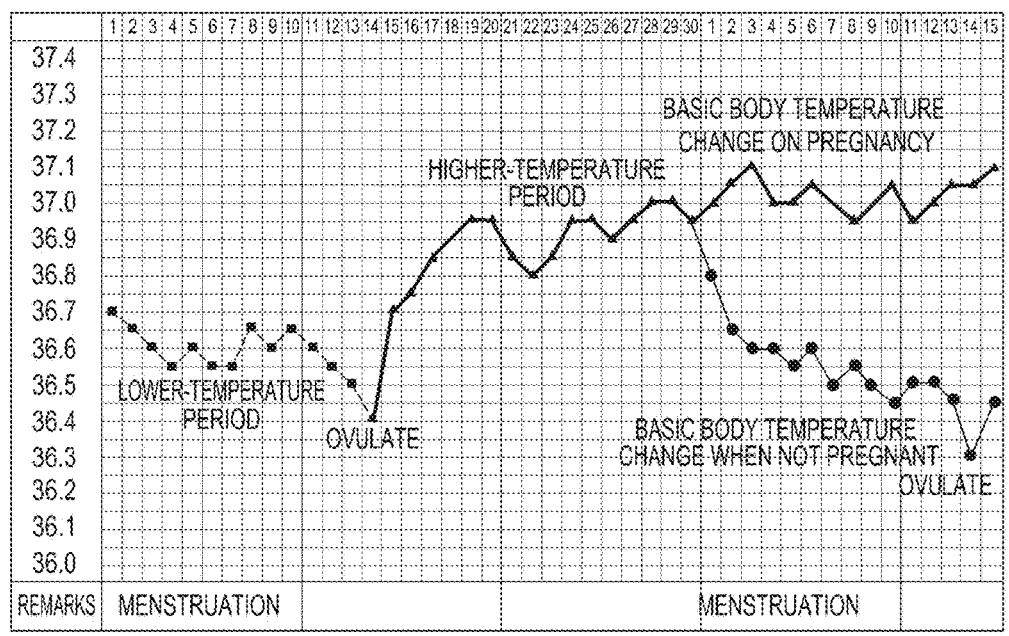

FIG. 35 illustrates a method for managing a female menstrual cycle according to an embodiment of the present disclosure. The electronic device 101 can utilize a database for menstrual-related information, e.g., body temperature and menstrual cycle, for the user's pregnancy or contraception. As shown in FIG. 35, the electronic device 101 can previously store a pattern for changes in body temperature during pregnancy and a pattern for changes in body temperature during contraception. Accordingly, the electronic device 101 can determine whether the user is pregnant by comparing a previously stored pattern with the measured database.

Hereinafter, use of a reference database and the measured database is described according to an embodiment of the present disclosure.

Modes depending on the environment or condition where the user wears the electronic device 101 can be categorized per user activity or per place. Table 1 represents various modes according to embodiments of the present disclosure.

TABLE 1

| Mode | Type |
| --- | --- |
| Indoor exercise | Bench press, treadmill |
| Indoor exercise | Racewalking, jogging, tennis, badminton |
| Daily routine mode | Daily routines, such as idle, sleep, relax, or bathing |

As shown in Table 1, when the user does exercise, he can do indoor or outdoor. While the user does daily routines not exercise, he can wear the electronic device 101.

According to an embodiment of the present disclosure, the electronic device 101 itself can recognize, e.g., moving speed or direction, moving time, or movement, through the global positioning system (GPS) or gyro sensor. Further, since the electronic device 101 can measure, e.g., bio signals or information recognized by sensors, the electronic device 101 can automatically enter into an exercise mode using such information. For example, it can be recognized that the moving speed collected through the electronic device 101 put on the user is about 10 Km/hour and that the user's wrists remain still through the gyro sensor. Further, the heart rate measured is about 85 pulses per minute, and if this shows a substantially similar pattern to the information obtained when the user bikes when the electronic device 101 compares corresponding values fetched from a measurement DB storing existing corresponding information with a current measurement value or with each reference value initially stored in the device, then the electronic device 101 can determine that the user is currently riding bicycle and can switch its mode into exercise/bicycle mode.

Here, the electronic device 101 can provide a guide for wearing to the user to allow him to put the electronic device 101 on an ankle rather than a wrist in order for the user to exactly measure the amount of exercise in the bicycle mode. As another embodiment, the electronic device 101 can grasp the user's moving path through the GPS. When the user took a similar path in the same time period, the electronic device 101 can analyze what action the user has taken, and if the analyzed information can be determined as currently moving to a gym, the electronic device 101 can automatically change the daily routine mode into the exercise mode by referring to the existing mode of the database measured in the gym.

According to an embodiment of the present disclosure, the electronic device 101 can store a data set of reference values that can be referenced per mode. That is, the electronic device 101 can store reference information that can be compared or referenced for each input value, and such set of information can be named a reference database. Here, the reference database can be stored in each electronic device 101 or can be transmitted from a remote storage, e.g., a server, whenever necessary.

Table 2 is an example of a reference database according to an embodiment of the present disclosure.

TABLE 2

| Bio signal | Mode/type | Situation | User/user group | Reference threshold |
| --- | --- | --- | --- | --- |
| Heart rate | Daily routine/idle | Altitude 1 | G1 | R1-R2 |
| Heart rate | Exercise/bicycle | Altitude 1 | G1 | R3-R4 |
| Blood sugar | Daily routine/idle | Altitude 1 | G1 | R5-R6 |
| Blood sugar | Exercise/bicycle | Altitude 1 | G1 | R7-R8 |
| Heart rate | Daily routine/idle | Altitude 2 | G1 | R9-R10 |
| Heart rate | Exercise/bicycle | Altitude 2 | G1 | R11-R12 |
| Blood sugar | Daily routine/idle | Altitude 2 | G1 | R13-R14 |
| Blood sugar | Exercise/bicycle | Altitude 2 | G1 | R15-R16 |

As shown in Table 2, the reference database can include a reference threshold range that functions as a reference for a bio signal per situation and modes and types. The bio signal field in Table 2 can include ECG, EMG, or HRM values sensed by a sensor and by which the user's condition can be assessable. The mode/type field refers to a mode/type in which the user can use the wearable device. The situation field can store the user's current situation. For example, the situation can include, e.g., the altitude, weather, location, or health condition on the current location of the user. The user or user group corresponds to a group where the user belongs.

For example, when the user is a male in his thirties, its corresponding reference value can be set in the electronic device 101. For example, a standard body health index (degree of obesity, weight, girth, amount of muscles, cholesterol, blood pressure, blood sugar or other values) per male or female or per age in Korea can be set. The reference threshold range can have a threshold range value set to be appropriate for each bio signal, mode/type, situation, or user group, and a bio signal, mode/type, situation, or user group collected from the current user can be referenced to set a signal range corresponding thereto. For example, an amount of exercise can be determined considering the user's environment and mode based on the corresponding range value. In connection with Table 2, when measuring a value departing from the R1-R2 range in the place of altitude 1 and in the daily routine mode of heart rate, the electronic device 101 can determine that a change has occurred to the body/health condition. When shifting to an altitude 2 place, the electronic device 101 can use the R9-R10 range as a reference value. Data from the reference database can be used in a fixed or variable manner. Further, the reference database can be renewed or added corresponding to the user's situation. Further, measured signals (ECG, EMG, HRM) can have different magnitudes depending on the portion worn or measured although they are of the same mode or type. For example, when the electronic device 101 is put on the user's wrist in the exercise/bicycle mode, the signal level can be 80 while the signal level can be 100 when the electronic device 101 is put on the user's leg, and thus, the electronic device 101 can correct the obtained bio signal.

Meanwhile, the measured database can be a database dynamically storing data measured from the user separately from the reference database. Here, since the measured database and the reference database are logically distinguished from each other, they are not necessarily configured as separate databases or tables, and if they are distinct from each other for purposes of each information although stored in a single database or table, they can be differentiated from each other. Further, the measured database can also be stored in the server or the electronic device 101. Table 3 is an example of a measured database according to an embodiment of the present disclosure.

TABLE 3

| Field name | Description |
| --- | --- |
| ⓐ user information | Identify the user of the wearable device |
| Portion worn/measured | Hand, lower arm, upper arm, lower leg, upper leg, waist |
| Measuring sensor | ECG, EMG, HRM |
| ⓑ bio signal | ECG, EMG, or HRM value measured by sensor - heart rate, respiration rate, oxygen saturation, blood pressure, blood sugar, etc. |
| Time measured | Time measured |
| Location measured | Indoor/outdoor/GPS etc. |
| ⓒ mode/type | <A. mode/type define> |
| ⓓ situation | altitude, weather, location, health condition (disease history) |
| application | identifier meaning an application or domain during login |
| device ID | identifier for measuring device |
| state | means the condition of health or other state of having problems |

The fields of Table 3 can list various information included in a database according to an embodiment of the present disclosure. Such information can be configured of various schemas, and other various fields can be added or edited depending on user situations and can be configured of one or more tables.

The use log or record of the electronic device 101 can be stored in the database with the field values as shown in Table 3 and can be periodically measured at predetermined periods or can be intermittently measured when particular events occur. That is, different periods of measurement can be set according to the current mode set to the electronic device 101. The measurement period can be flexibly updated, and the electronic device 101 can update the measurement period by referring to one or more information items of data regarding time, place, and past change in body.

For example, the electronic device 101 can monitor whether similar pattern of changes in blood sugar are measured at particular times every day by observing changes in blood sugar among the various fields included in the measured database. The electronic device 101 can determine that the pattern of changes in blood sugar corresponds to the meal time. In such case, the electronic device 101 can determine a predetermined period before and after the meal time as the period of measuring data regarding changes in blood sugar. Further, the electronic device 101 can measure blood sugar only within the determined period. As another example, the electronic device 101 can obtain the information indicating that more muscular movements and calorie consumption repeatedly occur at the same time in the same place on particular days. The electronic device 101 can guess that the corresponding time is an exercise time and can measure bio signals required to determine the amount of exercise only for the guessed exercise time.

According to an embodiment of the present disclosure, the electronic device 101 can update the reference database. For example, the electronic device 101 can determine whether ⓑ bio signal is included within a normal range using the reference database based on items, e.g., ⓐ user information portion worn/measured measuring sensor, ⓒ mode/type, and ⓓ situation in Table 3. The electronic device 101 can display a result of the determination on a separate field, the "state" field, and can notify the user of the determination result. The user can input a feedback corresponding to the notification, and the electronic device 101 can update the reference database with the received user feedback. The "portion worn/measured" field can store detailed information as well as various body portions where the electronic device 101 is placed. The detailed information can include a specific position, angle, or degree of loosening. The "bio signal" field can store values relating to electrical signals (ECG or EMG) or optical signals (HRM) and can store resultant values obtained by analyzing the electrical signals (ECG or EMG) or optical signals (HRM). Further, the "bio signal" field can be variously configured with one or more information items. The application field can display an identifier for an application relating to the corresponding log. For example, when the user's motion is recognized while playing game, a game identifier can be displayed on the application field.

According to an embodiment of the present disclosure, the electronic device 101 can change the daily routine mode, e.g., the idle mode, into the exercise mode, e.g., the jogging mode, using the measured database. The electronic device 101 can carry out such mode change based on the movement information regarding the electronic device 101 and can determine whether the user is in a good health condition by making comparison to the reference database. When determining that the user is not in a good health condition, the electronic device 101 can output an alert.

Table 4 represents records for some fields recorded in the measured database in the exercise or jogging mode according to an embodiment of the present disclosure.

TABLE 4

| idx | user information | bio signal type/value | measurement time | location | mode/type | situation | state |
|---|---|---|---|---|---|---|---|
| 1 | Hsj(G1) | blood pressure/110 mmHg | 00,00,01 | A | exercise/jogging | Altitude 1 | normal |
| 2 | Hsj(G1) | heart rate/100 mg/dl | 00,00,01 | B | exercise/jogging | Altitude 1 | normal |
| 3 | Hsj(G1) | blood pressure/112 mmHg | 00,00,05 | C | exercise/jogging | Altitude 2 | normal |
| 4 | Hsj(G1) | blood pressure/150 mmHg | 00,00,05 | D | exercise/jogging | Altitude 2 | abnormal |

It is assumed as shown in Table 4 that the user Hsj is a 35 years old female and belongs to the G1 group. In the reference database, the threshold range for the G1 group under the situations of exercise/jogging mode and altitude 2 can be defined as 75 to 120 mmHg.

Since, for record 3, the blood pressure measured is 112 and thus belongs to the threshold range, the electronic device 101 can determine that it is normal. Since, for record 4, the blood pressure measured is 150 and thus exceeds the threshold range, the electronic device 101 can determine that it is abnormal and can output a notification to instruct the user to stop exercise.

According to an embodiment of the present disclosure, when sensing a problem/emergency while measuring bio signals from the user even in the daily routine mode, the electronic device 101 can receive tracking information before and after the situation and can send it to the user. For example, the electronic device 101 can send a report for the situation where a problem with the sleeping pattern has occurred to the user. In other words, when sensing an abnormality in the respiration rate while measuring the respiration rate information in the database periodically measured during sleep, the electronic device 101 can generate an alarm to awaken the user or output a notification to a nearby third party. The electronic device 101 can output detailed information as to the corresponding situation.

As another example, under the circumstance where the electronic device 101 senses a car accident, the electronic device 101 can output information on the move for a predetermined time period before and after the accident. Or, the electronic device 101 can send the corresponding information to another electronic device provided in the emergency room. That is, the electronic device 101 can send a request for data query for a time within the time period of the accident to the measured database and analyze the same. The electronic device 101 can determine whether the bio information such as pulse rate or blood pressure field has an abnormality from data received corresponding to the query. When an abnormality occurs, the electronic device 101 can send a result of the analysis to an electronic device managed by the medical staff. While moving from the accident scene to the emergency room, the electronic device 101 can output tracking information for a predetermined time before and after.

According to an embodiment of the present disclosure, the electronic device 101 can predict what kind of exercise best fits the user by analyzing data measured from the user. In particular, for users having a history of having suffered from diabetes, heart diseases or other diseases requiring continuous treatment and care, the electronic device 101 can collect and store, e.g., blood sugar values or hear rates before and after a particular exercise time and can send a request for data query to the measured database. The electronic device 101 can analyze the data obtained as a result of the query and can determine whether the blood sugar or heart rate field is an abnormal range or back in the normal range based on the analysis result. The electronic device 101, when it remains within the abnormal range for a significant time, can output an alert or warning to the user. Or, the electronic device 101 can choose a path or mode in which the exercise can be done safely without entering into the abnormal range and can output a notification to recommend the user for the path or mode.

According to an embodiment of the present disclosure, the electronic device 101 can make a recommendation in connection with medicines. Under the situation where the user has to take some medicine due to his disease, the electronic device 101 can analyze correlations relating to various modes done by the user after he took a particular medicine. By doing so, the electronic device 101 can recommend the user for a set of modes and a most efficient medicine. Likewise, the electronic device 101 can inform the user of weak effects or occurrence of side effects through the analysis result. Or, the electronic device 101 can send the corresponding information to another electronic device.

According to an embodiment of the present disclosure, the electronic device 101 can analyze the user's sleeping pattern. For users who has diabetes or heart diseases, the electronic device 101 can detect the risk of occurrence of an emergency during sleep as well as daily routines or exercise modes. The electronic device 101 can measure major bio signals while the user is in sleep, and when a particular standard is not met or exceeded, the electronic device 101 can output an alert. Or, the electronic device 101 can recommend the user for a proper sleep habit. For example, the electronic device 101 can recommend the user for food intake conditions, best time period for sleep, and exercise habits.

According to an embodiment of the present disclosure, the electronic device 101 can transmit information on measured bio signals to another electronic device in order to secure continuity of the measured database. The other electronic device can secure the continuity over the whole database by measuring a bio signal from the user corresponding to received information.

Figure 36:
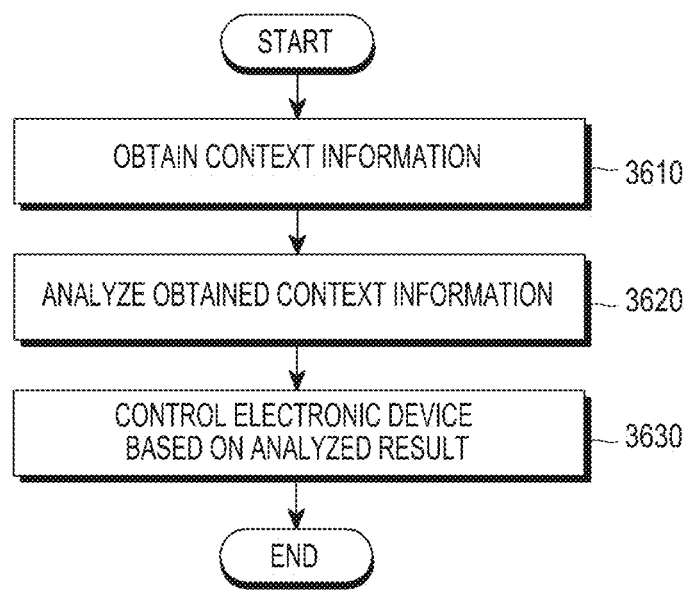
FIG. 36 is a flowchart illustrating a method for controlling an electronic device according to an embodiment of the present disclosure.

FIG. 36 is a flowchart illustrating a method for controlling an electronic device according to an embodiment of the present disclosure.

In operation 3610, the electronic device 101 can obtain context information. For example, the electronic device 101 can obtain the context information based on measured bio signals, user patterns, time information, or place information.

In operation 3620, the electronic device 101 can analyze the context information, and in operation 3630, the electronic device 101 can control the electronic device based on a result of analysis of the context information.

Figure 37:
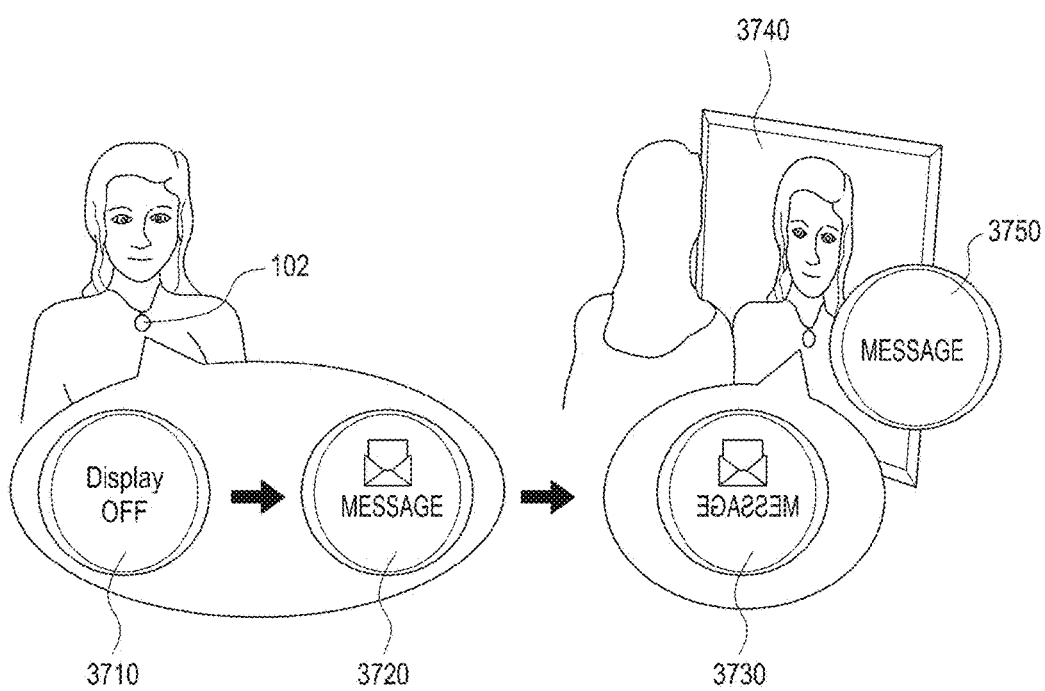
FIG. 37 illustrates an example in which an electronic device interworks with a smart mirror according to an embodiment of the present disclosure.

FIG. 37 illustrates an example in which an electronic device interworks with a smart mirror according to an embodiment of the present disclosure.

As shown in FIG. 37, the electronic device 101 can interwork with a smart mirror 3740. The electronic device 101 can establish a connection with the smart mirror 3740 based on a predetermined communication scheme, and the electronic device 101 can accordingly grasp interworking with the smart mirror 3740. The electronic device 101 used to be in a display-off state 3710 can display a user interface 3720 to indicate the reception of a message. In this case, the electronic device 101 can display an inverse user interface 3730 based on the interworking with the smart mirror 3710. Accordingly, the user can identify the inverse user interface 3730 in an inversed position through the mirror and can thus view the original user interface 3750.

Figure 38:
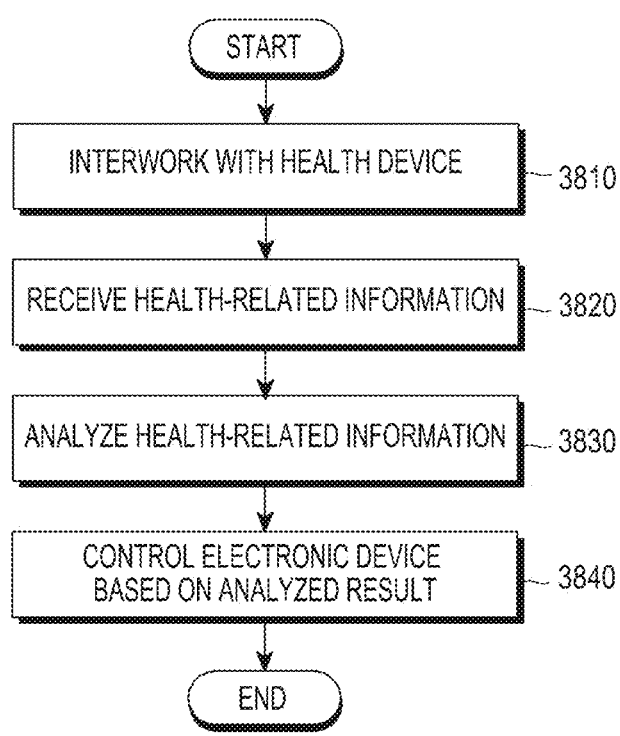
FIG. 38 is a flowchart illustrating a method for controlling an electronic device according to an embodiment of the present disclosure.

FIG. 38 is a flowchart illustrating a method for controlling an electronic device according to an embodiment of the present disclosure.

In operation 3810, the electronic device 101 can interwork with a health device. Here, the health device can be an electronic device supporting the exercise of the user and can transmit/receive data through communication with the electronic device 101.

In operation 3820, the electronic device 101 can receive health-related information from the health device. The health-related information can include at least one of the user's exercise information and the user's bio signal.

In operation 3830, the electronic device 101 can analyze the health-related information, and in operation 3840, the electronic device 101 can control the electronic device 101 based on a result of the analysis.

According to an embodiment of the present disclosure, when the user wearing the electronic device 101 arrives at the place he regularly does exercise, the electronic device 101 can determine that the place is one for exercise based on the user's current location and can enter into a fitness tracking mode. In particular, the electronic device 101 can more correctly change modes by checking whether the history he did exercise before in the same place is present in the database.

Further, when the user approaches a particular piece of equipment for indoor exercise, e.g., a treadmill, the electronic device 101 can switch to a jogging-related mode to be able to use the jogging-related data in the existing database. Further, when the user approaches, e.g., a piece of bench press equipment, the electronic device 101 can switch into a mode in which it can check and record the state of arm muscles. Here, to determine the type of the exercise equipment the user is approaching, an indoor positioning scheme or pairing of the electronic device 101 through short-range communication or tags embedded in each piece of equipment can be used.

Here, in some modes, the electronic device 101 can utilize data collected in a place other than where the user is currently doing exercise. For example, for a treadmill, the electronic device 101 can provide integrated information, synced with measured data when the user does jogging outdoors. When computing the total distance moved until the user terminates the exercise, the electronic device 101, rather than displaying only the distance computed from the treadmill, can calculate and provide the total distance he has moved from starting with his routines in the morning until he finally uses the treadmill in the place where he does exercise after calling it a day. According to an embodiment of the present disclosure, although the electronic device 101 can provide the integrated result, the integrated information can also be provided through the display of the treadmill.

Further, when the user uses the treadmill, the electronic device 101 can provide information familiar to the user. For example, the electronic device 101 can store information regarding the location or place where the user regularly goes when doing outdoor exercise. When the user uses the treadmill indoor, the electronic device 101, rather than simply displaying a numerical value indicating how long he has walked in kilometers, can also provide information with respect to the user's familiar place or the position of a landmark around. For example, when the user regularly commutes by walking, the electronic device 101 can compute the distance between the user's home and workplace and can indicate "2 km. You have walked the distance between your home and workplace" to allow the user to easily appreciate the distance by which he has done exercise indoor through the treadmill. Unless there is no previous walking record, the electronic device 101 can indicate "you have walked the distance between OO department store and XX movie theater" using the position of ambient landmarks.

According to an embodiment of the present disclosure, when the user doing exercise outdoor moves in the place with a piece of exercise equipment presenting a similar exercise effect, the electronic device 101 can perform control so that the screen displayed on the piece of exercise equipment and the electronic device 101 can be displayed on a second display, e.g., the display of the piece of exercise equipment or a portable device, thereby securing the continuity of obtained information. For example, when the user moves from his home to a gym by jogging and then hops on a treadmill, the electronic device 101 can perform control to automatically output the distance the user has moved thus far on the screen of the treadmill. By contrast, when the user finishes exercise on the treadmill and moves from the gym to home by jogging, the electronic device 101 can also display the total distance he has moved.

According to an embodiment of the present disclosure, the electronic device 101 can determine whether the user can do exercise using a health device interworking therewith. The electronic device 101 can measure a bio signal from the user and can measure the user's health condition or body condition. The electronic device 101 can determine a risk as to the use of the health device based on the measured health or body condition. When the user determines that the user of the health device is dangerous, the electronic device 101 can previously alert the user to this. For example, when the user determined to be in muscle fatigue through analysis of an EMG signal attempts to use exercise equipment, e.g., a bench press machine, the electronic device 101 can issue an alert message saying "20 Kg or more can be dangerous under your condition" or can provide a notification as to such situation to a trainer so that the user can be properly guided. Or, after measuring an EMG signal, the electronic device 101 can digitize the same to grasp muscle stress, fatigue, or injury and can provide it to the user.

According to an embodiment of the present disclosure, the electronic device 101 can compute a movement on the worn portion of the electronic device 101 during workout and can output a voice or display a user interface for the best position. When the user is playing tennis, the electronic device 101 can analyze the state of muscles and notify the user of the best position. When sensing an imbalance in muscle tension between left and right sides, the electronic device 101 can advise the user to put more tension to the weaker side. The electronic device 101 can determine the position the user usually takes, and when the position is right-to-left asymmetric, the electronic device 101 can advise the user to take a right position when the user sits on chair or walks.

According to an embodiment of the present disclosure, a method for controlling an electronic device can include obtaining a portion where the electronic device is worn and controlling the electronic device based on the obtained worn portion.

According to an embodiment of the present disclosure, controlling the electronic device can include determining a mode determination signal corresponding to the worn portion and controlling the electronic device based on the mode determination signal. Controlling the electronic device based on the mode determination signal can determine that, when the worn portion is determined as a wrist, determines an ECG signal sensed from the wrist as the mode determination signal and controlling the electronic device based on the ECG signal. Controlling the electronic device can determine the user's health condition based on the ECG signal.

According to an embodiment of the present disclosure, when the worn portion is determined to be a forearm, controlling the electronic device can determine that an EMG signal sensed from the forearm is the mode determination signal and can control the electronic device based on the EMG signal. Controlling the electronic device can generate a control signal based on the EMG signal. The control signal can be a signal to control the electronic device or another electronic device communicating with the electronic device.

According to an embodiment of the present disclosure, obtaining the worn portion can obtain the worn portion based on at least one of length information regarding a strap of the electronic device and movement information regarding the electronic device.

According to an embodiment of the present disclosure, the method for controlling the electronic device can further include determining that the worn portion of the electronic device is varied when the electronic device moves in a first direction as the length of the strap of the electronic device is varied.

According to an embodiment of the present disclosure, the method for controlling the electronic device can further include, when the worn portion is a wrist, determining a direction that the electronic device is worn and controlling the electronic device based on the determined direction. Controlling the electronic device based on the determined worn direction can display a screen corresponding to a security mode when the worn direction faces an opposite direction of a position of the user. Obtaining the worn portion can determine whether the worn portion of the electronic device is a left wrist or right wrist. Controlling the electronic device can determine an orientation of a screen of the electronic device corresponding to whether the worn portion is the left wrist or right wrist. Controlling the electronic device can determine direction information regarding a control signal based on movement information regarding the electronic device, corresponding to whether the worn portion is the left wrist or right wrist. Obtaining the worn portion can determine whether the worn portion is the left wrist or the right wrist based on a coupled state of a coupler of the electronic device and movement information regarding the electronic device.

According to an embodiment of the present disclosure, in the method for controlling the electronic device, controlling the electronic device can control the electronic device based on a distance between the worn portion and a predetermined body portion of the user. Controlling the electronic device can control an output volume of the electronic device based on the distance between the worn area and the user's ear. Controlling the electronic device can control a screen resolution of the electronic device based on the distance between the worn area and the user's eye. Controlling the electronic device can control a microphone sensitivity of the electronic device based on the distance between the worn area and the user's mouth. Controlling the electronic device can control a vibration output of the electronic device based on a vibration strength. When determining that the worn portion is around the neck, controlling the electronic device can inverse and display a screen of the electronic device.

According to an embodiment of the present disclosure, the method for controlling the electronic device can further include inducing proper wearing corresponding to the worn portion. Inducing the proper wearing can include obtaining a sensed signal from the user, detecting an error signal from the sensed signal, and when the error signal exceeds a predetermined level, inducing the proper wearing. Inducing the proper wearing can include changing a length of a strap so that the electronic device is worn in tight contact with the worn area. Inducing the proper wearing can include sending a request for moving the electronic device to another worn area for obtaining a sensed signal.

According to an embodiment of the present disclosure, the method for controlling the electronic device can further include obtaining a sensed signal from the worn portion, obtaining a fatigue of the worn portion from a result of analyzing the sensed signal, and performing an operation corresponding to the fatigue when the fatigue exceeds a predetermined level. The operation corresponding to the fatigue can alternately increase and decrease the length of a strap of the electronic device or waiting until the fatigue is down to the predetermined level or less.

According to an embodiment of the present disclosure, the method for controlling the electronic device can include obtaining a sensed signal from the worn portion and inducing a predetermined user position corresponding to obtaining the sensed signal.

According to an embodiment of the present disclosure, the method for controlling the electronic device can further include obtaining a voice from the user as obtained through a microphone of the electronic device and displaying a message indicating to stop generating the voice while obtaining the sensed signal. According to an embodiment of the present disclosure, the method for controlling the electronic device can further include determining whether the user position is taken based on a sensed signal from a motion sensor of the electronic device.

According to an embodiment of the present disclosure, the method for controlling the electronic device can further include establishing a communication connection with the other electronic device and transmitting length information regarding a strap of the electronic device to the other electronic device, wherein when determining that no change is made to the length information regarding the strap, the other electronic device can determine that user authentication succeeds.

According to an embodiment of the present disclosure, the method for controlling the electronic device can further include obtaining an interoperation with an external tag and determining the worn portion based on the obtained interoperation. According to an embodiment of the present disclosure, the method for controlling the electronic device can further include measuring a bio signal, receiving at least one of information on the thickness of a piece of clothes and information on the material of the piece of clothes from the external tag, and compensating for the bio signal based on the at least one of the information on the thickness of the piece of clothes and the information on the material of the piece of clothes.

According to an embodiment of the present disclosure, the method for controlling the electronic device can further include obtaining first information from the other electronic device, obtaining second information of the same type as the first information sensed by the electronic device, and determining the worn portion based on a result of comparing the first information with the second information.

According to an embodiment of the present disclosure, the method for controlling the electronic device can include determining whether the electronic device is attached or detached and controlling the electronic device based on the determination.

Determining whether the electronic device is attached or detached can determine whether the electronic device is worn based on movement information regarding the electronic device and a state in which of the coupler of the electronic device is coupled. Determining whether the electronic device is attached or detached can determine that the electronic device is worn when detecting that the coupler is coupled after the electronic device has horizontally moved. Determining whether the electronic device is attached or detached can determine whether the worn portion of the electronic device is the left wrist or right wrist based on the direction along which the electronic device horizontally moves.

According to an embodiment of the present disclosure, the method for controlling the electronic device can generate a control signal corresponding to the left wrist or right wrist based on the worn portion.

According to an embodiment of the present disclosure, the method for controlling the electronic device can further include, when the electronic device is determined to be worn, obtaining a sensed signal from the user, detecting an error signal from the sensed signal, and when the error signal exceeds a predetermined level, inducing the proper wearing.

According to an embodiment of the present disclosure, the method for controlling the electronic device can further include, when the electronic device is determined to be worn, obtaining a sensed signal from the user and performing user authentication based on the sensed signal. Determining whether the electronic device is attached or detached can determine whether the electronic device is taken off based on movement information regarding the electronic device and the coupled state of the coupler of the electronic device. Controlling the electronic device can control the electronic device based on the place where the electronic device is taken off.

According to an embodiment of the present disclosure, the method for controlling the electronic device can further include determining that the electronic device is taken off indoor.

According to an embodiment of the present disclosure, the method for controlling the electronic device can further include performing wireless charging when the electronic device is disposed within a wireless chargeable range.

According to an embodiment of the present disclosure, the method for controlling the electronic device can further include sending out a wireless charging unavailable message when the electronic device is disposed off a wireless chargeable range.

According to an embodiment of the present disclosure, the method for controlling the electronic device can further include determining that the electronic device is taken off outdoor.

According to an embodiment of the present disclosure, the method for controlling the electronic device can further include sending out an alert message when the distance between the electronic device and the user exceeds a predetermined level.

According to an embodiment of the present disclosure, the method for controlling the electronic device can further include measuring the distance between the electronic device and the user based on the strength of a communication signal between the electronic device and another electronic device carried by the user. The predetermined level can be set based on the strength of ambient noise sensed by the electronic device.

According to an embodiment of the present disclosure, the method for controlling the electronic device can further include obtaining a sensed signal from the user before determining whether the electronic device is taken off, and when determining that the electronic device is taken off, determining whether continuously obtaining the sensed signal is required.

According to an embodiment of the present disclosure, the method for controlling the electronic device can further include analyzing the sensed signal to obtain predicted health information, and when the predicted health information corresponds to a dangerous range, informing that continuously obtaining the sensed signal is required.

According to an embodiment of the present disclosure, the method for controlling the electronic device can further include receiving a predicted variation in a bio signal after taking a medicine, measuring a first bio signal before taking the medicine and a second bio signal after taking the medicine, and determining whether taking the medicine is proper by comparing a variation between the first bio signal and the second bio signal and the predicted bio signal variation.

According to an embodiment of the present disclosure, the method for controlling the electronic device can further include receiving the predicted variation in the bio signal after taking the medicine, receiving information on a time of taking the medicine, and informing the time of taking the medicine.

Each of the aforementioned components of the electronic device can include one or more parts, and a name of the part can vary with a type of the electronic device. The electronic device in accordance with various embodiments of the present disclosure can include at least one of the aforementioned components, omit some of them, or include other additional component(s). Some of the components can be combined into an entity, but the entity can perform the same functions as the components can do.

The term 'module' can refer to a unit including one of hardware, software, and firmware, or a combination thereof. The term 'module' can be interchangeably used with a unit, logic, logical block, component, or circuit. The module can be a minimum unit or part of an integrated component. The module can be a minimum unit or part of performing one or more functions. The module can be implemented mechanically or electronically. For example, the module can include at least one of application specific integrated circuit (ASIC) chips, field programmable gate arrays (FPGAs), or programmable logic arrays (PLAs) that perform some operations, which have already been known or will be developed in the future.

According to an embodiment of the present disclosure, at least a part of the device (e.g., modules or their functions) or method (e.g., operations) can be implemented as instructions stored in a computer-readable storage medium e.g., in the form of a program module. The instructions, when executed by a processor (e.g., the processor 120), can enable the processor to carry out a corresponding function. The computer-readable storage medium can be e.g., the memory 130.

The computer-readable storage medium can include a hardware device, such as hard discs, floppy discs, and magnetic tapes (e.g., a magnetic tape), optical media such as compact disc read only memories (ROMs) (CD-ROMs) and digital versatile discs (DVDs), magneto-optical media such as floptical disks, ROMs, random access memories (RAMs), flash memories, and/or the like. Examples of the program instructions can include not only machine language codes but also high-level language codes which are executable by various computing means using an interpreter. The aforementioned hardware devices can be configured to operate as one or more software modules to carry out exemplary embodiments of the present disclosure, and vice versa.

Modules or programming modules in accordance with various embodiments of the present disclosure can include at least one or more of the aforementioned components, omit some of them, or further include other additional components. Operations performed by modules, programming modules or other components in accordance with various embodiments of the present disclosure can be carried out sequentially, simultaneously, repeatedly, or heuristically. Furthermore, some of the operations may be performed in a different order, or omitted, or include other additional operations.

According to an embodiment of the present disclosure, there is provided a storage medium storing instructions executed by at least one processor to enable the processor to perform at least one operation that may include obtaining a portion where the electronic device is worn and controlling the electronic device based on the obtained worn portion.

As is apparent from the foregoing description, according to an embodiment of the present disclosure, an area where an electronic device is worn may be obtained, and the electronic device may be controlled based on the obtained area.

According to an embodiment of the present disclosure, whether an electronic device is worn may be obtained, and the electronic device may be controlled based on whether the electronic device is worn.

According to an embodiment of the present disclosure, there is provided a method for more efficiently controlling an electronic device, which operates based on whether or where the electronic device is worn.

Although the present disclosure has been described with an exemplary embodiment, various changes and modifications may be suggested to one skilled in the art. It is intended that the present disclosure encompass such changes and modifications as fall within the scope of the appended claims.

What is claimed is:
1. A method for controlling an electronic device, the method comprising:
sensing, using a sensor, whether the electronic device is attached to a human body;
controlling the electronic device or another electronic device interworkable with the electronic device based on at least one of:
information regarding a body condition of a user, measured when the electronic device is attached,
information regarding a position wherein the electronic device is attached or detached,
authentication information regarding the user wearing the electronic device, or
information regarding a time when the electronic device is attached or detached;
wherein the information regarding the user's body condition measured when the electronic device is attached includes at least one of a blood sugar value, a blood pressure value, a heart rate value, a temperature value, an electromyogram (EMG) value, an electrocardiogram (ECG) value, an electroencephalogram (EEG) value, and a vein value,
generating second information including at least one of health information, authentication information, and emotion information using at least one of the blood sugar value, the blood pressure value, the heart rate value, the temperature value, the EMG value, the ECG value, the EEG value, and the vein value,
sensing, using the sensor, whether the electronic device is detached from the human body;
determining whether the electronic device is detached; and
determining whether information regarding the body condition needs to be continuously obtained based on the second information when determining that the electronic device is detached.

2. The method of claim 1, wherein sensing whether the electronic device is attached to the human body includes sensing whether the electronic device remains attached or detached.

3. The method of claim 2, wherein sensing whether the electronic device is attached to the human body includes sensing whether the electronic device is attached based on movement information regarding the electronic device and a coupling state of a coupler of the electronic device.

4. The method of claim 3, wherein sensing whether the electronic device is attached to the human body includes sensing that the electronic device is attached when detecting the coupling state of the coupler as attached after the electronic device horizontally moves.

5. The method of claim 4, further comprising sensing whether the electronic device is attached on a left wrist or a right wrist based on a direction in which the electronic device horizontally moves.

6. The method of claim 2, wherein sensing whether the electronic device is attached to the human body includes determining whether the electronic device contacts the human body when sensing that the electronic device is attached.

7. The method of claim 6, wherein sensing whether the electronic device is attached to the human body includes obtaining a sensed signal from the user and determining whether the electronic device is attached in tight contact with the human body by comparing a per-time measurement value of the sensed signal with a predetermined reference value.

8. The method of claim 7, further comprising:
detecting an error signal from the sensed signal; and
inducing the electronic device to be properly attached when the error signal exceeds a predetermined level.

9. The method of claim 8, wherein inducing the electronic device to be properly attached includes performing control to vary a length of a strap of the electronic device so that the electronic device is attached in tight contact with an attached position.

10. The method of claim 1, wherein sensing whether the electronic device is attached to the human body includes sensing whether the electronic device is detached based on movement information regarding the electronic device and a coupling state of a coupler of the electronic device,
wherein the method further comprises determining that a position where the electronic device is detached is a predetermined first place, and
setting the first place by a user's designation or a result of analyzing per-time location information.

11. The method of claim 10, further comprising performing wireless charging when the electronic device is positioned within a wirelessly chargeable range.

12. The method of claim 10, further comprising transmitting a message indicating that wireless charging is impossible when the electronic device is positioned outside a wirelessly chargeable range.

13. The method of claim 10, further comprising determining that a place where the electronic device is detached is a place other than the predetermined first place.

14. The method of claim 13, further comprising transmitting an alert message when a distance between the electronic device and the user exceeds a predetermined level.

15. The method of claim 14, wherein the predetermined level is set based on a strength of ambient noise sensed by the electronic device.

16. The method of claim 10, further comprising:
obtaining a sensed signal from the user before determining whether the electronic device is detached; and
determining whether the sensed signal needs to be continuously obtained after determining that the electronic device is detached.

17. The method of claim 16, further comprising:
obtaining predicted health information by analyzing the sensed signal; and
notifying that the sensed signal needs to be continuously obtained when the predicted health information corresponds to a dangerous area.

18. The method of claim 1, further comprising obtaining a position where the electronic device is attached based on at least one of a sensed signal sensed from the user, length information regarding a strap of the electronic device, and movement information regarding the electronic device.

19. The method of claim 1, wherein controlling the electronic device or the other electronic device interworkable with the electronic device includes controlling the electronic device based on a distance between a position where the electronic device is attached and a predetermined body portion of the user.

20. The method of claim 1, wherein controlling the electronic device or the other electronic device interworkable with the electronic device includes inversing and displaying a screen of the electronic device when determining that a position where the electronic device is attached is around a neck.

21. The method of claim 1, wherein controlling the electronic device or the other electronic device interworkable with the electronic device includes measuring a bio signal, receiving at least one of information on a thickness of a piece of clothes and information on a material of the piece of clothes from an external tag, and compensating for the bio signal based on the at least one of the information on the thickness of the piece of clothes and the information on the material of the piece of clothes.

22. An electronic device, comprising:
a sensor;
a processor; and
a memory electrically connected to the processor, wherein the memory is configured to store an instruction, when executed by the processor, to enable the processor to:
sense, using the sensor, whether the electronic device is attached on a human body;
control the electronic device or another electronic device interworkable with the electronic device based on at least one of:
information regarding a body condition of a user measured when the electronic device is attached,
information regarding a position where the electronic device is attached or detached,
authentication information regarding the user wearing the electronic device, or
information regarding a time when the electronic device is attached or detached,
wherein the information regarding the user's body condition measured when the electronic device is attached includes at least one of a blood sugar value, a blood pressure value, a heart rate value, a temperature value, an electromyogram (EMG) value, an electrocardiogram (ECG) value, an electroencephalogram (EEG) value, and a vein value,
generate second information including at least one of health information, authentication information, and emotion information using at least one of the blood sugar value, the blood pressure value, the heart rate value, the temperature value, the EMG value, the ECG value, the EEG value, and the vein value,
sense, using the sensor, whether the electronic device is detached from the human body;
determine whether the electronic device is detached; and
determine whether information regarding the body condition needs to be continuously obtained based on the second information when determining that the electronic device is detached.

23. The electronic device of claim 22, further comprising at least one sensor configured to measure at least one of a bio signal of the user wearing the electronic device and movement information regarding the electronic device, wherein the memory is configured to store an instruction executed to enable the process to determine the information regarding the at least one of the body condition, the user wearing the electronic device, a position where the electronic device is attached or detached, and a time when the electronic device is attached or detached based on the at least one of the bio signal and the movement information.

* * * * *